(12) United States Patent
Rigas

(10) Patent No.: US 11,510,931 B2
(45) Date of Patent: Nov. 29, 2022

(54) COMPOSITIONS AND METHODS FOR TREATING OPHTHALMIC CONDITIONS

(71) Applicant: MEDICON PHARMACEUTICALS, INC., Setauket, NY (US)

(72) Inventor: Basil Rigas, Setauket, NY (US)

(73) Assignee: MEDICON PHARMACEUTICALS, INC., Setauket, NY (US)

( * ) Notice: Subject to any disclaimer, the term of this patent is extended or adjusted under 35 U.S.C. 154(b) by 282 days.

(21) Appl. No.: 16/337,734

(22) PCT Filed: Sep. 28, 2017

(86) PCT No.: PCT/US2017/054051
§ 371 (c)(1),
(2) Date: Mar. 28, 2019

(87) PCT Pub. No.: WO2018/064354
PCT Pub. Date: Apr. 5, 2018

(65) Prior Publication Data
US 2019/0343848 A1    Nov. 14, 2019

Related U.S. Application Data

(60) Provisional application No. 62/564,595, filed on Sep. 28, 2017, provisional application No. 62/400,955, filed on Sep. 28, 2016.

(51) Int. Cl.
*A61K 31/661* (2006.01)
*A61P 27/02* (2006.01)
*A61P 27/04* (2006.01)

(52) U.S. Cl.
CPC ............ *A61K 31/661* (2013.01); *A61P 27/02* (2018.01); *A61P 27/04* (2018.01)

(58) Field of Classification Search
CPC .............................. A61K 31/661; A61P 27/02
See application file for complete search history.

(56) References Cited

U.S. PATENT DOCUMENTS

| 4,309,566 A | 1/1982 | Konz et al. |
| 5,886,030 A | 3/1999 | Maniar |
| 8,236,820 B2 * | 8/2012 | Rigas ................. A61P 9/12 514/320 |
| 2007/0299124 A1 | 12/2007 | Ousler, III et al. |
| 2008/0153746 A1 | 6/2008 | Alvarez |
| 2012/0295979 A1 | 11/2012 | Prentice et al. |
| 2013/0225529 A1 | 8/2013 | Rigas |
| 2014/0315834 A1 | 10/2014 | Rigas |
| 2016/0051526 A1 | 2/2016 | Rothaul et al. |
| 2020/0246359 A1 | 8/2020 | Rigas |

FOREIGN PATENT DOCUMENTS

| CN | 1976692 | 6/2007 |
| WO | 2008153746 | 12/2008 |
| WO | 2018064354 | 4/2018 |

OTHER PUBLICATIONS

International Search Report dated Jan. 23, 2018 in connection with International Patent Application No. PCT/US2017/054051.
Written Opinion dated Jan. 23, 2018 in connection with International Patent Application No. PCT/US2017/054051.
Extended European Search Report dated May 19, 2020 in connection with European Patent Application No. 17857434.9.
Honkanen, R. et al., "Phosphosulindac is Efficacious in an Improved Concanavalin A-based Rabbit Model of Chronic Dry Eye Disease", Transl Res., 198:58-72, (2018).
International Application No. PCT/US2018/053451; International Search Report & Written Opinion of the International Searching Authority, dated Jan. 23, 2019; 15 pages.
Sullivan, D. et al., "Lacrimal Gland, Tear Film, and Dry Eye Syndromes 2: Basic Science and Clinical Relevance", vol. 438 of Advances in Experimental Medicine and Biology, p. 707, (2012).
U.S. Appl. No. 16/651,846; Final Office Action, dated Oct. 7, 2021; 14 pages.
"Dry Eye Syndrome Preferred Practice Pattern", American Academy of Opthalmology, p. 287-p. 290 and p. 306-p. 313, (2018).
Burling-Phillips, L. et al., "Topical NSAIDS: Best Practices for Safe Use", Eyenet, 33-34, (2013).
Foulks, G. et al., "Clinical Guidelines for Management of Dry Eye Associated with Sjögren Disease", The Ocular Surface, 13(2):118-132, (2015).
Huang, W. et al., "Phospho-Sulindac (OXT-328) Inhibits Dry Eye Disease in Rabbits: A Dose-, Formulation- and Structure-Dependent Effect", Journal of Ocular Pharmacology and Therapeutics, 37(6):321-330, (2021).
Rigas, B. et al., "NSAID-Induced Corneal Melt: Clinical Importance, Pathogenesis, and Risk Mitigation", Survey of Opthalmology, 65:1-11, (2020).
Wen, Z. et al., "The Ocular Pharmacokinetics and Biodistribution of Phospho-Sulindac (OXT-328) Formulated in Nanoparticles: Enhanced and Targeted Tissue Drug Delivery", International Journal of Pharmaceutics, 557:273-279, (2019).

* cited by examiner

Primary Examiner — Shobha Kantamneni
(74) Attorney, Agent, or Firm — Lauren L. Stevens

(57) ABSTRACT

The invention relates to compositions and methods for treating ophthalmic conditions.

13 Claims, 18 Drawing Sheets

COMPOSITIONS AND METHODS FOR TREATING OPHTHALMIC CONDITIONS

CROSS REFERENCE TO RELATED APPLICATIONS

This application is a national phase of International Application No. PCT/US2017/054051, filed Sep. 28, 2017, which claims the benefit of priority to U.S. Provisional Application No. 62/564,595, filed Sep. 28, 2017, and U.S. Provisional Application No. 62/400,955, filed Sep. 28, 2016, the entirety of each being incorporated herein by reference.

BACKGROUND OF THE INVENTION

The eye, consisting of the eyeball and its adnexa, i.e. structures outside the eyeball, which include the orbit, eye muscles, eyelids, eyelashes, conjunctiva, and lacrimal apparatus, can be affected by many pathological conditions. Prominent among them are: a) inflammatory conditions including dry eye disease, postoperative inflammation, conjunctivitis, blepharitis, uveitis, chorioiditis, retinitis, scleritis, and keratitis; b) retinal conditions including cystoid macular edema and diabetic retinopathy; c) mechanical trauma and chemical injury to the eye; and d) miscellaneous diseases such as pterygium. Pain is a common manifestation of eye diseases often requiring topical analgesics for its control.

Dry eye disease (DED) is a common disorder, affecting about 1 in 6 humans (15% of the population), especially those older than 40 years of age. In key parts of the world there are over 600 million patients with moderate and severe DED.

Some of these individuals suffer from Sjogren's syndrome. Women of post-menopausal age comprise another segment of the dry eye population. DED may afflict individuals with differing severity. In mild cases, a patient may experience burning, a feeling of dryness, and other symptoms of ocular discomfort. In severe cases, vision may be substantially impaired.

Diseases that can cause DED include Riley-Day syndrome, Shy-Drager syndrome, Sjogren's syndrome, sarcoidosis, amyloidosis, sequelae of radiotherapy, lagophthalmia, avitaminosis A, Stevens-Johnson syndrome, ocular pemphigoid, thermal or chemical burns, drug toxicity of idoxuridine (IDU) and therapeutic agents for glaucoma, marginal blepharitis, meibomitis, sequelae of intraocular surgery, contact-lens infection, diabetic corneal epitheliopathy, dry eye due to VDT operation, and the like.

Although DED may have a variety of unrelated pathogenic causes, all share as a common effect the breakdown of the ocular tear film, with dehydration of and subsequent damage to the exposed outer ocular surfaces.

Individuals afflicted with the systemic autoimmune disease known as Sjogren's syndrome typically suffer severe dry eye. In this disease, inflammation of the lacrimal gland impairs normal secretory processes, resulting in abnormalities in the tear film. Changes to the ocular surface include the production and accumulation of a variety of mediators of inflammation.

Prior therapies for DED have included both palliative agents, such as artificial tear formulations, and drugs, such as topical corticosteroids, topical retinoids (e.g., Vitamin A), oral pilocarpine, and topical cyclosporin. In general, the palliative therapies are capable of providing short-term relief from some of the symptoms of DED, but frequent application of the palliative products to the eye is required to maintain this relief, since these products generally do not eliminate the physiological sources of the dry eye conditions. These drug therapies have had limited success in treating dry eye conditions, typically attributed to the inability of the drug to eliminate or reduce the root causes of the dry eye condition, side effects from the drugs that threaten the overall ocular health of the patient, or result in poor patient compliance, or a combination of these factors.

For example, certain glucocorticoids have a greater potential for elevating intraocular pressure ("IOP") than other compounds in this class. One such compound, prednisolone, a very potent ocular anti-inflammatory agent, has a greater tendency to elevate IOP than fluorometholone, which has moderate ocular anti-inflammatory activity. The risk of IOP elevations associated with the topical ophthalmic use of glucocorticoids increases over time. In other words, the chronic (i.e., long-term) use of these agents increases the risk of significant IOP elevations. Additionally, administering glucocorticoids in patients with eye infections may enhance the infectious damage to the eye.

Unlike bacterial infections or acute ocular inflammation associated with physical trauma, which require short-term therapy on the order of a few weeks, dry eye conditions require treatment for extended periods of time, generally several months or more. This chronic use of corticosteroids significantly increases the risk of IOP elevation. Prolonged use of corticosteroids typically increases the risk of cataract formation.

Inflammation after cataract and other types of eye surgery, which can be persistent, remains an undesirable consequence despite many advances in surgical techniques. Corticosteroids and non-steroidal anti-inflammatory drugs (NSAIDs) have traditionally been used to treat such ocular inflammation, prophylactically as well as post-operatively, However, there are significant safety concerns for both corticosteroids and NSAIDs when used to treat postoperative eye inflammation and pain.

Uveitis results from inflammation and tissue destruction of the uvea, has diverse etiologies, and can lead to serious complications. Uveitis is typically treated with corticosteroids, either as topical eye drops or as oral therapy, both of which are associated with significant side effects. The treatment of uveitis requires safe and efficacious anti-inflammatory agents.

Cystoid macular edema is retinal thickening of the macula due to a disruption of the normal blood-retinal barrier; this causes accumulation of fluid within the intracellular spaces of the retina. Visual loss occurs from retinal thickening and fluid collection that distorts the architecture of the photoreceptors. Cystoid macular edema is a leading cause of central vision loss in the developed world. The medical therapy of cystoid macular edema includes topical or systemic NSAIDs and topical, periocular, systemic or intravitreal injection or implant of corticosteroids and anti-VEGF agents, all three of which have suboptimal efficacy and significant side effects.

Conjunctivitis is inflammation or infection of the conjunctiva, and is characterized by dilatation of the conjunctival vessels, resulting in hyperemia and edema of the conjunctiva, typically with associated discharge. Infectious etiologies include viruses and bacteria. Allergic reactions are another common cause. There is a need to control the inflammation of conjunctivitis. In the case of bacterial conjunctivitis co-administration of antibiotics and anti-inflammatory agents may be required to control its clinical manifestations.

Diabetic retinopathy refers to retinal changes that occur in patients with diabetes mellitus. These changes affect the small blood vessels of the retina and can lead to vision loss through several different pathways. Indeed, diabetic retinopathy is one of the commonest causes of vision loss. Vascular endothelial growth factor (VEGF) is secreted by ischemic retina. VEGF leads to a) increased vascular permeability resulting in retinal swelling/edema and b) angiogenesis—new blood vessel formation. Agents that suppress VEGF can control diabetic retinopathy.

Pterygium is a common ocular surface lesion originating in the limbal conjunctiva within the palpebral fissure with progressive involvement of the cornea. Inflammation and hyperproliferation are likely part of its etiology. Therapeutic options for the management of pterygia range from lubrication to surgical excision. Due to the potential for recurrence and other surgical risks, the surgical removal of pterygia is not the treatment of choice. Agents with antiproliferative and anti-inflammatory properties could control this disease.

Mechanical trauma from foreign bodies, fingernails, tree branches, paper cuts, etc., is associated with pain and, depending on its etiology, with foreign body sensation, photophobia, blurred vision and lacrimation. Treatment includes, besides lubrication, antibiotics and pain relievers and in specific cases inhibitors of matrix metalloproteinase-9, and corticosteroids. Given the limited efficacy and safety of available treatments, there is a clear need for safe analgesics and alternatives to corticosteroids.

Chemical injuries to the eye have multiple etiologies. Once the inciting chemical has been completely removed, epithelial healing can begin. Inflammatory mediators released from the ocular surface at the time of injury cause tissue necrosis, neovascularization, and scarring and attract further inflammatory reactants. This inflammatory response not only inhibits re-epithelialization but also increases the risk of corneal ulceration and perforation. Controlling inflammation can break this inflammatory cycle. Topical corticosteroids are used to control inflammation, but can have significant side effects. Thus anti-inflammatory agents that are safe and can relieve pain are needed to improve current therapeutic outcomes.

There is also a lack of options for effectively delivering analgesia to patients suffering from eye pain. The pain may result from ophthalmic surgeries or other conditions. Although analgesics are typically administered acutely, rather than chronically, the doses involved are higher, and can result in side effects including corneal melt.

Accordingly, more effective ophthalmic therapies are needed.

SUMMARY OF THE INVENTION

In one aspect, the present invention provides methods of treating an ophthalmic condition in a patient, such as dry eye disease, inflammation, pain, or conjunctivitis, comprising administering to the patient a compound of Formula I:

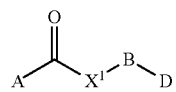

Formula I wherein the variables are as defined herein.
In preferred embodiments, the compound is administered topically, e.g., in eye drops.

In order to address the needs in the field, the invention includes compounds, compositions, and methods for treating various conditions of the eye and its associated structures (i.e., ophthalmic conditions). In some embodiments, the ophthalmic conditions treated by the compounds, compositions, and/or kits may include dry eye disease and retinopathy. In some embodiments, retinopathy may include the diseases of diabetic retinopathy, retinopathy of prematurity, VEGF retinopathy, age related macular degeneration, retinal vein occlusion, and/or hypertensive retinopathy. In certain embodiments, retinopathy may be diabetic retinopathy.

In some embodiments, the invention may include compositions, methods, or kits that comprise or use an NSAID derivative as described herein. In some embodiments, the NSAID derivative may be a compound of the invention, such as a compound of formula III or formula IV:

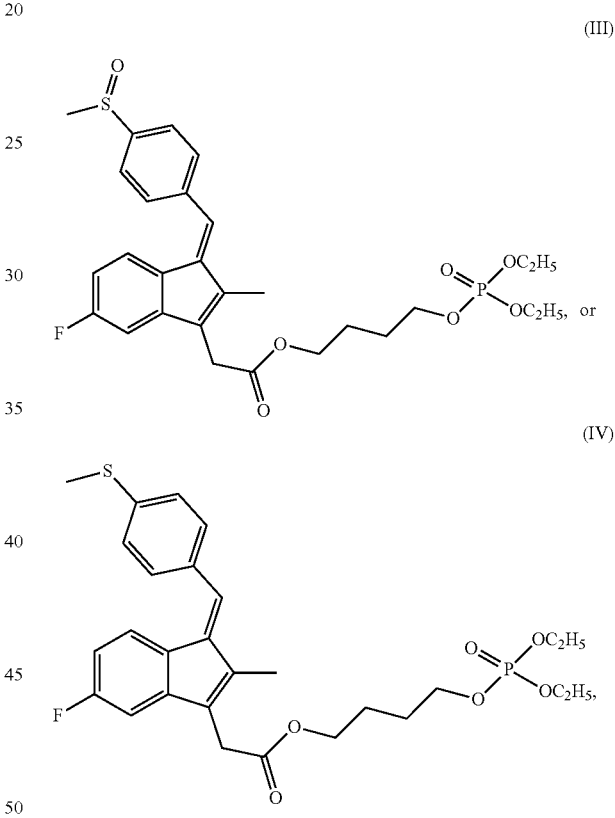

or a pharmaceutically acceptable salt thereof. The compound of formula III may be referred to as phosphosulindac (PS). The compound of formula IV may be referred to as phosphosulindac II (PS-II). The compounds of formulas III and IV are described in U.S. Pat. No. 8,236,820, the entirety of which is incorporated herein by reference.

In an embodiment, the invention includes a composition for the treatment of dry eye disease comprising a therapeutically effective amount of a compound of the invention, such as a compound of formula III or formula IV, or a pharmaceutically acceptable salt thereof, and a pharmaceutically acceptable carrier.

In an embodiment, the invention includes a composition for the treatment of dry eye disease comprising a therapeutically effective amount of a compound of the invention, such as a compound of formula III or formula IV, or a pharmaceutically acceptable salt thereof, and a therapeutically effective amount of an additional active agent, and a pharmaceutically acceptable carrier. In some embodiments, the additional active agent may include one or more of an antibiotic, cyclosporine, and lifitegrast.

In some embodiments, the invention includes a composition for the treatment of dry eye disease comprising a therapeutically effective amount of a compound of formula III, or a pharmaceutically acceptable salt thereof, and a pharmaceutically acceptable carrier.

In an embodiment, the invention includes a method for treating dry eye disease in a patient in need thereof, the method comprising administering to the patient a therapeutically effective amount of a compound of the invention, such as a compound of formula III or formula IV, or a pharmaceutically acceptable salt thereof.

In an embodiment, the invention includes a method for treating dry eye disease in a patient in need thereof, the method comprising administering to the patient a therapeutically effective amount of a compound of the invention, such as a compound of formula III or formula IV, or a pharmaceutically acceptable salt thereof, and a therapeutically effective amount of an additional active agent. In some embodiments, the additional active agent may include one or more of an antibiotic, cyclosporine, and lifitegrast.

In some embodiments, the invention includes a method for treating dry eye disease in a patient in need thereof, the method comprising administering to the patient a therapeutically effective amount of a compound of formula III, or a pharmaceutically acceptable salt thereof.

In an embodiment, the invention includes a composition for the treatment of retinopathy comprising a therapeutically effective amount of a compound of the invention, such as a compound of formula III or formula IV, or a pharmaceutically acceptable salt thereof, and a pharmaceutically acceptable carrier.

In an embodiment, the invention includes a composition for the treatment of retinopathy comprising a therapeutically effective amount of a compound of the invention, such as a compound of formula III or formula IV, or a pharmaceutically acceptable salt thereof, and a therapeutically effective amount of an additional active agent, and a pharmaceutically acceptable carrier. In some embodiments, the additional active agent may include one or more of an antibiotic, cyclosporine, and lifitegrast.

In some embodiments, the antibiotic may include one or more of tetracycline, tobramycin, chlortetracycline, bacitracin, neomycin, polymyxin, gramicidin, oxytetracycline, chloramphenicol, gentamycin, and erythromycin. Other antibiotics include aminoglycoside, ampicillin, carbenicillin, cefazolin, cephalosporin, chloramphenicol, clindamycin, everninomycin, gentamycin, kanamycin, lipopeptides, methicillin, nafcillin, novobiocia, oxazolidinones, penicillin, quinolones, rifampin, streptogramins, streptomycin, sulfamethoxazole, sulfonamide, trimethoprim, and vancomycin.

In some embodiments, the invention includes a composition for the treatment of retinopathy comprising a therapeutically effective amount of a compound of formula III, or a pharmaceutically acceptable salt thereof, and a pharmaceutically acceptable carrier.

In an embodiment, the invention includes a method for treating retinopathy in a patient in need thereof, the method comprising administering to the patient a therapeutically effective amount of a compound of the invention, such as a compound of formula III or formula IV, or a pharmaceutically acceptable salt thereof.

In an embodiment, the invention includes a method for treating retinopathy in a patient in need thereof, the method comprising administering to the patient a therapeutically effective amount of a compound of the invention, such as a compound of formula III or formula IV, or a pharmaceutically acceptable salt thereof, and a therapeutically effective amount of an additional active agent. In some embodiments, the additional active agent may include one or more of an antibiotic, cyclosporine, and lifitegrast.

In some embodiments, the invention includes a method for treating retinopathy in a patient in need thereof, the method comprising administering to the patient a therapeutically effective amount of a compound of formula III, or a pharmaceutically acceptable salt thereof.

In an embodiment, the invention includes a method of treating an ophthalmic condition in a patient in need thereof, wherein the ophthalmic condition is selected from the group consisting of dry eye disease and retinopathy, the method comprising administering to the patient a therapeutically effective amount of a compound with reduced risk of corneal melt, such as a compound of formula III or formula IV, or a pharmaceutically acceptable salt thereof.

In an embodiment, the invention includes a composition for treating an ophthalmic condition in a patient in need thereof, wherein the ophthalmic condition is selected from the group consisting of dry eye disease and retinopathy, the composition comprising a therapeutically effective amount of a compound with reduced risk of corneal melt, such as a compound of formula III or formula IV, or a pharmaceutically acceptable salt thereof, and a pharmaceutically acceptable carrier.

In an embodiment, the invention includes a composition for treating an ophthalmic condition in a patient in need thereof, wherein the ophthalmic condition is selected from the consisting of dry eye disease and retinopathy, the group composition comprising a therapeutically effective amount of a compound of the invention, such as a compound of formula III or formula IV, or a pharmaceutically acceptable salt thereof, a pharmaceutically acceptable carrier, and one or more of a solubilizing agent (e.g., vitamin E TPGS (d-α-tocopheryl polyethylene glycol 1000 succinate)), a sugar alcohol (e.g., mannitol), an acid (e.g., boric acid), and a preservative (e.g., polyquaternium-1 (polyquad)). In some embodiments, such formulations may be used to deliver a compound of the invention, such as a compound of formula III or formula IV, or a pharmaceutically acceptable salt thereof, to the retina following topical administration to the eye.

In an embodiment, the invention includes a composition for treating an ophthalmic condition in a patient in need thereof, wherein the ophthalmic condition is selected from the group consisting of dry eye disease and retinopathy, the composition comprising, by weight, about 0.5% to about 10% of a compound of the invention, such as a compound of formula III or formula IV, or a pharmaceutically acceptable salt thereof, a pharmaceutically acceptable carrier, and one or more of about 0% to about 25% vitamin E TPGS (d-α-tocopheryl polyethylene glycol 1000 succinate), about 0% to about 10% mannitol, about 0% to about 10% boric acid, and about 0% to about 1% polyquaternium-1 (polyquad).

In an embodiment, the invention includes a composition for treating an ophthalmic condition in a patient in need thereof, wherein the ophthalmic condition is selected from the group consisting of dry eye disease and retinopathy, the composition comprising, by weight, greater than 0.5% of a compound of the invention, such as a compound of formula III or formula IV, or a pharmaceutically acceptable salt thereof, a pharmaceutically acceptable carrier, and one or more of greater than 5% vitamin E TPGS (d-α-tocopheryl polyethylene glycol 1000 succinate), greater than 0.5% mannitol, greater than 0.5% boric acid, and greater than 0.001% polyquaternium-1 (polyquad).

In an embodiment, the invention includes a composition for treating an ophthalmic condition in a patient in need thereof, wherein the ophthalmic condition is selected from the group consisting of dry eye disease and retinopathy, the composition comprising, by weight, less than 10% of a compound of the invention, such as a compound of formula III or formula IV, or a pharmaceutically acceptable salt thereof, a pharmaceutically acceptable carrier, and one or more of less than 25% vitamin E TPGS (d-α-tocopheryl polyethylene glycol 1000 succinate), less than 10% mannitol, less than 10% boric acid, and less than 1% polyquaternium-1 (polyquad).

In an embodiment, the invention includes a composition for treating an ophthalmic condition in a patient in need thereof, wherein the ophthalmic condition is selected from the group consisting of dry eye disease and retinopathy, the composition comprising, by weight, about 3.5% of a compound of the invention, such as a compound of formula III or formula IV, or a pharmaceutically acceptable salt thereof, a pharmaceutically acceptable carrier, and one or more of about 16% vitamin E TPGS (d-α-tocopheryl polyethylene glycol 1000 succinate), about 3.18% mannitol, about 1.2% boric acid, and about 0.005% polyquaternium-1 (polyquad).

In an embodiment, the invention includes a composition for treating an ophthalmic condition in a patient in need thereof, wherein the ophthalmic condition is selected from the group consisting of dry eye disease and retinopathy, the composition comprising a therapeutically effective amount of a compound of the invention, such as a compound of formula III or formula IV, or a pharmaceutically acceptable salt thereof, a pharmaceutically acceptable carrier, and one or more of a gelling excipient (e.g., gellan gum or sodium alginate), a poloxamer, a solubilizing agent (e.g., vitamin E TPGS), a surfactant, a polyether, and a cyclodextrin (e.g., (2-hydroxypropyl)-β-cyclodextrin). In some embodiments, such formulations may allow for delivery of a compound of the invention, such as a compound of formula III or formula IV, or a pharmaceutically acceptable salt thereof, to anterior segments of the eye following topical administration.

In an embodiment, the invention includes a composition for treating an ophthalmic condition in a patient in need thereof, wherein the ophthalmic condition is selected from the group consisting of dry eye disease and retinopathy, the composition comprising a therapeutically effective amount of a compound of the invention, such as a compound of formula III or formula IV, or a pharmaceutically acceptable salt thereof, a pharmaceutically acceptable carrier, and one or more of gellan gum, vitamin E TPGS, and a (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, about 0.5% to about 10% of a compound of the invention, such as a compound of formula III or formula IV, or a pharmaceutically acceptable salt thereof, a pharmaceutically acceptable carrier, and one or more of about 0% to about 5% gellan gum, about 0% to about 20% vitamin E TPGS, and about 0% to about 20% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, greater than 0.5% of a compound of the invention, such as a compound of formula III or formula IV, or a pharmaceutically acceptable salt thereof, a pharmaceutically acceptable carrier, and one or more of greater than 0.1% gellan gum, greater than 1% vitamin E TPGS, and greater than 5% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, less than 20% of a compound of the invention, such as a compound of formula III or formula IV, or a pharmaceutically acceptable salt thereof, a pharmaceutically acceptable carrier, and one or more of less than 5% gellan gum, less than 20% vitamin E TPGS, less than 20% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, about 2.4% to about 3% of a compound of the invention, such as a compound of formula III or formula IV, or a pharmaceutically acceptable salt thereof, a pharmaceutically acceptable carrier, and one or more of about 0.5% gellan gum, about 5% vitamin E TPGS, about 10% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, about 2.4% to about 3% of a compound of the invention, such as a compound of formula III or formula IV, or a pharmaceutically acceptable salt thereof, a pharmaceutically acceptable carrier, and one or more of about 0.4% gellan gum, about 10% vitamin E TPGS, about 5% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising a therapeutically effective amount of a compound of the invention, such as a compound of formula III or formula IV, or a pharmaceutically acceptable salt thereof, a pharmaceutically acceptable carrier, and one or more of sodium alginate, vitamin E TPGS, a (2-hydroxypropyl)-β-cyclodextrin, Tween (e.g., Tween 80), poly(ethylene glycol) (PEG) (e.g., PEG 400), and polyoxyl stearate.

In an embodiment, the invention includes a composition for treating an ophthalmic condition in a patient in need thereof, wherein the ophthalmic condition is selected from the group consisting of dry eye disease and retinopathy, the composition comprising, by weight, about 0.5% to about 10% of a compound of the invention, such as a compound of formula III or formula IV, or a pharmaceutically acceptable salt thereof, a pharmaceutically acceptable carrier, and one or more of about 0% to about 5% sodium alginate, about 0% to about 20% vitamin E TPGS, and about 0% to about 20% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, greater than 0.5% of a compound of the invention, such as a compound of formula III or formula IV, or a pharmaceutically acceptable salt thereof, a pharmaceutically acceptable carrier, and one or more of greater than 0.1% sodium alginate, greater than 1% vitamin E TPGS, and greater than 5% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, less than 10% of a compound of the invention, such as a compound of formula III or formula IV, or a pharmaceutically acceptable salt thereof, a pharmaceutically acceptable carrier, and one or more of less than 5% sodium alginate, less than 20% vitamin E TPGS, less than 20% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, about 3% of a compound of the invention, such as a compound of formula III or formula IV, or a pharmaceutically acceptable salt thereof, a pharmaceutically acceptable carrier, and one or more of about 1.5% sodium alginate, about 5% vitamin E TPGS, about 10% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, about 0.5% to about 10% of a compound of the invention, such as a compound of formula III or formula IV, or a pharmaceutically acceptable salt thereof, a pharmaceutically acceptable carrier, and one or more of about 0% to about 5% sodium alginate, about 0% to about 25% Tween 80, about 0% to about 20% (2-hydroxylpropyl)-β-cyclodextrin, about 0% to about 20% PEG 400, and about 0% to about 10% polyoxyl stearate.

In an embodiment, the invention includes a composition for treating an ophthalmic condition in a patient in need thereof, wherein the ophthalmic condition is selected from the group consisting of dry eye disease and retinopathy, the composition comprising, by weight, greater than 0.5% of a compound of the invention, such as a compound of formula III or formula IV, or a pharmaceutically acceptable salt thereof, a pharmaceutically acceptable carrier, and one or more of greater than 1% sodium alginate, greater than 1% Tween 80, greater than 1% (2-hydroxylpropyl)-β-cyclodextrin, greater than 1% PEG 400, and greater than 1% polyoxyl stearate.

In an embodiment, the invention includes a composition for treating an ophthalmic condition in a patient in need thereof, wherein the ophthalmic condition is selected from the group consisting of dry eye disease and retinopathy, the composition comprising, by weight, less than 10% of a compound of the invention, such as a compound of formula III or formula IV, or a pharmaceutically acceptable salt thereof, a pharmaceutically acceptable carrier, and one or more of less than 5% sodium alginate, less than 25% Tween 80, less than 20% (2-hydroxylpropyl)-β-cyclodextrin, less than 20% PEG 400, and less than 10% polyoxyl stearate.

In an embodiment, the invention includes a composition for treating an ophthalmic condition in a patient in need thereof, wherein the ophthalmic condition is selected from the group consisting of dry eye disease and retinopathy, the composition comprising, by weight, 3% of a compound of the invention, such as a compound of formula III or formula IV, or a pharmaceutically acceptable salt thereof, a pharmaceutically acceptable carrier, and one or more of about 1.5% sodium alginate, about 15% Tween 80, about 10% (2-hydroxylpropyl)-β-cyclodextrin, about 10% PEG 400, and about 5% polyoxyl stearate.

In an embodiment, the invention includes a composition for treating an ophthalmic condition in a patient in need thereof, wherein the ophthalmic condition is selected from the group consisting of dry eye disease and retinopathy, the composition comprising, by weight, about 1% to about 5% of a compound of the invention, such as a compound of formula III or formula IV, or a pharmaceutically acceptable salt thereof, a pharmaceutically acceptable carrier, and one or more of about 50% to about 90% (2-hydroxypropyl)-β-cyclodextrin (HP-β-CD), about 0.05% to about 1% cremophor EL (F1), and about 0.5% to about 5% Tween 80 (F2).

In an embodiment, the invention includes a composition for treating an ophthalmic condition in a patient in need thereof, wherein the ophthalmic condition is selected from the group consisting of dry eye disease and retinopathy, the composition comprising, by weight, about 1% to about 5% of a compound of the invention, such as a compound of formula III or formula IV, or a pharmaceutically acceptable salt thereof, a pharmaceutically acceptable carrier, and one or more of about 50% to about 90% (2-hydroxypropyl)-β-cyclodextrin (HP-β-CD), and about 0.05% to about 1% cremophor EL (F1).

In an embodiment, the invention includes a composition for treating an ophthalmic condition in a patient in need thereof, wherein the ophthalmic condition is selected from the group consisting of dry eye disease and retinopathy, the composition comprising, by weight, about 1% to about 5% of a compound of the invention, such as a compound of formula III or formula IV, or a pharmaceutically acceptable salt thereof, a pharmaceutically acceptable carrier, and one or more of about 50% to about 90% (2-hydroxypropyl)-β-cyclodextrin (HP-β-CD), and about 0.5% to about 5% Tween 80 (F2).

In an embodiment, the invention includes a composition for treating an ophthalmic condition in a patient in need thereof, wherein the ophthalmic condition is selected from the group consisting of dry eye disease and retinopathy, the composition comprising, by weight, about 3% to about 4% of a compound of the invention, such as a compound of formula III or formula IV, or a pharmaceutically acceptable salt thereof, a pharmaceutically acceptable carrier, and one or more of about 80% (2-hydroxypropyl)-β-cyclodextrin (HP-β-CD), and about 0.1% cremophor EL (F1).

In an embodiment, the invention includes a composition for treating an ophthalmic condition in a patient in need thereof, wherein the ophthalmic condition is selected from the group consisting of dry eye disease and retinopathy, the composition comprising, by weight, about 3% to about 4% of a compound of the invention, such as a compound of formula III or formula IV, or a pharmaceutically acceptable salt thereof, a pharmaceutically acceptable carrier, and one or more of about 80% (2-hydroxypropyl)-β-cyclodextrin (HP-β-CD), and about 1% Tween 80 (F2).

In an embodiment, the invention includes a composition for treating an ophthalmic condition in a patient in need thereof, wherein the ophthalmic condition is selected from the group consisting of dry eye disease and retinopathy, the composition comprising, by weight, about 1% to about 10% of a compound of the invention, such as a compound of formula III or formula IV, or a pharmaceutically acceptable salt thereof, a pharmaceutically acceptable carrier, and one or more of about 1% to about 40% Poloxamer 407 and about 1% to about 20% vitamin E TPGS.

In an embodiment, the invention includes a composition for treating an ophthalmic condition in a patient in need thereof, wherein the ophthalmic condition is selected from the group consisting of dry eye disease and retinopathy, the composition comprising, by weight, greater than 1% of a compound of the invention, such as a compound of formula III or formula IV, or a pharmaceutically acceptable salt thereof, a pharmaceutically acceptable carrier, and one or more of greater than 1% Poloxamer 407 and greater than 1% vitamin E TPGS.

In an embodiment, the invention includes a composition for treating an ophthalmic condition in a patient in need thereof, wherein the ophthalmic condition is selected from the group consisting of dry eye disease and retinopathy, the composition comprising, by weight, less than 10% of a compound of the invention, such as a compound of formula III or formula IV, or a pharmaceutically acceptable salt thereof, a pharmaceutically acceptable carrier, and one or more of less than 40% Poloxamer 407 and less than 20% vitamin E TPGS.

In an embodiment, the invention includes a composition for treating an ophthalmic condition in a patient in need thereof, wherein the ophthalmic condition is selected from the group consisting of dry eye disease and retinopathy, the composition comprising, by weight, about 5.4% of a compound of the invention, such as a compound of formula III or formula IV, or a pharmaceutically acceptable salt thereof, a pharmaceutically acceptable carrier, and one or more of about 20% Poloxamer 407 and about 12% vitamin E TPGS.

In an embodiment, the invention includes a composition for treating an ophthalmic condition in a patient in need thereof, wherein the ophthalmic condition is selected from the group consisting of dry eye disease and retinopathy, the composition comprising a nanoparticle formulation comprising a compound of the invention, such as a compound of formula III or formula IV, or a pharmaceutically acceptable salt thereof, and a pharmaceutically acceptable carrier. In some embodiments, the nanoparticle formulation may include poly(ethylene glycol) (PEG) nanoparticles. In some embodiments, the nanoparticle formulation may include methoxy poly(ethylene glycol)-poly(lactide) (mPEG-PLA) nanoparticles. In some embodiments, such formulations may allow for delivery of PS to anterior segments of the eye following topical administration.

In an embodiment, the invention includes a composition for treating an ophthalmic condition in a patient in need thereof, wherein the ophthalmic condition is selected from the group consisting of dry eye disease and retinopathy, the composition comprising a nanoparticle formulation comprising, by weight, about 1% to about 5% a compound of the invention, such as a compound of formula III or formula IV, or a pharmaceutically acceptable salt thereof, a pharmaceutically acceptable carrier, and about 90% to about 98% mPEG-PLA.

In an embodiment, the invention includes a composition for treating an ophthalmic condition in a patient in need thereof, wherein the ophthalmic condition is selected from the group consisting of dry eye disease and retinopathy, the composition comprising a nanoparticle formulation comprising, by weight, about 3% to about 3.5% a compound of the invention, such as a compound of formula III or formula IV, or a pharmaceutically acceptable salt thereof, a pharmaceutically acceptable carrier, and about 96.5% to about 97% mPEG-PLA.

In some embodiments, the compounds of formula III and/or formula IV are analgesic agents.

In some embodiments, the compounds of formula III and/or formula IV are anti-inflammatory agents.

In some embodiments, the compounds of formula III and/or formula IV have a reduced risk of corneal melt or do not result in corneal melt upon administration to the eye.

BRIEF DESCRIPTION OF THE FIGURES

In FIG. 6A, NF-κB activation was determined by EMSA in cultured human conjunctival cells stimulated with TNFα (top) and in the ILG of rabbits with Con A-induced DED and treated for one week with either vehicle or PS (bottom). In FIG. 6B, immunoblots detecting the activation of MAPKs by phosphorylation in cultured human conjunctival cells treated with PS at the indicated concentrations for 3.5 h. Loading control: β-actin.

In FIG. 7A, human conjunctival cells were treated for 24 h with PS at $1 \times IC_{50}$ (TNF-α was added to the culture medium at a concentration of 10 ng/ml 2 h after PS). Cytokine levels were determined by ELISA and represent the average of a three samples. In FIG. 7B, IL-1β and IL-8 levels were determined by ELISA in the lacrimal glands of rabbits with Con A-induced DED that were treated with vehicle or PS for one week as previously. Gland tissue was homogenized and ELISA was performed on whole-tissue lysates. n=8 glands/group. Values=mean±SEM.

In FIG. 8A, the human conjunctival cells were treated with PS at 1×IC$_{50}$ (TNF-α was added to the culture medium at a concentration of 10 ng/ml 2 h after PS. The levels of MMP-1 in the culture medium were determined by ELISA as in Methods (n=3). Values=mean±SEM. In FIG. 8B, two groups of rabbits with Con A-induced DED were treated with vehicle or PS for 1 week as in Methods. Naïve rabbits served as controls. MMP-9 levels in the ILG (top) and the aqueous humor (middle) were determined by ELISA. MMP activity was determined in the cornea of naïve and PS- or ketorolac-treated rabbits with Con A-induced DED as previously. n=8 eyes/group. Values=mean±SEM.

In FIG. 9A, PGE$_2$ levels were determined by ELISA in tears collected on day 7 from naïve rabbits and rabbits with Con A-induced DED treated for 1 week with vehicle or PS. In FIG. 9B, PGE$_2$ levels were further examined. Upper panel: PGE$_2$ levels in the tears of naïve rabbits and rabbits with Con A-induced DED treated for 1 h with PS or ketorolac as in Methods. Lower panel: PGE$_2$ levels in the corneal tissue of naïve rabbits and rabbits with Con A-induced DED treated for 1 week with vehicle or PS or ketorolac or diclofenac. n=8 eyes/group. Values=mean±SEM.

DETAILED DESCRIPTION

Figure 1:
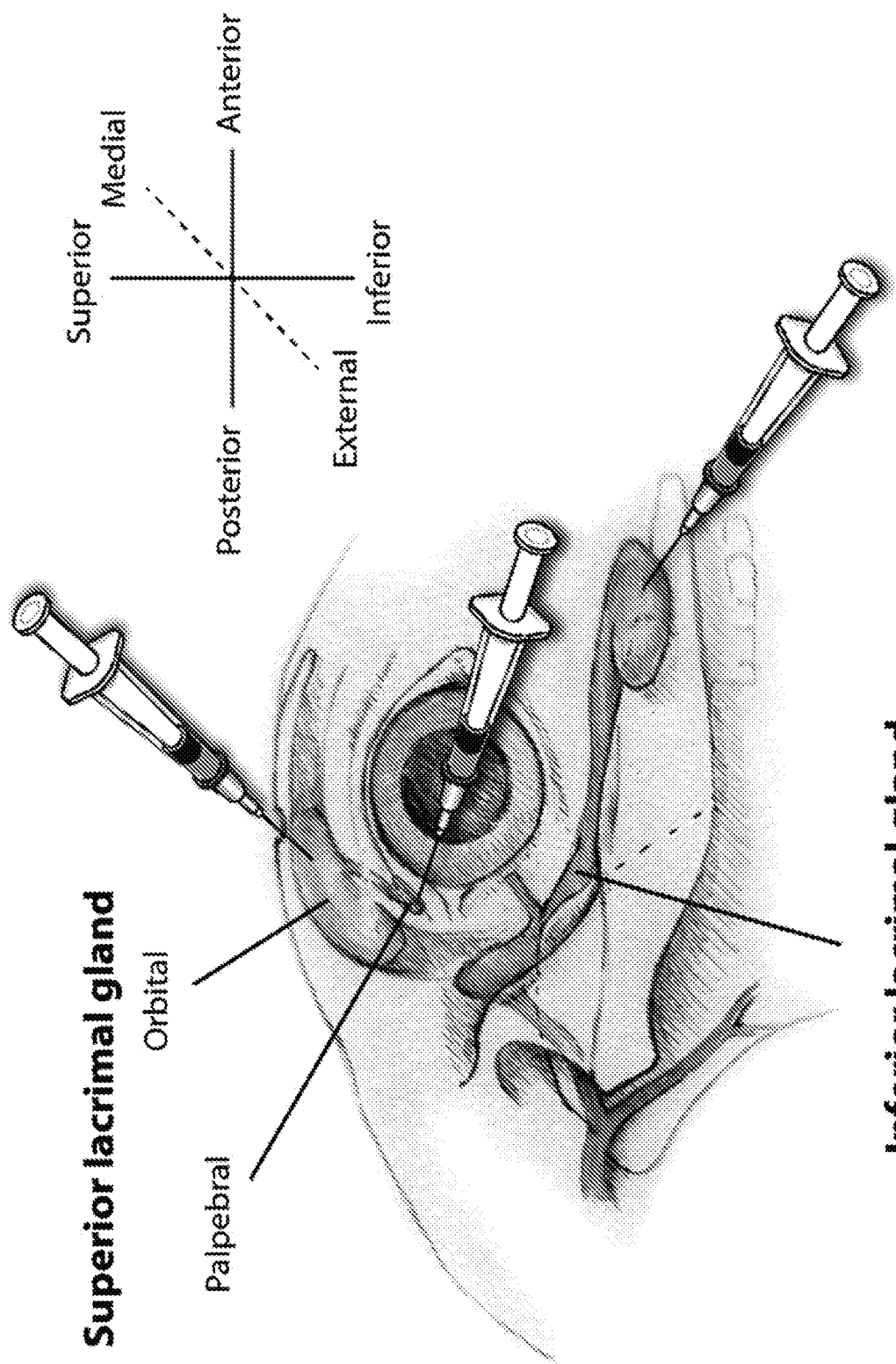
FIG. 1 illustrates the injection sites to the rabbit eye. The right eye of the rabbit and its two lacrimal glands are depicted along with the sites where Con A is administered. Part of the ILG is underneath the zygomatic bone. Upper right: orientation coordinates.

In some embodiments, the present invention provides a method of treating an ophthalmic condition, such as dry eye, inflammation, pain, or conjunctivitis, in a patient, comprising administering to the patient a compound of Formula I:

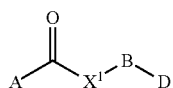

Formula I or a salt thereof. In Formula I:
$X^1$ is selected from —O—, —S— and —NR$^1$—;
$R^1$ is H or C$_{1-10}$-alkyl;
A is selected from phenyl,

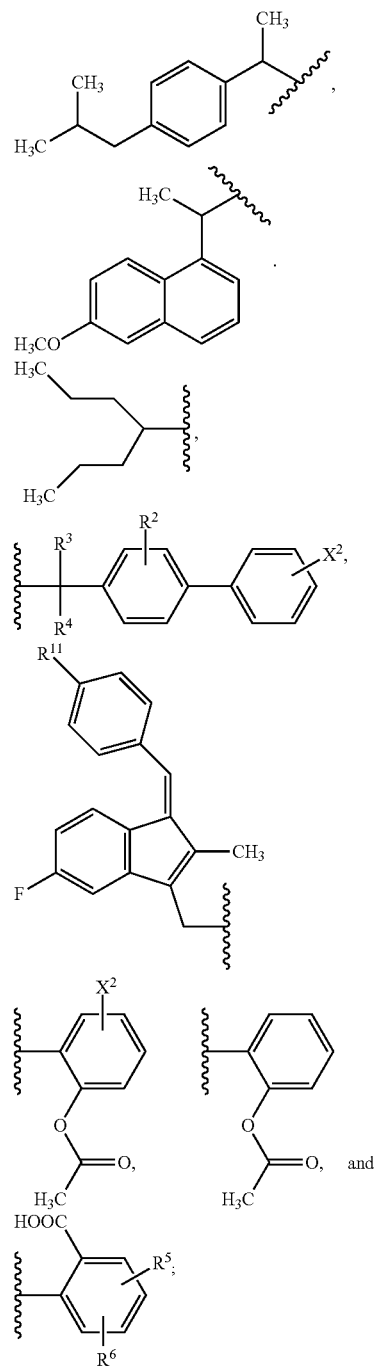

$R^2$ is a halogen atom;
each of $R^3$ and $R^4$ is, independently, hydrogen or alkyl;

each of $R^5$ and $R^6$ is, independently, hydrogen, —OH, alkoxy, halo, trifluoroalkyl, haloalkyl, trifluoroalkoxy, alkyl, cycloalkyl, heteroalkyl, heterocyclyl, aryl, aralkyl, heteroaryl or heteroaralkyl;

$R^{11}$ is —SCH$_3$, —S(O)CH$_3$ or —S(O)$_2$CH$_3$;

B is unsubstituted alkyl, cycloalkyl, heteroalkyl, heterocyclyl, aryl, aralkyl, heteroaryl, or heteroaralkyl or is alkyl, cycloalkyl, heteroalkyl, heterocyclyl, aryl, aralkyl, heteroaryl, or heteroaralkyl substituted with one or more $X^2$;

each $X^2$ is independently selected from hydrogen, halogen, hydroxyl, alkoxy, —CN, alkyl, cycloalkyl, heteroalkyl, heterocyclyl, aryl, aralkyl, heteroaryl, heteroaralkyl, —OR$^R$, —SO$_2$R$^d$, —NR$^b$R$^c$, —C(=O)R$^a$, —C(=O)OR$^a$, or

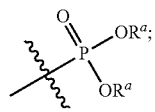

$R^a$, for each occurrence, is independently selected from hydrogen, alkyl, cycloalkyl, heteroalkyl, heterocyclyl, aryl, aralkyl, heteroaryl, or heteroaralkyl;

$R^b$ and $R^c$, for each occurrence, are independently selected from hydrogen, hydroxy, SO$_2$R$^d$, alkyl, cycloalkyl, heteroalkyl, heterocyclyl, aryl, aralkyl, heteroaryl, or heteroaralkyl;

$R^d$, for each occurrence, is independently selected from hydrogen, —N(R$^e$)$_2$, alkyl, cycloalkyl, heteroalkyl, heterocyclyl, aryl, aralkyl, heteroaryl, or heteroaralkyl;

$R^R$ is alkyl, cycloalkyl, heteroalkyl, heterocyclyl, aryl, aralkyl, heteroaryl, heteroaralkyl, or acyl; and D is

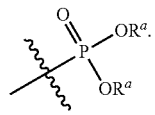

In some embodiments, each of $R^3$, $R^4$, $R^5$, and $R^6$ is hydrogen, halo, $C_1$-$C_6$ alkyl or $C_1$-$C_6$ cycloalkyl.

In some preferred embodiments, A is selected from:

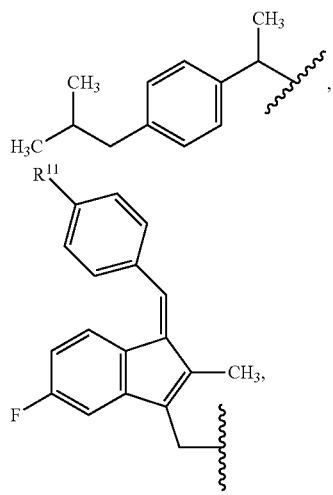

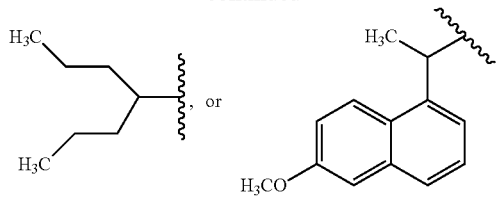

In some embodiments, B is

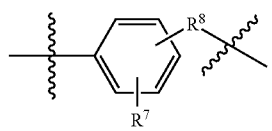

or a $C_1$-$C_{10}$ alkylene; wherein $R^7$ is $C_1$-$C_3$ alkyl, preferably methyl; and $R^8$ is H, $C_1$-$C_3$ alkyl, $C_1$-$C_3$ alkoxy, or halo, preferably H.

In some preferred embodiments, B is —(CH$_2$)$_4$—.

In some embodiments, $X^2$ is

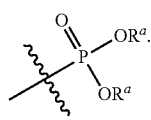

In preferred embodiments, both $R^a$ substituents on $X^2$ are identical. Preferably, both $R^a$ substituents on $X^2$ are alkyl groups having 1 to 3 carbon atoms. In some particularly preferred embodiments, both $R^a$ substituents on $X^2$ are ethyl groups.

In certain preferred embodiments, both $R^a$ substituents on D are identical. Preferably, both $R^a$ substituents on D are alkyl groups having 1 to 3 carbon atoms. In some particularly preferred embodiments, both $R^a$ substituents on D are ethyl groups.

In some embodiments of the invention, A is:

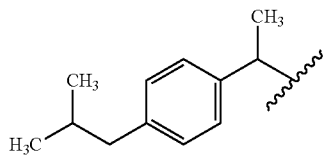

In some embodiments of the invention, A is:

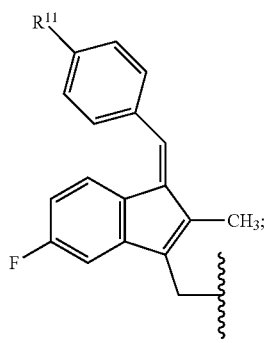

wherein $R^{11}$ is —SCH$_3$, —S(O)CH$_3$ or —S(O)$_2$CH$_3$, preferably S(O)CH$_3$.

In some embodiments, the compound of formula I is phospho-sulindac I (PS) or phospho-sulindac II (PS-II):

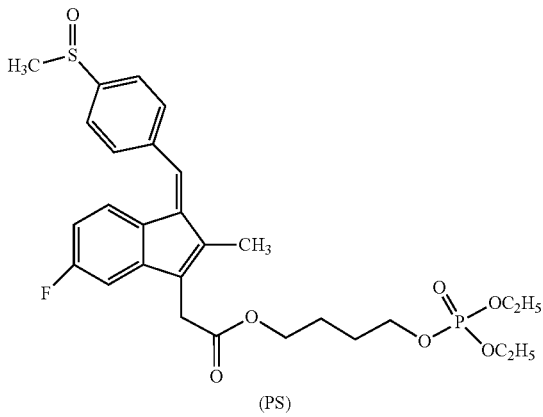
(PS)

or

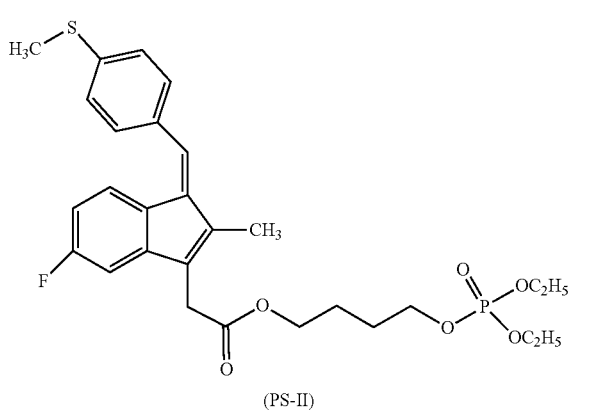
(PS-II)

In some preferred embodiments, the compound of formula I is PS.

In some embodiments of the invention, A is:

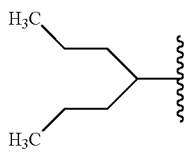

In some embodiments, the compound of formula I is phosphovalproic acid:

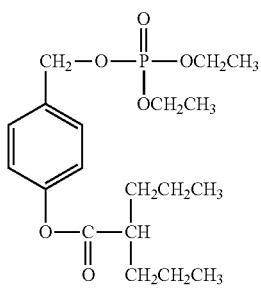

In some embodiments, the present invention provides a method of treating an ophthalmic condition, such as dry eye, inflammation, pain, or conjunctivitis, in a patient, comprising administering to the patient one or more of the compounds disclosed in US2009/0099137A1, US2013/0225529A1, and US2014/0315834, the contents of each of which are fully incorporated by reference herein in their entireties.

In some embodiments, the present invention provides a method of treating an ophthalmic condition, such as dry eye, inflammation, pain, or conjunctivitis, in a patient, comprising administering to the patient a compound of Formula II:

A-D-Y     Formula II or a salt thereof. In Formula II:

A is selected from A1-A38:

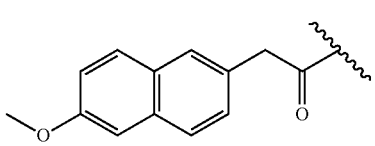
A1

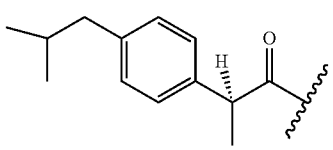
A2

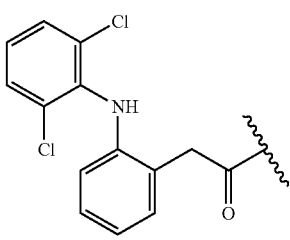
A3

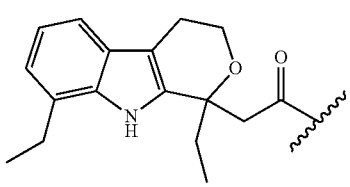
A4

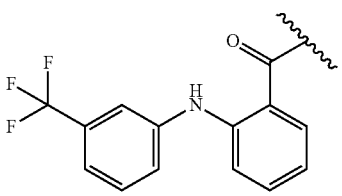
A5

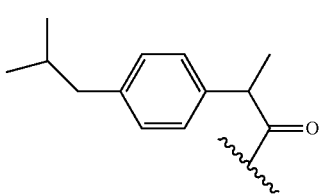
A6

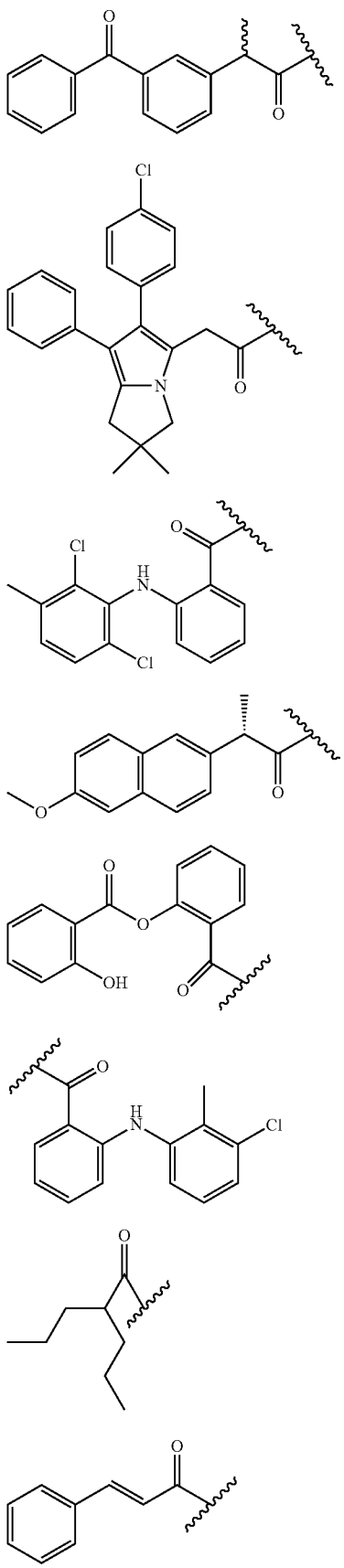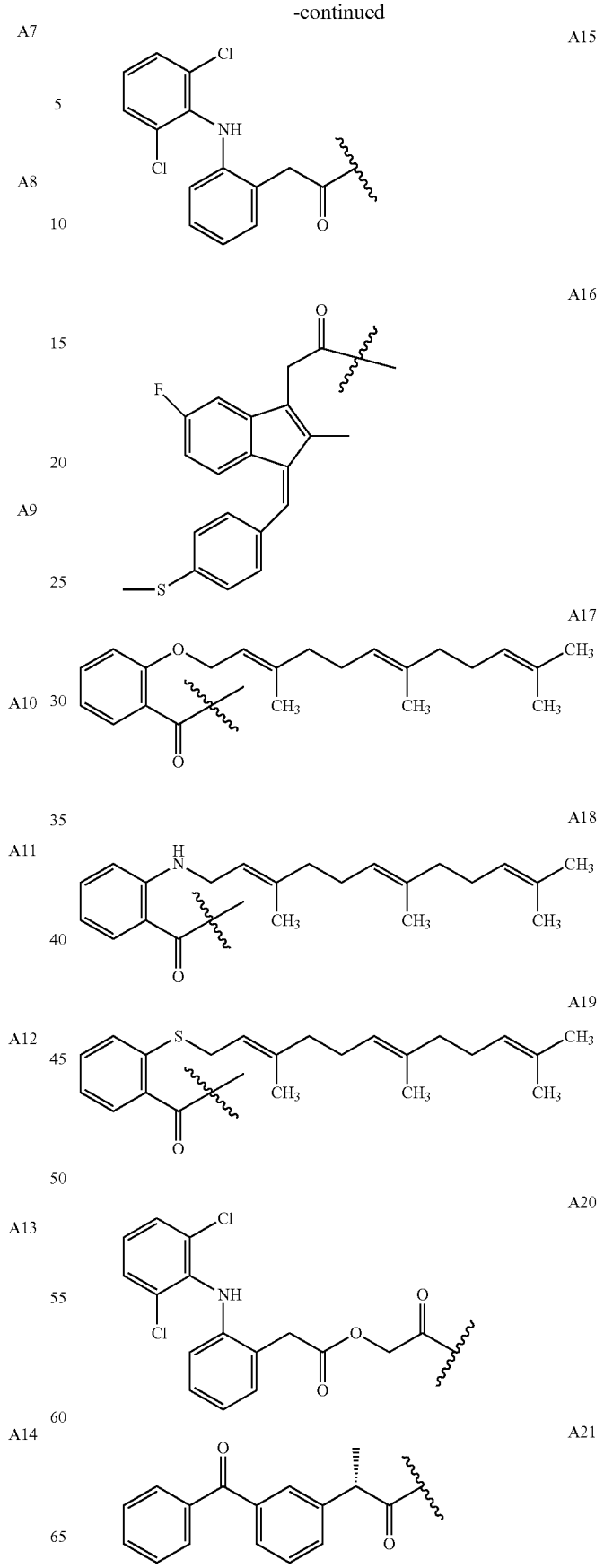

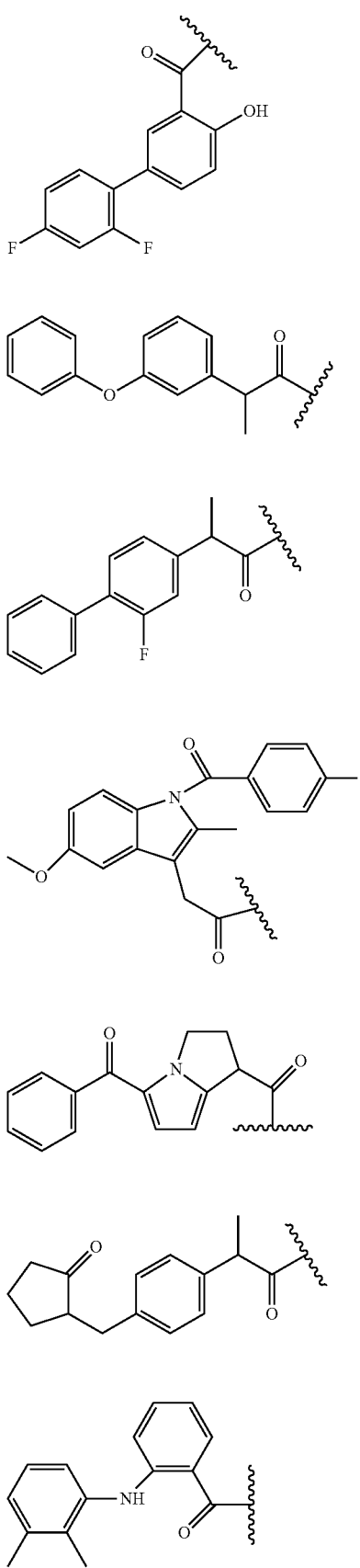
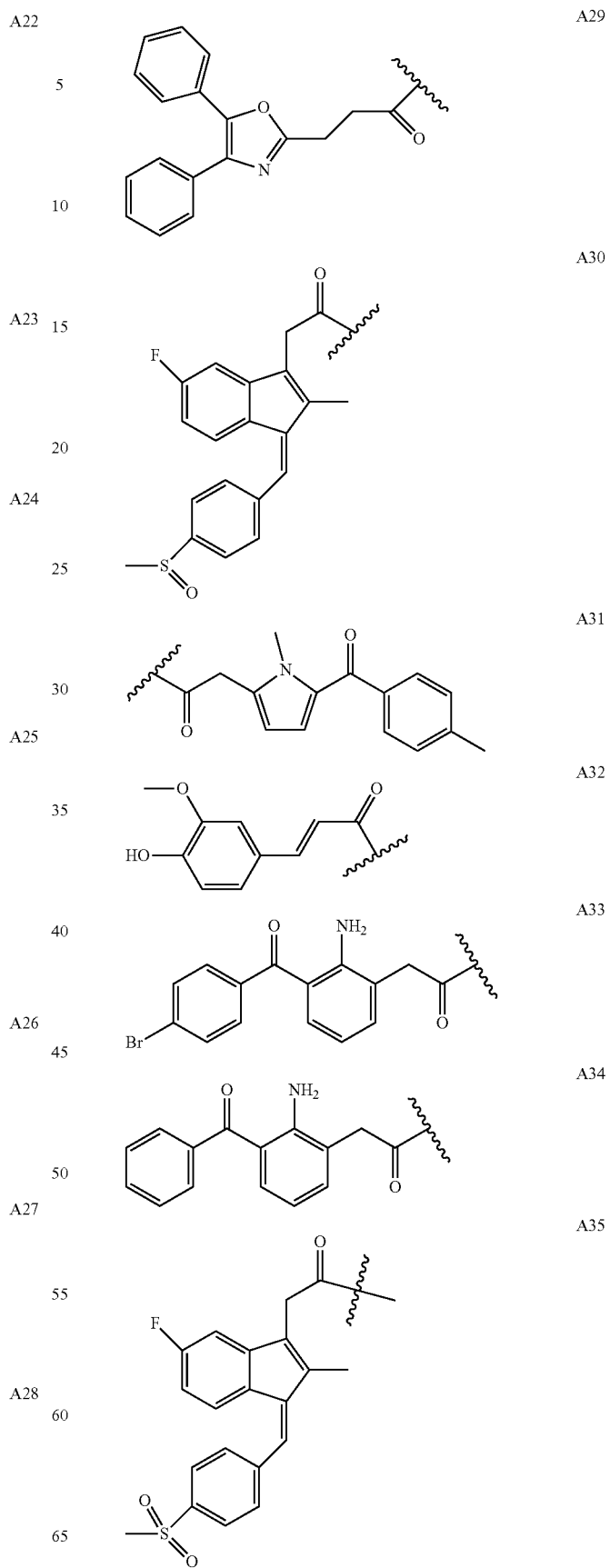

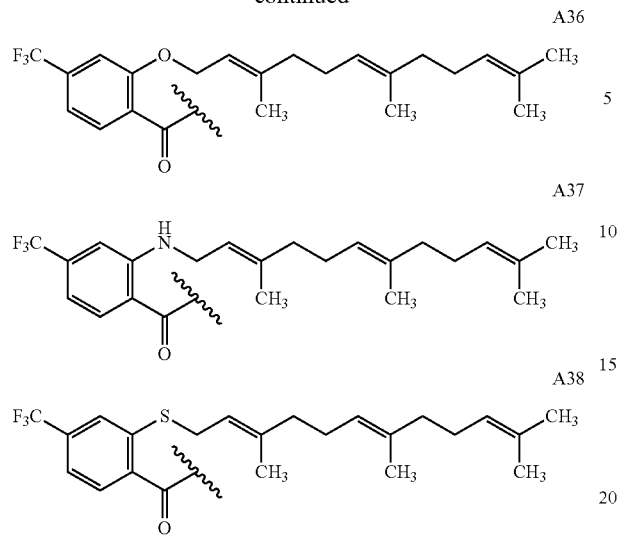

D is selected from D1-D10:

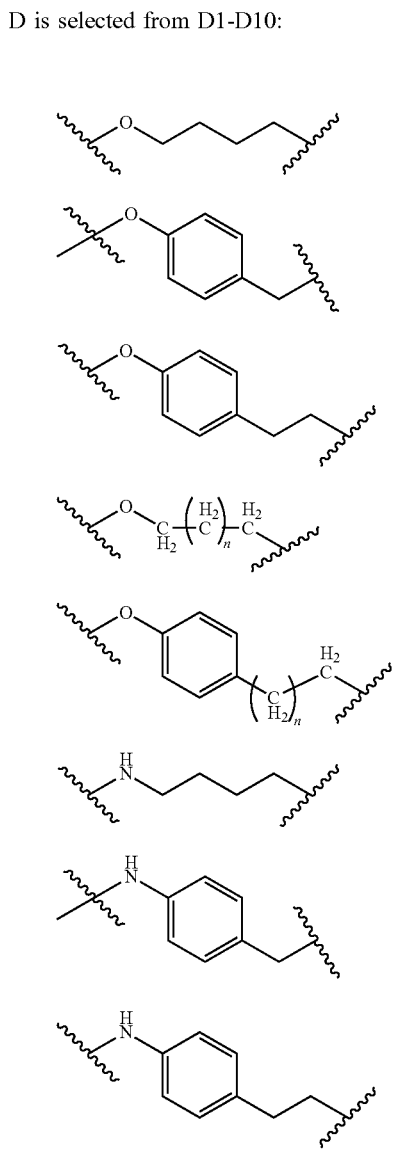

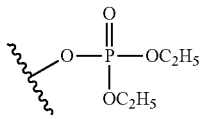

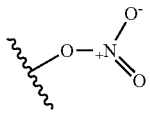

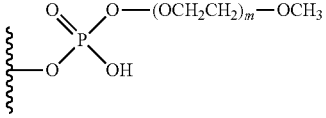

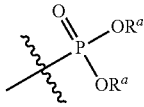

n=0-10 and preferably 1-6.
Y is selected from Y1-Y4:

where m=1-100 and preferably 30-50; and $R^a$, for each occurrence, is independently selected from hydrogen, alkyl, cycloalkyl, heteroalkyl, heterocyclyl, aryl, aralkyl, heteroaryl, or heteroaralkyl;

The following table lists exemplary compounds of Formula II:

| Compound No. | Compound Structure |
|---|---|
| 1 | A16-D1-Y1 |
| 2 | A16-D1-Y2 |
| 3 | A16-D1-Y3 |
| 4 | A16-D1-Y4 |
| 5 | A30-D1-Y1 |
| 6 | A30-D1-Y2 |
| 7 | A30-D1-Y3 |
| 8 | A30-D1-Y4 |
| 9 | A35-D1-Y1 |
| 10 | A35-D1-Y2 |
| 11 | A35-D1-Y3 |
| 12 | A35-D1-Y4 |
| 13 | A16-D2-Y1 |
| 14 | A16-D2-Y2 |
| 15 | A16-D2-Y3 |
| 16 | A16-D2-Y4 |
| 17 | A30-D2-Y1 |
| 18 | A30-D2-Y2 |
| 19 | A30-D2-Y3 |
| 20 | A30-D2-Y4 |
| 21 | A35-D2-Y1 |

-continued

| Compound No. | Compound Structure |
|---|---|
| 22 | A35-D2-Y2 |
| 23 | A35-D2-Y3 |
| 24 | A35-D2-Y4 |
| 25 | A16-D3-Y1 |
| 26 | A16-D3-Y2 |
| 27 | A16-D3-Y3 |
| 28 | A16-D3-Y4 |
| 29 | A30-D3-Y1 |
| 30 | A30-D3-Y2 |
| 31 | A30-D3-Y3 |
| 32 | A30-D3-Y4 |
| 33 | A35-D3-Y1 |
| 34 | A35-D3-Y2 |
| 35 | A35-D3-Y3 |
| 36 | A35-D3-Y4 |
| 37 | A16-D4-Y1 |
| 38 | A16-D4-Y2 |
| 39 | A16-D4-Y3 |
| 40 | A16-D4-Y4 |
| 41 | A30-D4-Y1 |
| 42 | A30-D4-Y2 |
| 43 | A30-D4-Y3 |
| 44 | A30-D4-Y4 |
| 45 | A35-D4-Y1 |
| 46 | A35-D4-Y2 |
| 47 | A35-D4-Y3 |
| 48 | A35-D4-Y4 |
| 49 | A16-D5-Y1 |
| 50 | A16-D5-Y2 |
| 51 | A16-D5-Y3 |
| 52 | A16-D5-Y4 |
| 53 | A30-D5-Y1 |
| 54 | A30-D5-Y2 |
| 55 | A30-D5-Y3 |
| 56 | A30-D5-Y4 |
| 57 | A35-D5-Y1 |
| 58 | A35-D5-Y2 |
| 59 | A35-D5-Y3 |
| 60 | A35-D5-Y4 |
| 61 | A16-D6-Y1 |
| 62 | A16-D6-Y2 |
| 63 | A16-D6-Y3 |
| 64 | A16-D6-Y4 |
| 65 | A30-D6-Y1 |
| 66 | A30-D6-Y2 |
| 67 | A30-D6-Y3 |
| 68 | A30-D6-Y4 |
| 69 | A35-D6-Y1 |
| 70 | A35-D6-Y2 |
| 71 | A35-D6-Y3 |
| 72 | A35-D6-Y4 |
| 73 | A16-D7-Y1 |
| 74 | A16-D7-Y2 |
| 75 | A16-D7-Y3 |
| 76 | A16-D7-Y4 |
| 77 | A30-D7-Y1 |
| 78 | A30-D7-Y2 |
| 79 | A30-D7-Y3 |
| 80 | A30-D7-Y4 |
| 81 | A35-D7-Y1 |
| 82 | A35-D7-Y2 |
| 83 | A35-D7-Y3 |
| 84 | A35-D7-Y4 |
| 85 | A16-D8-Y1 |
| 86 | A16-D8-Y2 |
| 87 | A16-D8-Y3 |
| 88 | A16-D8-Y4 |
| 89 | A30-D8-Y1 |
| 90 | A30-D8-Y2 |
| 91 | A30-D8-Y3 |
| 92 | A30-D8-Y4 |
| 93 | A35-D8-Y1 |
| 94 | A35-D8-Y2 |
| 95 | A35-D8-Y3 |
| 96 | A35-D8-Y4 |
| 97 | A16-D9-Y1 |
| 98 | A16-D9-Y2 |
| 99 | A16-D9-Y3 |
| 100 | A16-D9-Y4 |
| 101 | A30-D9-Y1 |
| 102 | A30-D9-Y2 |
| 103 | A30-D9-Y3 |
| 104 | A30-D9-Y4 |
| 105 | A35-D9-Y1 |
| 106 | A35-D9-Y2 |
| 107 | A35-D9-Y3 |
| 108 | A35-D9-Y4 |
| 109 | A16-D10-Y1 |
| 110 | A16-D10-Y2 |
| 111 | A16-D10-Y3 |
| 112 | A16-D10-Y4 |
| 113 | A30-D10-Y1 |
| 114 | A30-D10-Y2 |
| 115 | A30-D10-Y3 |
| 116 | A30-D10-Y4 |
| 117 | A35-D10-Y1 |
| 118 | A35-D10-Y2 |
| 119 | A35-D10-Y3 |
| 120 | A35-D10-Y4 |

In some embodiments, the compound of formula I is one of the following:

| Compound No. | Compound structure |
|---|---|
| 121 | [salicylamide-N-CH2-CH(OP(O)(OC2H5)2)-CH2-OP(O)(OC2H5)(OC2H5)] |
| 122 | [salicylate ester-O-(CH2)4-OP(O)(OC2H5)2] |
| 123 | [salicylate ester-O-CH2-CH(OP(O)(OC2H5)2)-CH2-OP(O)(OC2H5)2] |
| 124 | [salicylamide-NH-(CH2)4-OP(O)(OC2H5)2] |

| Compound No. | Compound structure |
|---|---|
| 125 | 2,5-dihydroxybenzoate ester of glycerol bis(diethyl phosphate) |
| 126 | 2,5-dihydroxybenzamide of 3-amino-1,2-propanediol bis(diethyl phosphate) |
| 127 | 2,4-dihydroxybenzoate ester of glycerol bis(diethyl phosphate) |
| 128 | 2,4-dihydroxybenzamide of 3-amino-1,2-propanediol bis(diethyl phosphate) |
| 129 | 2,3-dihydroxybenzoate ester of glycerol bis(diethyl phosphate) |
| 130 | 2,3-dihydroxybenzamide of 3-amino-1,2-propanediol bis(diethyl phosphate) |

| Compound No. | Compound structure |
|---|---|
| 131 | 2,5-dihydroxybenzoate ester of 4-hydroxybutyl diethyl phosphate |
| 132 | 2,5-dihydroxybenzamide of 4-aminobutyl diethyl phosphate |
| 133 | 2,4-dihydroxybenzoate ester of 4-hydroxybutyl diethyl phosphate |
| 134 | 2,4-dihydroxybenzamide of 4-aminobutyl diethyl phosphate |
| 135 | 2,3-dihydroxybenzoate ester of 4-hydroxybutyl diethyl phosphate |
| 136 | 2,3-dihydroxybenzamide of 4-aminobutyl diethyl phosphate |

Methods of Use

NSAIDs are not used in the treatment of DED for two reasons: first, there is no evidence that they would be efficacious; and second, they are associated with prohibitive ocular side effects, most notably corneal melt. Indeed, NSAIDs are contraindicated in patients with DED.

The most dangerous complication of topical ophthalmic NSAIDs is corneal melt. Corneal melt is a condition where the corneal epithelium is severely damaged or lost and is accompanied by thinning of the corneal stroma (it consists mainly of collagen). Progressive thinning of the stroma may result in perforation of the eye that can lead to loss of vision through major refractive errors or even to loss of the eye itself from subsequent complications such as infection. Corneal melts typically occur after ocular surgery and in the setting of inflammation or other insult to the corneal surface. However, corneal melts can occur in quiet eyes as well.

In general, all opinion leaders recommend extreme care in the use of NSAIDs in ophthalmology and do not recommend their use in DED because the risk of corneal melt is increased as the cornea is already compromised by DED.

The compounds described herein (e.g., compounds of Formula I, compounds of Formula II, and compounds 1-136) are, generally speaking, derivatives of NSAIDs and other compounds. For instance, PS is a derivative of the NSAID sulindac. Thus one would anticipate that it would also be contraindicated in the treatment of DED, especially since it can be readily hydrolyzed by corneal carboxylesterases to the NSAID sulindac, which is in turn converted to its active metabolites sulindac sulfide and sulindac sulfone.

However, PS is efficacious and also safe in the treatment of DED. In particular, PS, when administered at doses and over time periods effective to treat DED, does not cause corneal melt. PS is also efficacious and safe as an analgesic for eye pain.

In some embodiments, the present invention provides method of treating an ophthalmic condition in a patient, comprising administering to the patient a dose of one of the compounds described herein. In some embodiments, the compound is a compound of Formula I. In some embodiments, the compound is a compound of Formula II. In some embodiments, the compound is selected from compounds 1-120. In some embodiments, the compound is selected from compounds 121-136. According to certain embodiments, the ophthalmic condition is dry eye disease, pain or inflammation, pain and/or inflammation following ocular surgery, conjunctivitis, uveitis, cystoid macular edema, diabetic retinopathy, Sjogren's syndrome, pterygium, or mechanical trauma or chemical injury to the eye.

In certain embodiments, the dose is selected as described herein. In certain embodiments, the dose is at least 0.75 mg, at least 1.5 mg, at least 2 mg, at least 3 mg, or at least 4 mg. In some embodiments, the dose is no more than 0.75 mg, no more than 1.5 mg, no more than 2 mg, no more than 3 mg, or no more than 4 mg. In some embodiments, the dose is an analgesic dose. In some embodiments, the dose is an anti-inflammatory dose that is less than an analgesic dose, i.e., the dose is effective to treat dry-eye disease, but does not provide analgesia. In some embodiments, the dose is sufficient to treat the ophthalmic condition, but does not provide analgesia or anti-inflammatory activity. In preferred embodiments, the dose does not cause corneal melting.

The administering step may be performed by any appropriate delivery method known to those of skill in the art. In certain embodiments, the administering step comprises administering the compound locally to the surface of the eye, delivering the compound to the posterior part of the eye by direct injection, injecting the compound into the lacrimal gland, or depositing the compound within the eye.

The compound may be formulated for administration in any ocular formulation known to those of skill in the art. For example, the compound may be formulated in an eye drop, an injectable formulation, an ointment, a spray, a gel, or a slow release formulation. In some embodiments, the formulation comprises 0.3% by weight of the compound. In some embodiments, the formulation comprises 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5%, 3.0%, 3.5%, 4.0%, 4.5%, or 5.0% of the compound. In some preferred embodiments, the formulation comprises 0.5% of the compound. In some preferred embodiments, the formulation comprises 2.0% of the compound. In some embodiments, the administering step comprises administering two drops of the formulation. In some embodiments, the method comprises repeating the administering step twice, three times, or four times in a day. In some embodiments, the size of the drop is between 10-100 µL. The drop size may be about 10 µL, about 20 µL, about 30 µL, about 40 µL, about 50 µL, about 60 µL, about 70 µL, about 80 µL, about 90 µL, or about 100 µL.

In some embodiments, the method comprises repeating the administering step at least once daily for two days, 7 days, or 14 days.

In some embodiments, the present invention provides a method to treat DED, comprising administering a therapeutically effective dose of one of the compounds described herein. The DED may be associated, for example, with ocular inflammation and/or pain associated with ocular surgery; with uveitis or conjunctivitis; with cystoid macular edema or diabetic retinopathy; with pterygium; or with mechanical trauma or chemical injury to the eye. In preferred embodiments, the compound is administered topically, e.g., in eye drops. In some embodiments, the therapeutically effective dose for DED is at least 0.75 mg, at least 1.5 mg, or at least 2 mg. In some embodiments, the therapeutically effective dose for DED is no more than 0.75 mg, no more than 1.5 mg, or no more than 2 mg. In some embodiments, the dose is a dry eye disease dose that is less than an analgesic dose, i.e., the dose is effective to treat dry-eye disease, but does not provide analgesia. In preferred embodiments, the compound of Formula I is PS.

In some embodiments, the present invention provides a method to treat DED, comprising administering to an eye of a mammal a drop of a formulation of a compound of Formula I, wherein the formulation comprises less than 10% by weight of the compound of Formula I. In some embodiments, the formulation comprises 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 10% of the compound of Formula I. In some preferred embodiments, the formulation comprises 0.5% of the compound of Formula I. In some preferred embodiments, the formulation comprises 2.0% of the compound of Formula I. In some embodiments, the formulation comprises less than 10.0%, less than 9.5%, less than 9.0%, less than 8.5%, less than 8.0%, less than 7.5%, less than 7.0%, less than 6.5%, less than 6.0%, less than 5.5%, less than 5.0%, less than 4.5%, less than 4.0%, less than 3.5%, less than 3.0%, less than 2.5%, less than 2.0%, less than 1.9%, less than 1.8%, less than 1.7%, less than 1.6%, less than 1.5%, less than 1.4%, less than 1.3%, less than 1.2%, less than 1.1%, less than 1.0%, less than 0.9%, less than 0.8%, less than 0.7%, less than 0.6%, less than 0.5%, less than 0.4%, less than 0.3%, less than 0.2%, or less than 0.1% of the compound of Formula I. In some preferred embodiments, the formulation comprises less than 0.5% of the compound of Formula I. In some preferred embodiments, the formulation comprises less than 0.2% of the compound of Formula I. In some embodiments, the method comprises administering two drops of the formulation. In some embodiments, the method comprises repeating the administering step twice, three times, or four times in a day. In some embodiments, the size of the drop is between 10-100 µL. The drop size may be about 10 µL, about 20 µL, about 30 µL, about 40 µL, about 50 µL, about 60 µL, about 70 µL, about 80 µL, about 90 µL, or about 100 µL. In some embodiments, the method comprises repeating the administering step at least once daily for two days, 7 days, or 14 days.

In some embodiments, the present invention provides a method to treat ocular pain or inflammation. In some embodiments, the therapeutically effective dose for ocular pain or inflammation is at least 2.0 mg, at least 3.0 mg, or at least 4.0 mg. In some embodiments, the therapeutically effective dose for ocular pain or inflammation is no more than 2.0 mg, no more than 3.0 mg, or no more than 4.0 mg. The ocular pain or inflammation may be eye pain or acute inflammation, and may arise from eye surgery (e.g., cataract surgery). In preferred embodiments, the compound of Formula I is PS. In some embodiments, the present invention provides a method to treat ocular pain or inflammation, comprising administering to an eye of a mammal a drop of a formulation of a compound of Formula I, wherein the formulation comprises 0.3% by weight of the compound of Formula I. In some embodiments, the formulation comprises 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5%, 3.0%, 3.5%, 4.0%, 4.5%, or 5.0% of the compound of Formula I. In some preferred embodiments, the formulation comprises 0.5% of the compound of Formula I. In some preferred embodiments, the formulation comprises 2.0% of the compound of Formula I. In some embodiments, the method comprises administering two drops of the formulation. In some embodiments, the method comprises repeating the administering step twice, three times, or four times in a day. In some embodiments, the size of the drop is between 10-100 µL. The drop size may be about 10 µL, about 20 µL, about 30 µL, about 40 µL, about 50 µL, about 60 µL, about 70 µL, about 80 µL, about 90 µL, or about 100 µL. In some embodiments, the method comprises repeating the administering step at least once daily for two days, 7 days, or 14 days.

In some embodiments, the present invention provides a method to treat conjunctivitis, such as allergic conjunctivitis. In some embodiments, the therapeutically effective dose for conjunctivitis is at least 2.0 mg, at least 3.0 mg, or at least 4.0 mg. In some embodiments, the therapeutically effective dose for conjunctivitis is no more than 2.0 mg, no more than 3.0 mg, or no more than 4.0 mg. The conjunctivitis may be allergic conjunctivitis, viral conjunctivitis, or bacterial conjunctivitis. In preferred embodiments, the compound of Formula I is PS. In some embodiments, the present invention provides a method to treat conjunctivitis, comprising administering to an eye of a mammal a drop of a formulation of a compound of Formula I, wherein the formulation comprises 0.3% by weight of the compound of Formula I. In some embodiments, the formulation comprises 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5%, 3.0%, 3.5%, 4.0%, 4.5%, or 5.0% of the compound of Formula I. In some preferred embodiments, the formulation comprises 0.5% of the compound of Formula I. In some preferred embodiments, the formulation comprises 2.0% of the compound of Formula I. In some embodiments, the method comprises administering two drops of the formulation. In some embodiments, the method comprises repeating the administering step twice, three times, or four times in a day. In some embodiments, the size of the drop is between 10-100 µL. The drop size may be about 10 µL, about 20 µL, about 30 µL, about 40 µL, about 50 µL, about 60 µL, about 70 µL, about 80 µL, about 90 µL, or about 100 µL. In some embodiments, the method comprises repeating the administering step at least once daily for two days, 7 days, or 14 days.

In some embodiments, the present invention provides a method to treat cystoid macular edema or diabetic retinopathy, comprising administering a therapeutically effective dose of one of the compounds described herein. The dose may be selected as described herein. In these embodiments, the compound may be administered locally to the surface of the eye, delivered to the posterior part of the eye by direct injection, or deposited within the eye in a slow-release formulation.

In some embodiments, the present invention provides a method to treat Sjogren's syndrome, comprising administering a therapeutically effective dose of one of the compounds described herein. The dose may be selected as described herein. In these embodiments, the compound may be administered locally to the surface of the eye, to the lacrimal gland by application to the skin in proximity to the lacrimal gland, by direct injection to the lacrimal gland, deposited into or near the lacrimal gland preferably formulated in a slow release formulation.

In some embodiments, the present invention provides a method to treat pterygium, comprising administering a therapeutically effective dose of one of the compounds described herein. The dose may be selected as described herein. In these embodiments, the compound may be administered to the surface of the eye, e.g. in an eye drop formulation, an ointment, or a spray; or by microinjection into the pterygium.

In some embodiments, the present invention provides a method to treat mechanical trauma or chemical injury to the eye, comprising administering a therapeutically effective dose of one of the compounds described herein. The dose may be selected as described herein. In these embodiments, the compound may be administered locally to the affected area, e.g., in an eye drop formulation, an ointment, a spray, or a suitable slow-release formulation.

The compounds and compositions described herein can be used in methods for treating diseases of the eye. In some embodiments, the diseases of the eye that are treated by the compounds, compositions, methods, and kits described herein include dry eye disease and retinopathy. In some embodiments, retinopathy may include the diseases of diabetic retinopathy, retinopathy of prematurity, VEGF retinopathy, age related macular degeneration, retinal vein occlusion, and/or hypertensive retinopathy. In certain embodiments, retinopathy may be diabetic retinopathy.

Dry eye disease (DED) is a multi-factorial disease of the ocular surface characterized by loss of homeostasis of the tear film and accompanied by ocular symptoms. The tear film in DED is abnormal because of one or more of three reasons: tear production is decreased; tear evaporation is increased; or the mucus or lipids of the tear are abnormal. The clinical manifestations of DED can vary in severity from very mild to the point that they decrease the ability to perform activities requiring visual attention such as reading and driving, seriously affecting the patient's quality of life. Given its worldwide distribution and the lack of a single definitive test or consensus of criteria for its diagnosis, prevalence figures for DED vary. The best estimate of its prevalence is 15% (17.9% for women and 10.5% for men); some authors consider even 15% an underestimate.

DED is an inflammatory disease whose pathogenesis is under extensive study. For example, dysfunction of the tear glands, chronic irritative stress or systemic autoimmune diseases can lead to ocular inflammation. In turn, inflammation causes dysfunction or death of cells responsible for tear secretion establishing a vicious cycle, which, regardless of the initiating insult, leads to ocular surface disease. The important contributors to the inflammatory process in DED are: (1) activation of pro-inflammatory cytokines; tear hyperosmolarity, which stimulates inflammatory mediators through MAPKs; (2) matrix metalloproteinases (MMPs), which lyse components of the corneal epithelial basement membrane and tight junction proteins; (3) chemokines, which recruit nearby responsive cells; and (4) T cells, which can amplify the cascade by attracting inflammatory cells, e.g., in Sjogren's syndrome.

The treatment of DED depends on its clinical severity. The symptoms of very mild disease are often treated with artificial tears, which provide partial relief but do not suppress inflammation. Advanced disease is managed with the immunosuppressant cyclosporine, the recently approved integrin antagonist lifitegrast, punctal plugs, or rarely corticosteroids. Non-steroidal anti-inflammatory drugs (NSAIDs) have no role in DES.

In an embodiment, the invention includes a method for treating dry eye disease in a patient in need thereof, the method comprising administering to the patient a therapeutically effective amount of a compound of the invention, such as a compound of formula III or formula IV, or a pharmaceutically acceptable salt thereof.

In some embodiments, the compound may be a compound of formula III or a pharmaceutically acceptable salt thereof.

In some embodiments, the methods for the treatment of dry eye disease may include the administration of a therapeutically effective amount of an additional active agent. In some embodiments, the additional active agent may include one or more of an antibiotic, cyclosporine, and lifitegrast.

Diabetic retinopathy refers to retinal changes that occur in patients with diabetes mellitus. These changes affect the small blood vessels of the retina and can lead to vision loss through several different pathways. Macular edema, defined as retinal thickening and edema involving the macula can occur at any stage of diabetic retinopathy. Diabetic retinopathy is one of the commonest causes of vision loss. Vascular endothelial growth factor (VEGF) is secreted by ischemic retina. VEGF leads to (a) increased vascular permeability resulting in retinal swelling/edema and (b) angiogenesis—new blood vessel formation. Agents that suppress VEGF can control diabetic retinopathy.

In addition to diabetic retinopathy, several other ocular diseases are characterized by abnormal vascular phenomena that are predominantly dependent on VEGF. Given the role of VEGF in these disorders, controlling VEGF is an approach to their prevention and treatment. Prominent among them is age-related macular degeneration (AMD), a degenerative disease of the central portion of the retina (the macula) that results primarily in loss of central vision. Central vision is required for activities such as driving, reading, watching television, and performing activities of daily living. AMD is classified as dry (atrophic) or wet (neovascular or exudative) for clinical purposes. Wet AMD, also referred to as choroidal neovascularization is characterized by growth of abnormal vessels into the subretinal space, usually from the choroidal circulation and less frequently from the retinal circulation. These abnormal blood vessels leak, leading to collections of subretinal fluid and/or blood beneath the retina.

Retinal vein occlusion (RVO) is an important cause of visual loss among older adults throughout the world. An important component of RVO which is also a therapeutic target for this entity are its secondary complications that affect vision, including macular edema, retinal neovascularization, and anterior segment neovascularization. VEGF pays a crucial role in these vision-determining complications. Patients with severe (ischemic) central retinal vein occlusion are at particularly high risk for neovascular glaucoma, often within the first few months of diagnosis, and should be observed at least monthly for development of anterior segment neovascularization during this period. Indeed, patients with severe (ischemic) central retinal vein occlusion are at particularly high risk for neovascular glaucoma, and are observed closely for development of anterior segment neovascularization. VEGF inhibitors in patients with RVO are hypothesized to limit macular edema and improve vision by decreasing vascular permeability.

In an embodiment, the invention includes a method for treating diabetic retinopathy in a patient in need thereof, the method comprising administering to the patient a therapeutically effective amount of a compound of the invention, such as a compound of formula III or formula IV, or a pharmaceutically acceptable salt thereof.

In an embodiment, the invention includes a method of treating an ophthalmic condition in a patient in need thereof, wherein the ophthalmic condition is selected from the group consisting of dry eye disease and retinopathy, the method comprising administering to the patient a therapeutically effective amount of a compound with reduced risk of corneal melt of, such as a compound of formula III or formula IV, or a pharmaceutically acceptable salt thereof.

In an embodiment, the invention includes a composition for treating an ophthalmic condition in a patient in need thereof, wherein the ophthalmic condition is selected from the group consisting of dry eye disease and retinopathy, the composition comprising a therapeutically effective amount of a compound with reduced risk of corneal melt, such as a compound formula III or formula IV, or a pharmaceutically acceptable salt thereof, and a pharmaceutically acceptable carrier.

In some embodiments, the compound may be a compound of formula III or a pharmaceutically acceptable salt thereof.

In some embodiments, the methods for the treatment of diabetic retinopathy may include the administration of a therapeutically effective amount of an additional active agent. In some embodiments, the additional active agent may include one or more of an antibiotic, cyclosporine, and lifitegrast.

In some embodiments, the antibiotic the antibiotic may include one or more of tetracycline, tobramycin, chlortetracycline, bacitracin, neomycin, polymyxin, gramicidin, oxytetracycline, chloramphenicol, gentamycin, and erythromycin. Other antibiotics include aminoglycoside, ampicillin, carbenicillin, cefazolin, cephalosporin, chloramphenicol, clindamycin, everninomycin, gentamycin, kanamycin, lipopeptides, methicillin, nafcillin, novobiocia, oxazolidinones, penicillin, quinolones, rifampin, streptogramins, streptomycin, sulfamethoxazole, sulfonamide, trimethoprim, and vancomycin.

In some embodiments, the antibiotic may include neomycin sulfate or polymyxin B sulfate.

In some embodiments, the methods described herein may include the administration of an additional compound for treating an ophthalmic condition, the additional compound may comprise one or more of the compounds disclosed in U.S. Pat. No. 8,236,820 and/or U.S. Patent Application Nos. 2009/0099137, 2013/0225529, and 2014/0315834, the entireties of which are incorporated herein by reference.

Efficacy of the methods, compounds, and combinations of compounds described herein in treating, preventing and/or managing the indicated diseases or disorders can be tested using various animal models known in the art.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

As used herein, the terms "administer," "administration" or "administering" refer to (1) providing, giving, dosing, and/or prescribing by either a health practitioner or his authorized agent or under his or her direction according to the disclosure; and/or (2) putting into, taking or consuming by the mammal, according to the disclosure.

The terms "co-administration," "co-administering," "administered in combination with," "administering in combination with," "simultaneous," and "concurrent," as used herein, encompass administration of two or more active pharmaceutical ingredients to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term "compound with reduced risk of corneal melt" refers to compounds that are less likely to cause corneal melt in a patient being treated when compared to an NSAID known to cause corneal melt (e.g., diclofenac (see, e.g., Julianne, C. et al. "Corneal Melting Associated with Use of Topical Nonsteroidal Anti-Inflammatory Drugs after Ocular Surger," (2000) 118:1129-1132)) at about the same dosage. The compounds of the invention, such as compounds of formula (III) and formula (IV) are compounds with reduced risk of corneal melt.

The terms "active pharmaceutical ingredient" and "drug" include the compounds described herein and, more specifically, the compounds described by formula (III) or formula (IV).

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "QD," "qd," or "q.d." mean quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

The term "pharmaceutically acceptable salt" refers to salts derived from a variety of organic and inorganic counter ions known in the art. Pharmaceutically acceptable acid addition salts can be formed with inorganic acids and organic acids. Preferred inorganic acids from which salts can be derived include, for example, hydrochloric acid, hydrobromic acid, sulfuric acid, nitric acid and phosphoric acid. Preferred organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs disclosed herein, can also be incorporated into the described compositions and methods.

As used herein, the terms "treat," "treatment," and/or "treating" may refer to the management of a disease, disorder, or pathological condition, or symptom thereof with the intent to cure, ameliorate, stabilize, and/or control the disease, disorder, pathological condition or symptom thereof. Regarding control of the disease, disorder, or pathological condition more specifically, "control" may include the absence of condition progression, as assessed by the response to the methods recited herein, where such response may be complete (e.g., placing the disease in remission) or partial (e.g., lessening or ameliorating any symptoms associated with the condition).

As used herein, the terms "modulate" and "modulation" refer to a change in biological activity for a biological molecule (e.g., a protein, gene, peptide, antibody, and the like), where such change may relate to an increase in biological activity (e.g., increased activity, agonism, activation, expression, upregulation, and/or increased expression) or decrease in biological activity (e.g., decreased activity, antagonism, suppression, deactivation, downregulation, and/or decreased expression) for the biological molecule.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C- or $^{14}$C-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)-isomer and 20% (R)-isomer, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., Enantiomers, Racemates and Resolutions, Wiley Interscience, New York (1981); E. L. Eliel, Stereochemistry of Carbon Compounds, McGraw-Hill, New York (1962); and E. L. Eliel and S. H. Wilen, Stereochemistry of Organic Compounds, Wiley-Interscience, New York (1994).

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

"Solvate" refers to a compound in physical association with one or more molecules of a pharmaceutically acceptable solvent.

Compounds of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

For the avoidance of doubt, it is intended herein that particular features (for example integers, characteristics, values, uses, diseases, formulae, compounds or groups) described in conjunction with a particular aspect, embodiment or example of the invention are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any disclosed embodiments. The invention extends to any novel one, or novel combination, of the features disclosed in this specification (including any accompanying claims, abstract and drawings), or to any novel one, or any novel combination, of the steps of any method or process so disclosed.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All embodiments of the invention can, in the alternative, be more specifically defined by any of the transitional terms "comprising," "consisting essentially of," and "consisting of."

The term "LASIK", as used herein, is an acronym for LAser in SItu Keratomileusis. This is a type of refractive surgery in which the cornea is reshaped to change its optical power. Specifically, a disc of cornea is raised as a flap, then an excimer laser is used to reshape the middle layer of corneal tissue, producing surgical flattening. LASIK surgery may be used for correcting myopia, hyperopia, and astigmatism.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

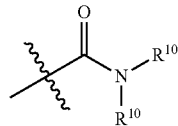

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

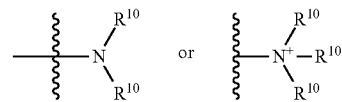

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

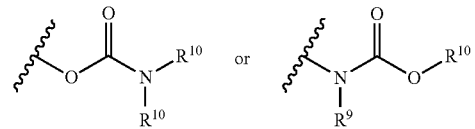

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In exemplary embodiments, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]

hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent. Examples of heteroalkyls include alkoxy, alkylamino, alkoxyalkyl, and alkylaminoalkyl.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "silyloxy" refers to an oxygen moiety with a silyl attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

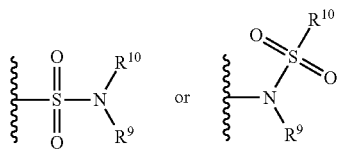

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—$R^{10}$, wherein $R^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—$R^{10}$, wherein $R^{10}$ represents a hydrocarbyl.

The term "thioalkyl", as used herein, refers to an alkyl group substituted with a thiol group.

The term "thioester", as used herein, refers to a group —C(O)S$R^{10}$ or —SC(O)$R^{10}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

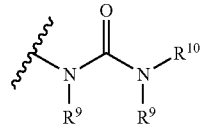

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. For example, a compound that prevents infection may reduce the frequency of infection and/or reduce the severity of infection.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The phrases "conjoint administration" and "administered conjointly" refer to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

The term "prodrug" is intended to encompass compounds which, under physiologic conditions, are converted into the therapeutically active agents of the present invention (e.g., a compound selected from Table 1). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds selected from Table 1 in a formulation represented above can be replaced with the corresponding suitable prodrug, e.g., wherein a hydroxyl in the parent compound is presented as an ester or a carbonate or carboxylic acid present in the parent compound is presented as an ester.

The terms "agonist", "antagonist", and "inhibitor" are used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal cells or tissues. They include, for example, agents whose structure is known, and those whose structure is not known. An agonist refers to an agent that increases the activity of a protein.

Pharmaceutical Compositions

The compositions and methods of the present invention may be utilized to treat an individual in need thereof, such as a patient with an ophthalmic condition such as dry eye disease, inflammation, pain, or conjunctivitis. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection, that circumvent transport or diffusion through an epithelial barrier), the aqueous solution is pyrogen-free, or substantially pyrogen-free. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

Further examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein may encompass a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) glycols, such as propylene glycol; (2) polyols, such as glycerin, sorbitol, mannitol and polyethylene glycol; (3) esters, such as ethyl oleate and ethyl laurate; (4) buffering agents, such as magnesium hydroxide and aluminum hydroxide; (5) pyrogen-free water; (6) isotonic saline; (7) Ringer's solution; (8) ethyl alcohol; (9) phosphate buffer solutions; and (10) other non-toxic compatible substances employed in pharmaceutical formulations.

A pharmaceutical composition (preparation) can be administered to a subject by any of a number of routes of administration including, for example, intraocularly (for example, by intraocular injection); and topically (for example, as a cream, ointment or spray applied to the skin, or as an eye drop). In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both.

Dosage forms for topical administration include ophthalmic formulations, such as eye drops. The active compound may be mixed under sterile conditions with a pharmaceutically acceptable carrier, and with any preservatives or buffers that may be required, as for example, benzalkonium chloride.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. In certain embodiments, different compounds of Formula I, may be conjointly administered with each other, or with other agents suitable for the treatment of an ophthalmic condition. For example, the following agents or classes of agents may be conjointly administered with a compound of Formula I: doxocycline; decosahexanoic acid; angiogenesis inhibitors, e.g., VEGF inhibitors, such as pegaptanib sodium, bevacizumab, ranibizumab, AV-951, vandetanib, semaxanib, CBO-P11, axitinib, sorafenib, sunitinib, pazopanib, and TIMP3; anesthetics and pain killing agents such as lidocaine and related compounds and benzodiazepam and related compounds; anti-cancer agents such as 5-fluorouracil, adriamycin, mitomycin and related compounds; anti-inflammatory agents such as 6-mannose phosphate; anti-fungal agents such as fluconazole and related compounds; anti-viral agents such as trisodium phosphomonoformate, trifluorothymidine, acyclovir, ganciclovir, DDI, DDC, and AZT; cell transport/mobility impending agents such as colchicine, vincristine, cytochalasin B, and related compounds; antiglaucoma drugs such as beta-blockers: timolol, betaxol, atenalol, etc; prostaglandins such as latanoprost and travoprost, etc.; immunological response modifiers such as muramyl dipeptide and related compounds; peptides and proteins such as cyclosporin, insulin, growth hormones, insulin related growth factor, nerve growth factor (optionally in further combination with decosahexanoic acid), heat shock proteins and related compounds; estrogen treatments; anti-histamines such as brompheniramine, chlorpheniramine debrompheniramine, dexchlorpheniramine, carbinoxamine, clemastine, diphenhydramine, pyrilamine, tripelennamine, tripolidine, methdilazine, bromodiphenhydramine, promethazine, azatadine, cyproheptadine, diphenylpyraline, doxylamine, trimeprazine, phenindamine, ketotifen, hydroxyzine, tazifylline, temelastine, meclizine, acrivastine, setastine, oxatomide, mequitazine, levocabastine, lodoxamide, rocastine, phenindamine, azelastine, and ebastine, fexofenadine, loratadine, descarboethoxy loratadine, astemizole, norastemizole, desmethylastemizole, cetirizine, acrivastine, and temelastine; corticosteroids such as dexamethasone, dexamethasone 21-phosphate, fluorometholone, medrysone, betamethasone, triamcinolone, triamcinolone acetonide, triminolone, prednisone, prednisolone, prednisolone 21-phosphate, prednisolone acetate, hydrocortisone, hydrocortisone acetate, prednicarbate, deflazacort, halomethasone, tixocortol, prednylidene (21-diethylaminoacetate), prednival, paramethasone, prednisolone, methylprednisolone, meprednisone, mazipredone, isoflupredone, halopredone acetate, halcinonide, formocortal, flurandrenolide, fluprednisolone, flurpredinidine acetate, fluperolone acetate, fluocortolone, fluocortin butyl, fluocinonide, fluocinolone, fluocinolone acetonide, flunisolide, flumethasone, fludrocortisone, fluclorinide, fluorometholone, enoxolone, difluprednate, diflucortolone, diflorasone diacetate, desoximetasone (desoxymethasone), desonide, descinolone, cortivazol, corticosterone, cortisone, cloprednol, clocortolone, clobetasone, clobetasol, chloroprednisone, cafestol, budesonide, beclomethasone, amcinonide, allopregnane acetonide, alclometasone, 21-acetoxypregnenolone, tralonide, diflorasone acetate, deacylcortivazol, RU-26988, budesonide, and deacylcortivazol oxetanone. All of the above-cited corticosteroids are known compounds. Further information about the compounds may be found, for example, in The Merck Index, Thirteenth Edition (2001), and the publications cited therein, the entire contents of which are hereby incorporated herein by reference. In certain embodiments, the corticosteroid is selected from fluocinolone acetonide, triamcinolone acetonide, dexamethasone, and related compounds, or any combination thereof; and carbonic anhydaze inhibitors.

Further examples of agents or classes of agents may be conjointly administered with a compound of Formula I include: antioxidants such as OT-551; agents targeting the IL-2Rα receptor such as daclizumab; TNFα antagonists such as infliximab; antibiotics such as sirolimus; nicotonic antagonists such as mecamylamine; steroids such as anecortave acetate; photosensitizers with photodynamic therapy such as verteporfin; PGE1 (e.g., alprostadil); synthetic retinoids such as fenretinide; carbonic anhydrase inhibitors such as acetazolamide; P2Y2 receptor agonists such as denufosol tetrasodium and diquafosol; interferons such as interferon beta; NSAIDs such as bromfenac and nepafenac; anti-VEGF agents such as EYE001, VEGF-Trap, bevasiranib, and vatalanib; anti-VEGF agents/kinase mediators such as TG100801; antiangiogenic agents such as AG-013, 958 and squalamine lactate; and siRNA's such as CAND5 and AGN211745.

Further examples of agents or classes of agents may be conjointly administered with a compound of Formula I include: DE-104; PF-04217329; PF-03187207; AL 37807; OPC-12759; chemotherapeutic agents such as mitomycin C; synthetic structural analogs of prostaglandin such as bimatoprost; alpha 2 agonists such as brimonidine; carbonic anhydrase inhibitors such as dorzolamide HCl; prostaglandin derivatives and analogs such as tafluprost and travoprost; NMDA antagonists such as memantine; hyaluronic acid (e.g., sodium hyaluronate); corticosteroids such as loteprednol etabonate, difluprednate and rimexolone; antibiotics such as doxycycline; agents that increase mucin such as ecabet and rebamipide; lubricants such as the combination of carboxymethylcellulose sodium and glycerin; A3 adenosine receptor agonists such as CF-101; immunomodulators such as thalidomide; TNFα antagonists such as etanercept; protein kinase C-b inhibitors such as ruboxistaurin; immunosuppressants such as sirolimus; PARP inhibitors such as AG-014699; neuroprotective thrombolytic agents such as microplasmin; hyaluronidase; oxidizing agents such as carbamide; somatostatin analogs such as octreotide acetate; angiotensin II receptor antagonists such as candesartan cilexetil; disease-modifying antirheumatic drugs such as leflunomide; AEB071; TNF antagonists such as adalimumab; CD11 antagonists such as efalizumab; calcineurin inhibitors such as LX211; interferons such as interferon α-2a; and human alpha fetoproteins such as MM-093.

In addition to the above agents, other agents are suitable for administration to the eye and its surrounding tissues to produce a local or a systemic physiologic or pharmacologic beneficial effect. Such agents may be conjointly administered with a compound of Formula I. Examples of such agents include neuroprotectants such as nimodipine and related compounds; antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole, and sulfisoxazole; antivirals, including idoxuridine; other antibacterial agents such as nitrofurazone and sodium propionate; antiallergenics such as antazoline, methapyriline, chlorpheniramine, pyrilamine, and prophenpyridamine; decongestants such as phenylephrine, naphazoline, and tetrahydrazoline; miotics and anti-cholinesterase agents such as pilocarpine, eserine salicylate, carbachol, di-isopropyl fluorophosphate, phospholine iodine, and demecarium bromide; mydriatics such as atropine sulfate, cyclopentolate, homatropine, scopolamine, tropicamide, eucatropine, and hydroxyamphetamine; sympathomimetics such as epinephrine; and prodrugs such as those described in Design of Prodrugs, edited by Hans Bundgaard, Elsevier Scientific Publishing Co., Amsterdam, 1985. Reference may be made to any standard pharmaceutical textbook such as Remington's Pharmaceutical Sciences (Remington's Pharmaceutical Sciences. Mack Publishing Company, Easton, Pa., USA 1985) for the identity of other agents.

In some preferred embodiments, a compound of Formula I may be conjointly administered with a corticosteroid.

In some preferred embodiments, a compound of Formula I may be conjointly administered with an antibiotic.

In some preferred embodiments, a compound of Formula I may be conjointly administered with an anti-histamine.

In certain embodiments, compounds of Formula I may be conjointly administered with non-chemical methods suitable for the treatment of an ophthalmic condition. In certain embodiments, compounds of Formula I may be conjointly administered with laser treatment (e.g., photocoagulation or photodynamic therapy), macular translocation surgery or with devices (e.g., brimonidine tartrate implant).

In certain embodiments, compounds of Formula I may be conjointly administered with an anti-VGEF agent.

In certain embodiments, compounds of Formula I may be conjointly administered with an anti-proliferative agent such as mitomycin C, This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

The term "pharmaceutically acceptable basic addition salt" as used herein means any non-toxic organic or inorganic base addition salt of any acid compounds. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

In an embodiment, the compounds described herein may be NSAID derivative compounds.

NSAIDs are not used in the treatment of DED for two reasons. First, there is no evidence that they would be efficacious. Second, they are associated with prohibitive ocular side effects, most notably corneal melt. Indeed, NSAIDs are contraindicated in patients with DED.

The most dangerous complication of topical ophthalmic NSAIDs is corneal melt. Corneal melt is a condition where the corneal epithelium is severely damaged or lost and is accompanied by thinning of the corneal stroma, which consists mainly of collagen. Progressive thinning of the stroma may result in perforation of the eye that can lead to loss of vision through major refractive errors or even to loss of the eye itself from subsequent complications such as infection. Corneal melts typically occur after ocular surgery and in the setting of inflammation or other insult to the corneal surface. However, corneal melt may occur in the absence of inflammation or other insult.

In general, opinion leaders recommend extreme care in the use of NSAIDs in ophthalmology and do not recommend their use in DED because the risk of corneal melt is increased as the cornea is already compromised by DED.

In an embodiment, the compounds described herein include the NSAID derivative compounds of Formula III and Formula IV, or the pharmaceutically acceptable salts thereof.

In an embodiment, the compound of the invention may include the compound of Formula II:

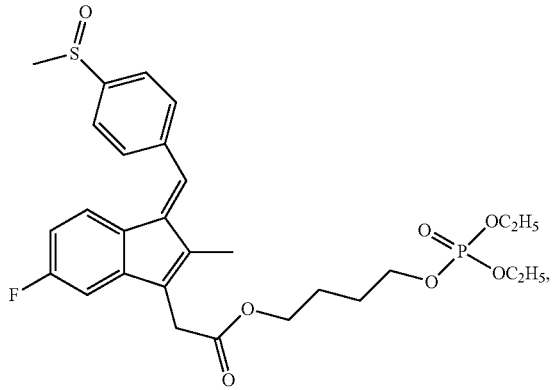

(III)

or a pharmaceutically acceptable salt thereof.

In an embodiment, the compound of the invention may include the compound of Formula IV:

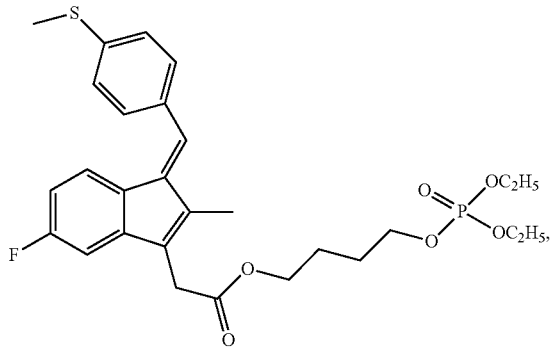

(IV)

or a pharmaceutically acceptable salt thereof.

The compounds of formulas III and IV are described in U.S. Pat. No. 8,236,820, the entirety of which is incorporated herein by reference.

For example, the Formula III compound (PS) is a derivative of the NSAID sulindac. Thus, one may anticipate that it would also be either ineffective or contraindicated in the treatment of DED.

In some embodiments, the compounds of Formula III and Formula IV may penetrate one or more of the cornea, sclera, and conjunctiva to contact the retina.

However, PS is efficacious and safe in the treatment of DED. In particular, PS, when administered at doses and over time periods effective to treat DED, does not cause corneal melt.

PS is also efficacious and safe as an analgesic for eye pain. Since PS is not behaving as a conventional NSAID, one would expect that PS would lose the beneficial analgesic properties displayed by ophthalmic NSAIDs such as ketorolac and others. However, PS displays a strong analgesic effect in ocular tissues.

In an embodiment, the invention provides a pharmaceutical composition for use in the treatment of the diseases and conditions described herein.

The pharmaceutical compositions are typically formulated to provide a therapeutically effective amount of a compound of formula (III) or formula (IV), as described herein, or a pharmaceutically acceptable salt, solvate, or hydrate thereof, as the active ingredient.

In some embodiments, the pharmaceutical compositions described herein may include an additional active agent. In some embodiments, the additional active agent may include one or more of an antibiotic, cyclosporine, and lifitegrast.

Typically, the pharmaceutical compositions also comprise one or more pharmaceutically acceptable excipients, carriers, including inert solid diluents and fillers, diluents, including sterile aqueous solution and various organic solvents, permeation enhancers, solubilizers and adjuvants.

The pharmaceutical compositions described above are preferably for use in the treatment of an ophthalmic condition or disease, such as dry eye disease or diabetic retinopathy.

In some embodiments, the concentration of a compound of formula (III) or formula (IV) provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of a compound of formula (III) or formula (IV) provided in the pharmaceutical compositions of the invention is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25%, 12%, 11.75%, 11.50%, 11.25%, 11%, 10.75%, 10.50%, 10.25%, 10%, 9.75%, 9.50%, 9.25%, 9%, 8.75%, 8.50%, 8.25%, 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of a compound of formula (III) or formula (IV) provided in the pharmaceutical compositions of the invention is in the range from about 0.0001% to about 50%, about 0.001% to about 40%, about 0.01% to about 30%, about 0.02% to about 29%, about 0.03%, to about 28%, about 0.04%, to about 27%, about 0.05% to about 26%, about 0.06%, to about 25%, about 0.07%, to about 24%, about 0.08%, to about 23%, about 0.09%, to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8%, to about 14%, about 0.9%, to about 12% or about 1% to about 10% w/w, w/v or v/v of the pharmaceutical composition.

In some embodiments, the concentration of a compound of formula (III) or formula (IV) provided in the pharmaceutical compositions of the invention is in the range from about 0.001% to about 10%, about 0.01%, to about 5%, about 0.02% to about 4.5%, about 0.03%, to about 4%, about 0.04% to about 3.5%, about 0.05% to about 3%, about 0.06% to about 2.5%, about 0.07% to about 2%, about 0.08%, to about 1.5%, about 0.09%, to about 1%, about 0.1% to about 0.9% w/w, w/v or v/v of the pharmaceutical composition.

In some embodiments, the amount of a compound of formula (III) or formula (IV) provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of a compound of formula (III) or formula (IV) provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5 g, 3 g, 3.5 g, 4 g, 4.5 g, 5 g, 5.5 g, 6 g, 6.5 g, 7 g, 7.5 g, 8 g, 8.5 g, 9 g, 9.5 g, or 10 g.

Each of the compounds provided according to the invention is effective over a wide dosage range. For example, in the treatment of adult humans, dosages independently ranging from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician.

Described below are non-limiting pharmaceutical compositions and methods for preparing the same.

In preferred embodiments, the invention provides a pharmaceutical composition for topical delivery containing a compound of formula (III) or formula (IV) described herein, and a pharmaceutical excipient suitable for topical delivery.

Compositions of the invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The compositions described herein may be formulated for administration topically to the eye and surrounding tissues, particularly to the inner surface of the eye and the inner surface of the eyelids (including e.g. cornea, conjunctiva and sclera). Such compositions, for example, may be formulated for instillation administration, administration into conjunctival sac and conjunctival administration. In particular, the compositions described herein may be formulated as eye drops. Such eye drop formulations may include a liquid or semisolid pharmaceutical composition adapted to administration to the eye. A typical example of an eye drop composition is an ophthalmic solution to be administered dropwise to the eye.

In certain embodiments, the compositions of the invention are in the form of eye drops. In some embodiments, the size of the drop is between about 10 and about 100 μL. The drop size may be greater than about 10 μL, greater than about 20 μL, greater than about 30 μL, greater than about 40 μL, greater than about 50 μL, greater than about 60 μL, greater than about 70 μL, greater than about 80 μL, greater than about 90 μL, or greater than about 100 μL. The drop size may be less than about 10 μL, less than about 20 μL, less than about 30 μL, less than about 40 μL, less than about 50 μL, less than about 60 μL, less than about 70 μL, less than about 80 μL, less than about 90 μL, or less than about 100 μL.

The pharmaceutical compositions also may comprise suitable solid or gel phase carriers or excipients, which are compounds that allow increased penetration of, or assist in the delivery of, therapeutic molecules across the membranes of the eye, including, but not limited to, the cornea, conjunctiva, and sclera. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

In some embodiments, the compositions described herein may include liquid formulations, semi-solid formulations, and multicompartment formulations.

In an embodiment, the compositions described herein may be liquid formulations that may include an ophthalmic solution of PS and/or a microemulsion of PS. Active pharmaceutical ingredients (APIs) for which microemulsions have been developed include cyclosporine A and flurbiprofen axetil. Successful approaches to extend the contact time of liquid dosage forms with ocular tissues and to increase the tissue uptake of the API include the use of excipients that increase viscosity, enhance penetration, or cyclodextrins. Cyclodextrins are cyclic oligosaccharides that form inclusion complexes with APIs that increase the aqueous solubility and bioavailability of hydrophobic APIs. In an embodiment, the compositions described herein may include β-cyclodextrin and a therapeutically effective amount of PS.

In an embodiment, the invention includes a composition for treating an ophthalmic condition in a patient in need thereof, wherein the ophthalmic condition is selected from the group consisting of dry eye disease and retinopathy, the composition comprising a therapeutically effective amount of a compound of formula I or formula II, or a pharmaceutically acceptable salt thereof. In some embodiments, the compositions described herein include a pharmaceutically acceptable carrier. In some embodiments, the compositions described herein include one or more of a solubilizing agent, an alcohol, an acid, and a preservative.

In some embodiments, the compositions described herein include a solubilizing agent and an alcohol. In some embodiments, the compositions described herein include a solubilizing agents and an acid. In some embodiments, the compositions described herein include a solubilizing agents and a preservative. In some embodiments, the compositions described herein include a solubilizing agent, an alcohol, and an acid. In some embodiments, the compositions described herein include a solubilizing agent, an alcohol, an acid, and a preservative.

In some embodiments, the compositions of the invention may include a compound of formula I or formula II, or a pharmaceutically acceptable salt thereof, in an amount, by weight, of about 0.5% to about 75%, or about 0.5% to about 70%, or about 0.5% to about 65%, or about 0.5% to about 60%, or about 0.5% to about 55%, or about 0.5% to about 50%, or about 0.5% to about 45%, or about 0.5% to about 40%, or about 0.5% to about 35%, or about 0.5% to about 30%, or about 0.5% to about 25%, or about 0.5% to about 20%, or about 0.5% to about 15%, or about 0.5% to about 10%, or about 0.5% to about 9%, or about 0.5% to about 8%, or about 0.5% to about 7%, or about 0.5% to about 6%, or about 0.5% to about 5%, or about 0.5% to about 4%, or about 0.5% to about 3%, or about 0.5% to about 2%, or about 0.5% to about 1%.

In some embodiments, the solubilizing agent is vitamin E TPGS (d-α-tocopheryl polyethylene glycol 1000 succinate). In some embodiments, the compositions described herein include a solubilizing agent in an amount, by weight, of about 0.5% to about 75%, or about 1% to about 70%, or about 1% to about 65%, or about 1% to about 60%, or about 1% to about 55%, or about 1% to about 50%, or about 1% to about 45%, or about 1% to about 40%, or about 1% to about 35%, or about 1% to about 30%, or about 1% to about 25%, or about 1% to about 20%, or about 1% to about 15%, or about 1% to about 10%, or about 1% to about 5%.

In some embodiments, the alcohol is a sugar alcohol, such as mannitol. In some embodiments, the compositions described herein include an alcohol in an amount by weight, of about 0.5% to about 75%, or about 0.5% to about 70%, or about 0.5% to about 65%, or about 0.5% to about 60%, or about 0.5% to about 55%, or about 0.5% to about 50%, or about 0.5% to about 45%, or about 0.5% to about 40%, or about 0.5% to about 35%, or about 0.5% to about 30%, or about 0.5% to about 25%, or about 0.5% to about 20%, or about 0.5% to about 15%, or about 0.5% to about 10%, or about 0.5% to about 9%, or about 0.5% to about 8%, or about 0.5% to about 7%, or about 0.5% to about 6%, or about 0.5% to about 5%, or about 0.5% to about 4%, or about 0.5% to about 3%, or about 0.5% to about 2%, or about 0.5% to about 1%.

In some embodiments, the acid is boric acid. In some embodiments, the compositions described herein include an acid in an amount, by weight, of about 0.5% to about 75%, or about 0.5% to about 70%, or about 0.5% to about 65%, or about 0.5% to about 60%, or about 0.5% to about 55%, or about 0.5% to about 50%, or about 0.5% to about 45%, or about 0.5% to about 40%, or about 0.5% to about 35%, or about 0.5% to about 30%, or about 0.5% to about 25%, or about 0.5% to about 20%, or about 0.5% to about 15%, or about 0.5% to about 10%, or about 0.5% to about 9%, or about 0.5% to about 8%, or about 0.5% to about 7%, or about 0.5% to about 6%, or about 0.5% to about 5%, or about 0.5% to about 4%, or about 0.5% to about 3%, or about 0.5% to about 2%, or about 0.5% to about 1%.

In some embodiments, the preservative is polyquaternium-1 (polyquad). In some embodiments, the compositions described herein include a preservative in an amount, by weight, of about 0.001% to about 5%, or about 0.001% to about 4%, or about 0.001% to about 3%, or about 0.001% to about 2%, or about 0.001% to about 1%, or about 0.001% to about 0.5%, or about 0.001% to about 0.1%, or about 0.001% to about 0.009%, or about 0.001% to about 0.008%, or about 0.007%, or about 0.001% to about 0.006%, or about 0.001% to about 0.005%.

In an embodiment, the compositions described herein may include a therapeutically effective amount of PS and one or more of a solubilizing agent (e.g., vitamin E TPGS (d-α-tocopheryl polyethylene glycol 1000 succinate)), a sugar alcohol (e.g., mannitol), an acid (e.g., boric acid), and a preservative (e.g., polyquaternium-1 (polyquad)). In some embodiments, such formulations may be used to deliver PS to the retina following topical administration to the eye. In some embodiments, such formulations may be used to deliver PS to the retina in an amount sufficient to treat a retinopathy (i.e., a therapeutically effective amount).

In an embodiment, the compositions described herein may include, by weight, about 0.5% to about 10% PS and one or more of about 0% to about 25% vitamin E TPGS (d-α-tocopheryl polyethylene glycol 1000 succinate), about 0% to about 10% mannitol, about 0% to about 10% boric acid, and about 0% to about 1% polyquaternium-1 (polyquad).

In an embodiment, the compositions described herein may include, by weight, greater than 0.5% PS and one or more of greater than 5% vitamin E TPGS (d-α-tocopheryl polyethylene glycol 1000 succinate), greater than 0.5% mannitol, greater than 0.5% boric acid, and greater than 0.001% polyquaternium-1 (polyquad).

In an embodiment, the compositions described herein may include, by weight, less than 10% PS and one or more of less than 25% vitamin E TPGS (d-α-tocopheryl polyethylene glycol 1000 succinate), less than 10% mannitol, less than 10% boric acid, and less than 1% polyquaternium-1 (polyquad).

In an embodiment, the compositions described herein may include, by weight, about 3.5% PS and one or more of about 16% vitamin E TPGS (d-α-tocopheryl polyethylene glycol 1000 succinate), about 3.18% mannitol, about 1.2% boric acid, and about 0.005% polyquaternium-1 (polyquad).

In an embodiment, the compositions described herein may be semi-solid formulations that include a gel or viscous excipient and PS. Such semi-solid formulations include high viscosity formulations that increase bioavailability by increasing the residence time of the API in the precorneal area. In situ gels are viscous liquids that undergo sol-to-gel transitions upon ocular application because of changes in pH, temperature or electrolyte concentration. Gelling excipients with favorable mucoadhesive properties further increase the residence time. Polymers or gelling excipients employed in developing these drug forms include gellan gum, sodium alginate, poloxamer, and cellulose acetate phthalate. In an embodiment, the compositions described herein may include a PS thermogel using poloxamer 407 or gellan gum, and comprising a therapeutically effective amount of PS.

In some embodiments, the compositions described herein may include a gelling excipient, such as gellan gum or sodium alginate. In some embodiments, the Compostions described herein include a gelling excipient in an amount, by weight, of about 0.5% to about 20%, or about 0.1% to about 15%, or about 0.1% to about 10%, or about 0.1% to about 9%, or about 0.1% to about 8%, or about 0.1% to about 7%, or about 0.1% to about 6%, or about 0.1% to about 5%, or about 0.1% to about 4%, or about 0.1% to about 3%, or about 0.1% to about 2%, or about 0.1% to about 1%, or about 0.1% to about 0.9%, or about 0.1% to about 0.8%, or about 0.1% to about 0.7%, or about 0.1% to about 0.6%, or about 0.1% to about 0.5%.

In some embodiments, the compositions described herein may include a poloxamer. In some embodiments, the compositions described herein include a poloxamer in an amount, by weight, of about 1% to about 75%, or about 1% to about 70%, or about 1% to about 65%, or about 1% to about 60%, or about 1% to about 55%, or about 1% to about 50%, or about 1% to about 45%, or about 1% to about 40%, or about 1% to about 35%, or about 1% to about 30%, or about 1% to about 25%, or about 1% to about 20%, or about 1% to about 15%, or about 1% to about 10%, or about 1% to about 9%, or about 1% to about 8%, or about 1% to about 7%, or about 1% to about 6%, or about 1% to about 5%, or about 1% to about 4%, or about 1% to about 3%, or about 1% to about 2%.

In some embodiments, the compositions described herein include a surfactant, such as Tween 80 or polyoxyl stearate. In some embodiments, the compositions described herein include a surfactant in an amount, by weight, of about 0.01% to about 20%, or about 0.01% to about 15%, or about 0.01% to about 10%, or about 0.01% to about 9%, or about 0.01% to about 8%, or about 0.01% to about 7%, or about 0.01% to about 6%, or about 0.01% to about 5%, or about 0.01% to about 4%, or about 0.01% to about 3%, or about 0.01% to about 2%, or about 0.01% to about 1%, or about 0.01% to about 0.5%, or about 0.01% to about 0.1%, or about 0.01% to about 0.09%, or about 0.01% to about 0.08%, or about 0.07%, or about 0.01% to about 0.06%, or about 0.01% to about 0.05%.

In some embodiments, the compositions described herein include a cyclodextrin, such as (2-hydroxypropyl)-β-cyclodextrin. In some embodiments, the compositions described herein include a cylcodextrin in amount, by weight, of about 0.5% to about 95%, or about 0.5% to about 90%, or about 0.5% to about 85%, or about 0.5% to about 80%, or about 0.5% to about 75%, or about 0.5% to about 70%, or about 0.5% to about 65%, or about 0.5% to about 60%, or about 0.5% to about 55%, or about 0.5% to about 50%, or about 0.5% to about 45%, or about 0.5% to about 40%, or about 0.5% to about 35%, or about 0.5% to about 30%, or about 0.5% to about 25%, or about 0.5% to about 20%, or about 0.5% to about 15%, or about 0.5% to about 10%, or about 0.5% to about 9%, or about 0.5% to about 8%, or about 0.5% to about 7%, or about 0.5% to about 6%, or about 0.5% to about 5%, or about 0.5% to about 4%, or about 0.5% to about 3%, or about 0.5% to about 2%, or about 0.5% to about 1%.

In an embodiment, the compositions described herein may include a therapeutically effective amount of PS and one or more of a gelling excipient (e.g., gellan gum or sodium alginate), a poloxamer, a solubilizing agent (e.g., vitamin E TPGS), a surfactant (e.g., Tween 80 or polyoxyl stearate), a polyether (e.g., a polyethylene glycol, propylene glycol, Cremophor), and a cyclodextrin (e.g., (2-hydroxypropyl)-β-cyclodextrin). In some embodiments, such formulations may allow for delivery of PS to anterior segments of the eye following topical administration. In some embodiments, such formulations may be used to deliver PS to the anterior segments of the eye in an amount sufficient to treat a disease described herein that is associated with such anterior segments of the eye (i.e., a therapeutically effective amount).

As used herein, an amount described as "about 0%," by weight, is understood to be an amount that is greater than 0%.

In an embodiment, the compositions described herein may include a therapeutically effective amount of PS and one or more of gellan gum, vitamin E TPGS, and a (2-hydroxypropyl)-β-cyclodextrin.

In an embodiment, the compositions described herein may include, by weight, about 0.5% to about 10% PS and one or more of about 0% to about 5% gellan gum, about 0% to about 20% vitamin E TPGS, and about 0% to about 20% (2-hydroxypropyl)-β-cyclodextrin.

In an embodiment, the compositions described herein may include, by weight, greater than 0.5% PS and one or more of greater than 0.1% gellan gum, greater than 1% vitamin E TPGS, and greater than 5% (2-hydroxypropyl)-β-cyclodextrin.

In an embodiment, the compositions described herein may include, by weight, less than 10% PS and one or more of less than 5% gellan gum, less than 20% vitamin E TPGS, less than 20% (2-hydroxypropyl)-β-cyclodextrin.

In an embodiment, the compositions described herein may include, by weight, about 2.4% to about 3% PS and one or more of about 0.5% gellan gum, about 5% vitamin E TPGS, about 10% (2-hydroxypropyl)-β-cyclodextrin.

In an embodiment, the compositions described herein may include, by weight, about 2.4% to about 3% PS and one or more of about 0.4% gellan gum, about 10% vitamin E TPGS, about 5% (2-hydroxypropyl)-β-cyclodextrin.

In an embodiment, the compositions described herein may include a therapeutically effective amount of PS and one or more of sodium alginate, vitamin E TPGS, a (2-hydroxypropyl)-β-cyclodextrin, Tween (e.g., Tween 80), poly(ethylene glycol) (PEG) (e.g., PEG 400), and polyoxyl stearate.

In an embodiment, the compositions described herein may include, by weight, about 0.5% to about 10% PS and one or more of about 0% to about 5% sodium alginate, about 0% to about 20% vitamin E TPGS, and about 0% to about 20% (2-hydroxypropyl)-β-cyclodextrin.

In an embodiment, the compositions described herein may include, by weight, greater than 0.5% PS and one or more of greater than 0.1% sodium alginate, greater than 1% vitamin E TPGS, and greater than 5% (2-hydroxypropyl)-β-cyclodextrin.

In an embodiment, the compositions described herein may include, by weight, less than 10% PS and one or more of less than 5% sodium alginate, less than 20% vitamin E TPGS, less than 20% (2-hydroxypropyl)-β-cyclodextrin.

In an embodiment, the compositions described herein may include, by weight, about 3% PS and one or more of about 1.5% sodium alginate, about 5% vitamin E TPGS, about 10% (2-hydroxypropyl)-β-cyclodextrin.

In an embodiment, the compositions described herein may include, by weight, about 0.5% to about 10% PS and one or more of about 0% to about 5% sodium alginate, about 0% to about 25% Tween 80, about 0% to about 20% (2-hydroxylpropyl)-β-cyclodextrin, about 0% to about 20% PEG 400, and about 0% to about 10% polyoxyl stearate.

In an embodiment, the compositions described herein may include, by weight, greater than 0.5% PS and one or more of greater than 1% sodium alginate, greater than 1% Tween 80, greater than 1% (2-hydroxylpropyl)-β-cyclodextrin, greater than 1% PEG 400, and greater than 1% polyoxyl stearate.

In an embodiment, the compositions described herein may include, by weight, less than 10% PS and one or more of less than 5% sodium alginate, less than 25% Tween 80, less than 20% (2-hydroxylpropyl)-β-cyclodextrin, less than 20% PEG 400, and less than 10% polyoxyl stearate.

In an embodiment, the compositions described herein may include, by weight, about 3% PS and one or more of about 1.5% sodium alginate, about 15% Tween 80, about 10% (2-hydroxylpropyl)-β-cyclodextrin, about 10% PEG 400, and about 5% polyoxyl stearate.

In an embodiment, the compositions described herein may include, by weight, about 1% to about 5% PS and one or more of about 50% to about 90% (2-hydroxypropyl)-β-cyclodextrin (HP-β-CD), about 0.05% to about 1% cremophor EL (F1), and about 0.5% to about 5% Tween 80 (F2).

In an embodiment, the compositions described herein may include, by weight, about 1% to about 5% PS and one or more of about 50% to about 90% (2-hydroxypropyl)-β-cyclodextrin (HP-β-CD), and about 0.05% to about 1% cremophor EL (F1).

In an embodiment, the compositions described herein may include, by weight, about 1% to about 5% PS and one or more of about 50% to about 90% (2-hydroxypropyl)-β-cyclodextrin (HP-β-CD), and about 0.5% to about 5% Tween 80 (F2).

In an embodiment, the compositions described herein may include, by weight, about 3 to about 4% PS and one or more of about 80% (2-hydroxypropyl)-β-cyclodextrin (HP-β-CD), and about 0.1% cremophor EL (F1).

In an embodiment, the compositions described herein may include, by weight, about 3 to about 4% PS and one or more of about 80% (2-hydroxypropyl)-β-cyclodextrin (HP-β-CD), and about 1% Tween 80 (F2).

In an embodiment, the compositions described herein may include, by weight, about 1% to about 10% PS and one or more of about 1% to about 40% Poloxamer 407 and about 1% to about 20% vitamin E TPGS.

In an embodiment, the compositions described herein may include, by weight, greater than 1% PS and one or more of greater than 1% Poloxamer 407 and greater than 1% vitamin E TPGS.

In an embodiment, the compositions described herein may include, by weight, less than 10% PS and one or more of less than 40% Poloxamer 407 and less than 20% vitamin E TPGS.

In an embodiment, the compositions described herein may include, by weight, about 5.4% PS and one or more of about 20% Poloxamer 407 and about 12% vitamin E TPGS.

In an embodiment, the compositions described herein may be multicompartment formulations of PS such as, for example, nanoparticles, liposomes, dendrimers, or niosomes that may include PS. Nanoparticles are polymeric carriers, which improve bioavailability thanks to increased corneal penetration and a larger surface area for dissolution. A relative limitation of nanoparticles is their low capacity. Liposomes are limited by their suboptimal stability, high cost and challenging technology for their large-scale production. Niosomes and discosomes are two-layered carriers, which increase API bioavailability by extending its pre-corneal residence time. In an embodiment, the compositions described herein include nanoparticles that comprise a therapeutically effective amount of PS.

In an embodiment, the compositions described herein may include a nanopartical formulation comprising a therapeutically effective amount of PS. In some embodiment, the nanoparticle formulation may include poly(ethylene glycol) (PEG) nanoparticles. In some embodiments the nanoparticle formulation may include methoxy poly(ethylene glycol)-poly(lactide) (mPEG-PLA) nanoparticles. In some embodiments, such formulations may allow for delivery of PS to anterior segments of the eye following topical administration. In some embodiments, such formulations may be used to deliver PS to the anterior segments of the eye in an amount sufficient to treat a disease described herein that is associated with such anterior segments of the eye (i.e., a therapeutically effective amount).

In an embodiment, the compositions described herein may include a nanoparticle formulation comprising, by weight, about 1% to about 5% PS and about 90% to about 98% mPEG-PLA.

In an embodiment, the compositions described herein may include a nanoparticle formulation comprising, by weight, about 3% to about 3.5% PS and about 96.5% to about 97% mPEG-PLA.

In preferred embodiments, the invention provides a pharmaceutical composition for injection, such as intraocular injection, containing a compound of the invention, such as a compound of formula (III) or formula (IV) described herein, and a pharmaceutical excipient suitable for injection. Components and amounts of compounds in the compositions are as described herein.

The forms in which the compositions of the invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol, such as polyethylene glycol, (and suitable mixtures thereof (e.g., PEG-PLA)), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, and thimerosal.

Sterile injectable solutions are prepared by incorporating a compound of the invention, such as a compound of formula (III) or formula (IV) described herein, in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical compositions may also be prepared from compositions described herein and one or more pharmaceutically acceptable excipients suitable for ocular or intraocular administration. Preparations for such pharmaceutical compositions are well-known in the art. See, e.g., Anderson, et al., eds., Handbook of Clinical Drug Data, Tenth Edition, McGraw-Hill, 2002; and Pratt and Taylor, eds., Principles of Drug Action, Third Edition, Churchill Livingston, N.Y., 1990, each of which is incorporated by reference herein in its entirety.

Administration of a compound of the invention, such as a compound of formula (III) or formula (IV) described herein, or a pharmaceutical composition of these compounds can be effected by any method that enables delivery of the compounds to the site of action. These methods include parenteral injection (including intraocular injection) or topical application (e.g., application to a surface of the eye).

In some embodiments, administration of a compound of formula (III) or formula (IV) described herein or a pharmaceutical composition of these compounds can be effected by any method that enables delivery of the compounds to the site of action, which may include oral routes, intraduodenal routes, parenteral injection (including intravenous, intraarterial, subcutaneous, intramuscular, intravascular, intraperitoneal or infusion), topical (e.g., transdermal application, ocular application), rectal administration, via local delivery by catheter or stent or through inhalation. In some embodiments, the compound of formula (III) or formula (IV) described herein can also be administered intraadiposally or intrathecally.

Exemplary administration forms (e.g., parenteral, topical, or by drops) include solutions or suspensions of a compound of formula (III) or formula (IV) in sterile aqueous solutions, for example, aqueous propylene glycol or dextrose solutions. Such dosage forms can be suitably buffered, if desired.

The invention also provides kits. The kits include a compound of formula (III) or formula (IV) described herein in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient (e.g., an antibiotic). In some embodiments, the compound of formula (III) or formula (IV) described herein and another active pharmaceutical ingredient are provided as separate compositions in separate containers within the kit. In some embodiments, the compound of formula (III) or formula (IV) and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

The kits described above are preferably for use in the treatment of the diseases and conditions described herein. In a preferred embodiment, the kits are for use in the treatment of dry eye disease or diabetic retinopathy.

The amounts of a compound of formula (III) or formula (IV) described herein administered will be dependent on the human or mammal being treated, the severity of the disorder or condition, the rate of administration, the disposition of the compounds and the discretion of the prescribing physician. However, an effective dosage of each is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day. The dosage of a compound of formula (III) or formula (IV) described herein may be provided in units of mg/kg of body mass or in $mg/m^2$ of body surface area.

In some embodiments, a compound of formula (III) or formula (IV) described herein is administered in multiple doses. In a preferred embodiment, a compound of formula (III) or formula (IV) described herein is administered in multiple doses. Dosing may be once, twice, three times, four times, five times, six times, or more than six times per day. Dosing may be once a month, once every two weeks, once a week, or once every other day. In other embodiments, a compound of formula (III) or formula (IV) described herein is administered about once per day to about 6 times per day. In some embodiments, a compound of formula (III) or formula (IV) described herein is administered once daily, while in other embodiments, a compound of formula (III) or formula (IV) described herein is administered twice daily, and in other embodiments a compound of formula (III) or formula (IV) described herein is administered three times daily.

Administration a compound of formula (III) or formula (IV) described herein may continue as long as necessary. In some embodiments, a compound of formula (III) or formula (IV) described herein is administered for more than 1, 2, 3, 4, 5, 6, 7, 14, or 28 days. In some embodiments, a compound of formula (III) or formula (IV) described herein is administered for less than 28, 14, 7, 6, 5, 4, 3, 2, or 1 day. In some embodiments, a compound of formula (III) or formula (IV) described herein is administered chronically on an ongoing basis—e.g., for the treatment of chronic effects. In another embodiment, the administration of a compound of formula (III) or formula (IV) described herein continues for less than about 7 days. In yet another embodiment, the administration continues for more than about 6, 10, 14, 28 days, two months, six months, or one year. In some cases, continuous dosing is achieved and maintained as long as necessary.

In some embodiments, an effective dosage of a compound of formula (III) or formula (IV) described herein is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg.

In some embodiments, an effective dosage of a compound of formula (III) or formula (IV) described herein is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some instances, dosage levels below the lower limit of the aforesaid ranges may be more than adequate, while in other cases still larger doses may be employed without causing any harmful side effect—e.g., by dividing such larger doses into several small doses for administration throughout the day.

In some embodiments, the compounds described herein are administered topically, e.g., in eye drops. In some embodiments, the therapeutically effective dose for a compound of formula (III) or formula (IV) may be at least about 0.75 mg, at least about 1.5 mg, or at least about 2 mg. In some embodiments, the therapeutically effective dose for a compound of formula (III) or formula (IV) may be about 0.75 mg, about 1.5 mg, or about 2 mg. In some embodiments, the therapeutically effective dose for a compound of formula (III) or formula (IV) is no more than about 0.75 mg, no more than about 1.5 mg, or no more than about 2 mg.

An effective amount of a compound of formula (III) or formula (IV) described herein may be administered in either single or multiple doses by any of the accepted modes of administration of agents having similar utilities, including by intraocular injection or topical application.

In certain embodiments, a substantial portion of a compound described herein (e.g., a compound of formula III or formula IV) that is distributed to the tissues after 1 hour, as determined by HPLC, is in a particular, or targeted, tissue or area. In certain embodiments, greater than 30% of the total compound in the cornea, conjunctiva, aqueous humor, vitreous body, retina, choroid, sclera, lacrimal gland and lens (referred to as tissues or areas of the eye) can be found in a single tissue or area of the eye. In certain embodiments, greater than 30% of the total compound in the cornea, conjunctiva, aqueous humor, vitreous body, retina, choroid, sclera, lacrimal gland and lens can be found in a single tissue or area. In certain embodiments, greater than 40% of the total compound in the cornea, conjunctiva, aqueous humor, vitreous body, retina, choroid, sclera, lacrimal gland and lens can be found in a single tissue or area. In certain embodiments, greater than 50% of the total compound in the cornea, conjunctiva, aqueous humor, vitreous body, retina, choroid, sclera, lacrimal gland and lens can be found in a single tissue or area. In certain embodiments, greater than 60% of the total compound in the cornea, conjunctiva, aqueous humor, vitreous body, retina, choroid, sclera, lacrimal gland and lens can be found in a single tissue or area. In certain embodiments, greater than 70% of the total compound in the cornea, conjunctiva, aqueous humor, vitreous body, retina, choroid, sclera, lacrimal gland and lens can be found in a single tissue or area. In certain embodiments, greater than 80% of the total compound in the cornea, conjunctiva, aqueous humor, vitreous body, retina, choroid, sclera, lacrimal gland and lens can be found in a single tissue or area. In certain embodiments, greater than 90% of the total compound in the cornea, conjunctiva, aqueous humor, vitreous body, retina, choroid, sclera, lacrimal gland and lens can be found in a single tissue or area.

In some embodiments, the compounds described herein are delivered to mammals for the treatment of disease. A person having ordinary skill in the art would understand that, in certain embodiments, dosages of such compounds may be adjusted depending upon the mammal to be treated. For example, in certain embodiments, the treatment of rabbits is described herein and such dosages may or may not be revised upon the administration of the compounds of the invention to a human. However, a person having ordinary skill in the art may, if necessary, convert the dosages provided herein as set forth in Guidance for Industry: Estimating the Maximum Safe Starting Dose in Initial Clinical Trials for Therapeutics in Adult Healthy Volunteers, U.S. Department of Health and Human Services, Food and Drug Administration, Center for Drug Evaluation and Research (CDER), July 2005, the entirety of which is incorporated herein by reference. In some embodiments, a human equivalent dose (HED) may be determined from an animal dose, the animal dose may be multiplied by the following conversion factors, to provide units in mg/kg: mouse=0.08, hamster=0.13, rat=0.16, ferret=0.19, guinea pig=0.22, rabbit=0.32, dog=0.54, monkey=0.32, marmoset=0.16, squirrel monkey=0.19, baboon=0.54, micropig=0.73, and mini-pig=0.95. The foregoing conversion factors are exemplary and in no way limit the dosages provided herein as would be understood by a person having ordinary skill in the art.

Pharmaceutical Packages

In some embodiments, the present invention provides a pharmaceutical package comprising:

a formulation comprising a compound selected from the compounds described herein; and a dispenser, such as an eye dropper; wherein when the dispenser is used to deliver the formulation to an eye, one or two drops of the formulation comprise a dose of a compound described herein that is therapeutically effective for treating an ophthalmic condition.

In some embodiments, the ophthalmic condition is dry-eye disease. The dose may be a dry-eye dose that is less than an analgesic dose.

In some embodiments, the ophthalmic condition is pain or inflammation. The dose may be an anti-inflammatory dose that is less than an analgesic dose, or the dose may be an analgesic dose.

In some embodiments, the ophthalmic condition is pain and/or inflammation following ocular surgery. The dose may be an anti-inflammatory dose that is less than an analgesic dose, or the dose may be an analgesic dose.

In some embodiments, the ophthalmic condition is conjunctivitis or uveitis. The dose may be an anti-inflammatory dose that is less than an analgesic dose, or the dose may be an analgesic dose.

In some embodiments, the ophthalmic condition is pterygium. A compound of Formula I may be administered locally to the surface of the eye over the pterygium as eye drops; or as an ointment; or as a spray; or by microinjection into the pterygium.

In some embodiments, the ophthalmic condition is mechanical trauma or chemical injury to the eye. A compound of Formula I may be administered locally to the affected area as eye drops; or as an ointment; or as a spray; or in a suitable slow-release formulation.

In some embodiments, the ophthalmic condition is cystoid macular edema or diabetic retinopathy. In these embodiments, the compound may be administered locally to the surface of the eye, delivered to the posterior part of the eye by direct injection, or deposited within the eye in a slow-release formulation. The dose may be an effective dose that is less than an analgesic dose.

In some embodiments, the ophthalmic condition is Sjogren's syndrome. According to these embodiments, the compound of Formula I may be administered locally to the surface of the eye; or to the lacrimal gland after its application to the skin in proximity to the lacrimal gland; or by direct injection to the lacrimal gland; or deposited into or near the lacrimal gland preferably formulated in a manner ensuring its slow-release. The dose may be an effective dose that is less than an analgesic dose.

In some embodiments, the ophthalmic condition is pterygium. According to these embodiments, the compound may be administered locally to the surface of the eye over the pterygium as eye drops; or as an ointment; or as a spray; or by microinjection into the pterygium. The dose may be an effective dose that is less than an analgesic dose.

In some embodiments, the ophthalmic condition is mechanical trauma or chemical injury to the eye. According to these embodiments, the compound may be administered locally to the affected area as eye drops; or as an ointment; or as a spray; or in a suitable slow-release formulation. According to these embodiments, the dose may be an effective dose that is less than an analgesic dose.

In some embodiments, when the dispenser is used to deliver the formulation to an eye, one drop of the formulation comprises 0.75 mg, 1.5 mg, 2 mg, 3 mg, 4 mg, 5 mg, 6 mg, 7 mg, 8 mg, 9 mg, or 10 mg of the compound. In some preferred embodiments, when the dispenser is used to deliver the formulation to an eye, one drop of the formulation comprises 0.75 mg of the compound. In some preferred embodiments, when the dispenser is used to deliver the formulation to an eye, one drop of the formulation comprises 2 mg of the compound.

In some embodiments, the pharmaceutical package further comprises instructions for the administration of the formulation to treat an ophthalmic condition, such as DED, pain, inflammation, or conjunctivitis, uveitis, cystoid macular edema, Sjogren syndrome, pterygium, diabetic retinopathy, trauma or chemical injury to the eye.

In certain embodiments, the pharmaceutical package comprises instructions for the administration of the formulation comprising a compound described herein (i.e., a compound of Formula I, a compound of Formula II, a compound selected from compounds 1-120, or a compound selected from compounds 121-136) conjointly with an agent or non-chemical method suitable for the treatment of an ophthalmic condition as described above. In certain embodiments, the pharmaceutical package further comprises a second formulation comprising an agent suitable for the treatment of an ophthalmic condition as mentioned above.

In some embodiments, the present invention provides a pharmaceutical package comprising:

one or more single dosage forms each comprising a formulation comprising a compound described herein (e.g., compound of Formula I, a compound of Formula II, a compound selected from compounds 1-120, or a compound selected from compounds 121-136); and instructions for administering the single dosage forms for the treatment of an ophthalmic condition.

In certain embodiments, the pharmaceutical package further comprises instructions for the administration of the one or more single dosage forms each comprising a formulation comprising a compound described herein (i.e., a compound of Formula I, a compound of Formula II, a compound selected from compounds 1-120, or a compound selected from compounds 121-136) conjointly with an agent or non-chemical method suitable for the treatment of an ophthalmic condition as mentioned above. In certain embodiments, the kit further comprises one or more single dosage forms of an agent suitable for the treatment of an ophthalmic condition as mentioned above.

In some embodiments, the present invention provides a pharmaceutical package comprising:

one or more single dosage forms each comprising an agent suitable for the treatment of an ophthalmic condition as described above; and instructions for the administration of the one or more single dosage forms with a compound described herein (i.e., a compound of Formula I, a compound of Formula II, a compound selected from compounds 1-120, or a compound selected from compounds 121-136) for treating or preventing an ophthalmic condition.

In some embodiments, the present invention provides a pharmaceutical package comprising:

a first formulation comprising an agent suitable for the treatment of an ophthalmic condition as described above; and instructions for the administration of the first pharmaceutical formulation and a second formulation comprising a compound described herein (i.e., a compound of Formula I, a compound of Formula II, a compound selected from compounds 1-120, or a compound selected from compounds 121-136) for treating or preventing an ophthalmic condition.

EXAMPLES

The invention now being generally described, it will be more readily understood by reference to the following examples, which are included merely for purposes of illustration of certain aspects and embodiments of the present invention, and are not intended to limit the invention.

Example 1

General Methods

To assess the efficacy of PS on DED an improved concanavalin A model was used. In the concanavalin A model, dry eye is induced by injecting the lacrimal glands of a mammal with concanavalin A, a selective T cell mitogen that induces a lymphocytic infiltrate in these glands. The concanavalin A model is generally described in (Barabino S. Animal models of dry eye. Arch Soc Esp Oftalmol. 2005; 80(12):693-4). Concanavalin A was injected to the lacrimal glands under ultrasound guidance, thus eliminating injections to the vicinity of the gland (as opposed to the gland itself). The head and the tail of the major lacrimal gland of the rabbit were injected separately. The dose of concanavalin A was optimized for DED signs.

In the testing described below, four markers of DED are monitored: the tear break up time (TBUT), the Schirmer test, tear osmolarity, and tear lactoferrin levels. All assays were performed at the same clock time (±1 hr) to avoid assay variability on account of circadian variations.

Example 2

Efficacy of PS on DED

In an efficacy experiment using the concanavalin A model, one group of rabbits was treated with compound 5, also known as phosphosulindac and abbreviated as PS, 1.5% eye drops and one group with vehicle. As shown in Table 1, TBUT, tear osmolarity and tear lactoferrin levels showed a strong therapeutic response to PS while the Schirmer's test also improved (significant for trend). It is thus clear that PS applied topically suppresses DED.

TABLE 1

The effect of PS on DED in rabbits

| | TBUT, seconds | | Schirmer test, mm | | Tear osmolarity, Osm/L Mean ± SEM | | Tear lactoferrin, ng/mg protein | |
|---|---|---|---|---|---|---|---|---|
| | Baseline | Day 13 | Baseline | Day 11 | Baseline | Day 13 | Baseline | Day 13 |
| Vehicle | 60.0 ± 0.0 | 12.9 ± 2.7 | 15.5 ± 1.9 | 7.6 ± 0.6 | 303.6 ± 3.7 | 317.8 ± 2.7 | 3.09 ± 0.4 | 2.71 ± 0.1 |
| PS | 52.3 ± 4.6 | 56.0 ± 4.0 | 14.6 ± 0.9 | 9.5 ± 1.0 | 298.0 ± 4.6 | 307.8 ± 3.8 | 3.09 ± 0.4 | 3.19 ± 0.2 |
| p value* | | <0.0001 | | <0.1 | | <0.03 | | <0.04 |

*comparison between vehicle control and PS-treated groups.

Example 3

General Safety Data

There was no evidence of topical or systemic toxicity form PS in rabbits, including no changes in intraocular pressure during 2 weeks of daily treatment with PS 3.6% eye drops.

Example 4

No Corneal Melt

Careful ophthalmological examination of the eyes of rabbits treated for up to 3 weeks with PS, revealed no evidence of keratitis or corneal melting.

Example 5

Comparison of Effects of PS with Ketorolac on $PGE_2$ Levels

The effects of PS, ketorolac and dicofenac (the latter two ophthalmic NSAIDs known to induce corneal melt) on the tear levels of $PGE_2$ in rabbits with concanavalin A-induced dry eye were compared. Three eye drops of PS 1.5% or of commercially available ketorolac 0.5% were given at 0 time, and 1 h later to rabbits with concanavalin A-induced DED. Tears were obtained at 2 h and the levels of $PGE_2$ were determined by ELISA. $PGE_2$ in tears of naïve rabbits (not exposed to concanavalin A nor treated) was also measured. The $PGE_2$ levels (mean±SEM) were: Naïve, 110.4±12.6 ng/ml; PS-treated, 115.4±15.8 ng/ml; Ketorolac-treated, 77.7±8.7 ng/ml. The difference in PS vs. ketorolac was significant, p<0.02; as was the difference in ketorolac vs naïve, p<0.03. Regarding this parameter, PS differs radically form ketorolac, which induces corneal melt.

Levels of $PGE_2$ in the corneas of three groups of rabbits were determined by ELISA. Rabbits were treated with PS 1.6% or ketorolac 0.5% eye drops topically applied to their eyes or were not treated (naïve group). Results in pg/mg protein (mean±SEM). Naïve=787.3±96.3; PS=880.6±110.3; Ketrolorac=247.2±187.4 (p<0.01 vs PS).

Rabbits with DED induced by concanavalin A as above were treated for 6 days with vehicle, or PS 2.3% or ketorolac 0.5% or diclofenac 0.1%. Compared to the vehicle group, on day 6 the $PGE_2$ levels in the cornea were 106% of the vehicle value in the PS group (not a statistically significant difference), 1.3% in the ketorolac group (p<0.0001 vs. vehicle, and 2.3% in the diclofenac group (p<0.0001 vs. vehicle).

$PGE_2$ is a cytoproctective agent for the corneal epithelium. Diminished levels of $PGE_2$ in the cornea facilitate the development of corneal melt, most likely representing the initiating factor in the formation of corneal erosions. A subsequent step is the release of MMPs that hydrolyze the collagen fibrils making up most of the cornea. The breakdown of collagen completes the process of corneal melt with serious consequences for the function of the eye. Corneal perforation that may ensue as the culmination of corneal melt, can lead to loss of vision or even of the eye in case of severe complications.

Example 6

Suppression of MMPs

In an in vitro assay with purified MMP-1 (collagenase I) as a substrate it was shown that PS inhibited collagenase activity with an $IC_{50}$ of <100 nM. In cultured human conjunctiva cells, PS suppressed MMP-1 by 75%-86%. In the lacrimal glands of rabbits with DED treated with PS eye drops, PS suppressed MMP-9 levels by 27% compared to vehicle treated rabbits (2.20±0.24 vs. 1.66±0.20 ng/mg protein; p<0.05; mean±SEM).

The general activity of MMPs was determined in the corneas of three groups of rabbits. This MMP activity assay employs a fluorescence resonance energy transfer (FRET) peptide as a generic MMP indicator. Rabbits were treated with PS 1.6% or ketorolac 0.5% eye drops topically applied to their eyes or were not treated (naïve group). Results in relative fluorescence units (RFU)/mg protein (mean±SEM). Naïve=1,328±123; PS=749±218; Ketoroloac=1,272±106 (p<0.03 vs PS).

Example 7

Treatment of Ocular Pain and Inflammation

The analgesic effect of PS was determined by measuring the corneal touch threshold (CTT) using the Luneau Cochet-Bonnet Aeshesiometer (Western Ophthalmics, Lynwood, Wash.), an adjustable nylon monofilament with a defined diameter, which is applied in different lengths to the center of the cornea. This device is generally described in Lima L, Lange R R, Turner-Giannico A, Montiani-Ferreira F. Evaluation of standardized endodontic paper point tear test in New Zealand white rabbits and comparison between corneal sensitivity followed tear tests. Vet Ophthalmol. 2015; 18 Suppl 1:119-24.

A stimulus produced by the filament that reaches the CTT induces a corneal reflex, consisting of prompt eyelid closure. The CTT is quantified as centimeter length of the filament necessary to cause the blink reflex.

The CTT is determined before (baseline) and at various time points after the application of the test compound (PS). PS was formulated either in β-cyclodextrin (42 or 8 mg/ml) or in a nanocarrier (19 mg/ml). The test drug was formulated in a nanocarrier by the emulsion and evaporation method (Vauthier C, Bouchemal K. Methods for the Preparation and Manufacture of Polymeric Nanoparticles. Pharmaceutical Research; 2009; 26:1025-1058). The formulated stable drug suspension consisted of polylactic acid and polyethylene glycol (PLLA(10k)-PEG(2k)); sodium cholate; and PS. The vehicle control was either β-cyclodextrin or the nanocarrier without PS. Commercially available lidocaine 1% was used as a positive control.

To each eye of adult New Zealand white rabbits was applied 325 μL drops of PS or vehicle or lidocaine, with 5 minutes between each drop. The time of the last drop was taken as the 0 time.

Table 2 demonstrates the analgesic effect of PS, which is both time- and dose-dependent.

TABLE 2

Corneal touch threshold (CTT) values in response to topical treatment with PS

| Time, min | Control | PS 42 mg/ml | PS 19 mg/ml | PS 8 mg/ml | Lidocaine 1% |
|---|---|---|---|---|---|
| baseline | 5.9 ± 0.2 | 5.9 ± 0.2 | 5.9 ± 0.3 | 5.9 ± 0.3 | 6.0 ± 0.0 |
| 1 | 5.9 ± 0.2 | 2.7 ± 1.0 | 5.4 ± 0.6 | 5.3 ± 0.7 | 1.5 ± 1.3 |
| 5 | 5.9 ± 0.2 | 3.1 ± 1.2 | 5.1 ± 0.8 | 5.4 ± 0.8 | 2.3 ± 1.5 |
| 10 | 5.6 ± 0.3 | 3.7 ± 1.3 | 5.3 ± 0.8 | 5.6 ± 0.5 | 3.1 ± 1.9 |
| 20 | 5.8 ± 0.4 | 4.1 ± 1.4 | 5.5 ± 0.7 | 5.6 ± 0.5 | 4.0 ± 1.3 |
| 30 | 5.9 ± 0.2 | 5.1 ± 1.0 | 5.9 ± 0.2 | 5.9 ± 0.3 | 5.8 ± 0.6 |
| 45 | 5.9 ± 0.2 | 5.6 ± 0.7 | 5.9 ± 0.4 | 5.9 ± 0.3 | 5.8 ± 0.6 |
| 60 | 5.9 ± 0.2 | 5.9 ± 0.2 | 5.9 ± 0.2 | 5.9 ± 0.3 | 6.0 ± 0.0 |

Example 8

PS as an Efficacious Treatment of Dry Eye in Rabbits

Phospho-sulindac (PS) is a small molecule whose potential clinical applications have been studied. PS is not a prodrug of the NSAID sulindac as the entire PS molecule is required for its pharmacological activity. Here, the potential efficacy of PS in DED is explored.

Various animal models of DED have been reported. In general, mouse models are commonly used in mechanistic studies because of the availability of transgenic strains and relevant antibodies. However, rabbit or dog models are more suitable for the study of dry eye signs and for therapeutic studies, as their eyes are closer to human in size, their ocular surface is easily accessible, and they can have decreased tear production and significant ocular surface changes, recapitulating to a large extent the human disease.

Initially, several DED animal models were experimented with, including benzalkonium and atropine, and their reported limitations were encountered. A clinically relevant short-term rabbit model of DED developed by Nagelhout et al. was focused upon in order to advance drug discovery. In this model, injection of the inferior lacrimal gland (ILG) with the T-cell mitogen Concanavalin A (Con A) led to a pronounced inflammatory process (dacryoadenitis) with elevated levels of MMP-9 and cytokines IL-10, IL-8, and TGF-β1 in both the lacrimal gland and cornea. The dacryoadenitis suppresses tear production leading to ocular inflammation with attendant changes in clinical parameters of DED. An excellent choice of this model was the use of rabbits, whose eyes, as opposed to those of mice and rats, are closer to the human in size and other features. This model received some validation from reports that anti-inflammatory agents such as dexamethasone reversed clinical manifestations of DED in these rabbits.

Several limitations of this model were observed, mainly lack of reproducibility and the short duration of dry eye (acute model). The former largely stems from the relatively blind injection of Con A into the lacrimal gland, variations in animal anatomy, as well as compensatory tear production from not injected portions of the lacrimal gland system. We have overcome these limitations in our refined model.

The main improvements upon the original Con A-based method brought about our approach are provided herein.

Figure 2:
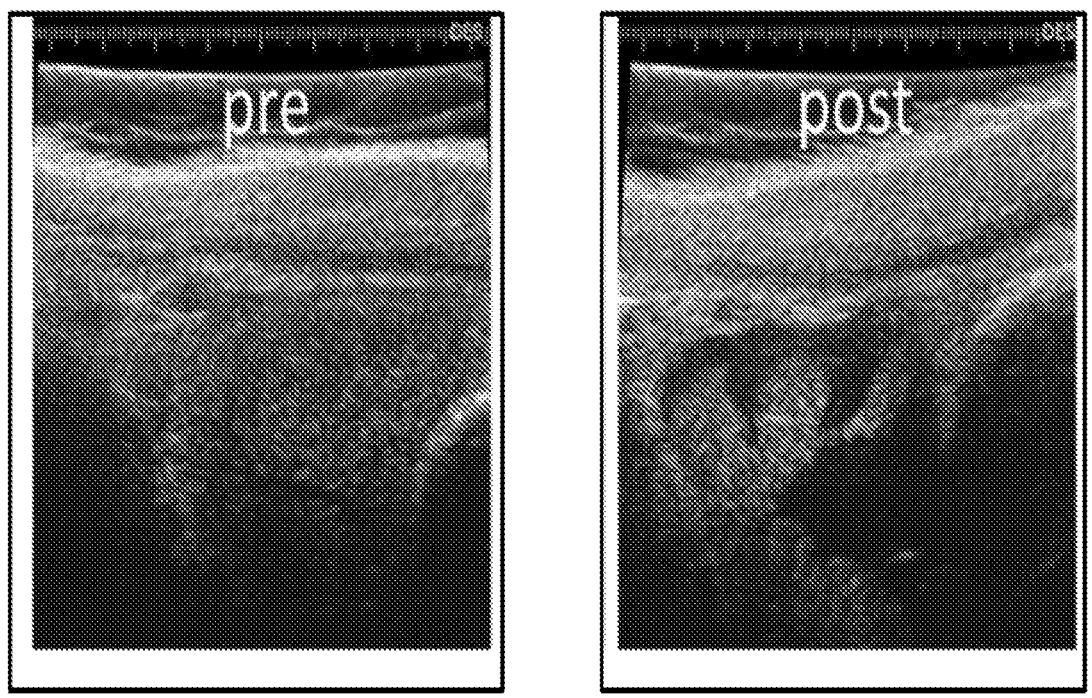
FIG. 2 illustrates ultrasonographic images of the head of the ILG before and after injection of Con A. The characteristic hypoechoic space seen in the post injection image confirms the success of the injection.

Con A was injected under ultrasound guidance into all the lacrimal glands and the success of the injection was verified by a post-injection ultrasound image (see FIG. 1 and FIG. 2). As observed, the size of the inferior lacrimal glands of rabbits varies 4.1 fold between the smallest and the largest (n=42). This variation explains why the blind injections recommended in the original method are often unsuccessful. This was confirmed by mixing the Con A solution with methylene blue and tracking its course after injection. In about ⅓ of the cases, Con A ended up outside the gland. Rabbits receive three Con A injections, one each into the inferior lacrimal gland (ILG), the palpebral portion of the of the superior lacrimal gland (PSLG), and the orbital portion of the SLG (OSLG).

Injecting all the lacrimal glands and not only the inferior lacrimal gland maximized the suppression of tear production, as it was observed that following the injection of Con A to only one, the remaining lacrimal gland could compensate for dry eye by overproducing tears.

Figure 3:
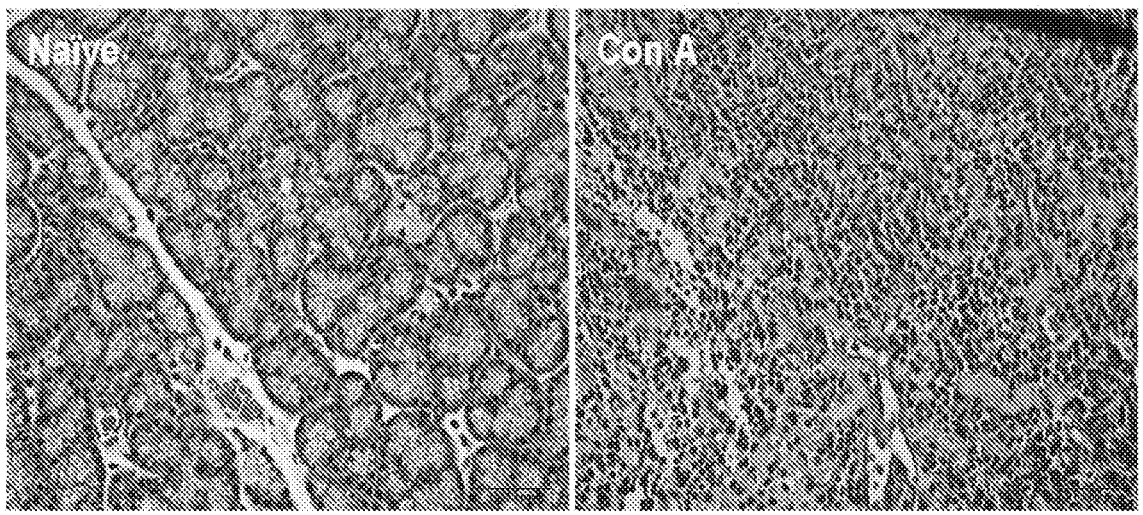
FIG. 3 illustrates that Con A induces inflammation in the lacrimal gland. Microtome sections of the head of the ILG from a naïve and a Con A-injected rabbit stained with H&E.

Con A induced a strong inflammatory response in the lacrimal glands characterized by a dense lymphocytic infiltrate (FIG. 3). The inflammation was followed by reduced tear production evidenced by significantly reduced STT values.

Four parameters of efficacy were evaluated instead of the usual one or two. They include (a) the tear break up time (TBUT), determined using 0.2% fluorescein over the eye and recording the time taken to develop black dots, lines or obvious disruption of the fluorescein film; (b) tear osmolarity, measured using TearLab Osmolarity Test and following the manufacturer's instructions (TearLab Corp., San Diego, Calif.); (3) Schirmer tear test (STT), determined using Schirmer strips (EagleVision, Denville, N.J.) inserted between the cornea and the palpebral conjunctiva at the mid-point of the lower lid and measuring the length of moistened strip at 5 min; and (4) tear lactoferrin levels measured by ELISA kit (MyBiosource, San Diego, Calif.) following the instructions of the manufacturer. All four have been used in clinical practice and correlate with the clinical activity of the disease. The STT is the least reliable and, as result, it is clinically used less than half as frequently as TBUT.

The injections of Con A to the lacrimal glands were repeated weekly as needed. When longer than a 1-week periods of study are needed, repeat injections prolong dry eye for at least 3 weeks, making the originally acute model chronic.

This model is robust and can be used to reliably study DED and its response to therapeutic agents.

Figure 4:
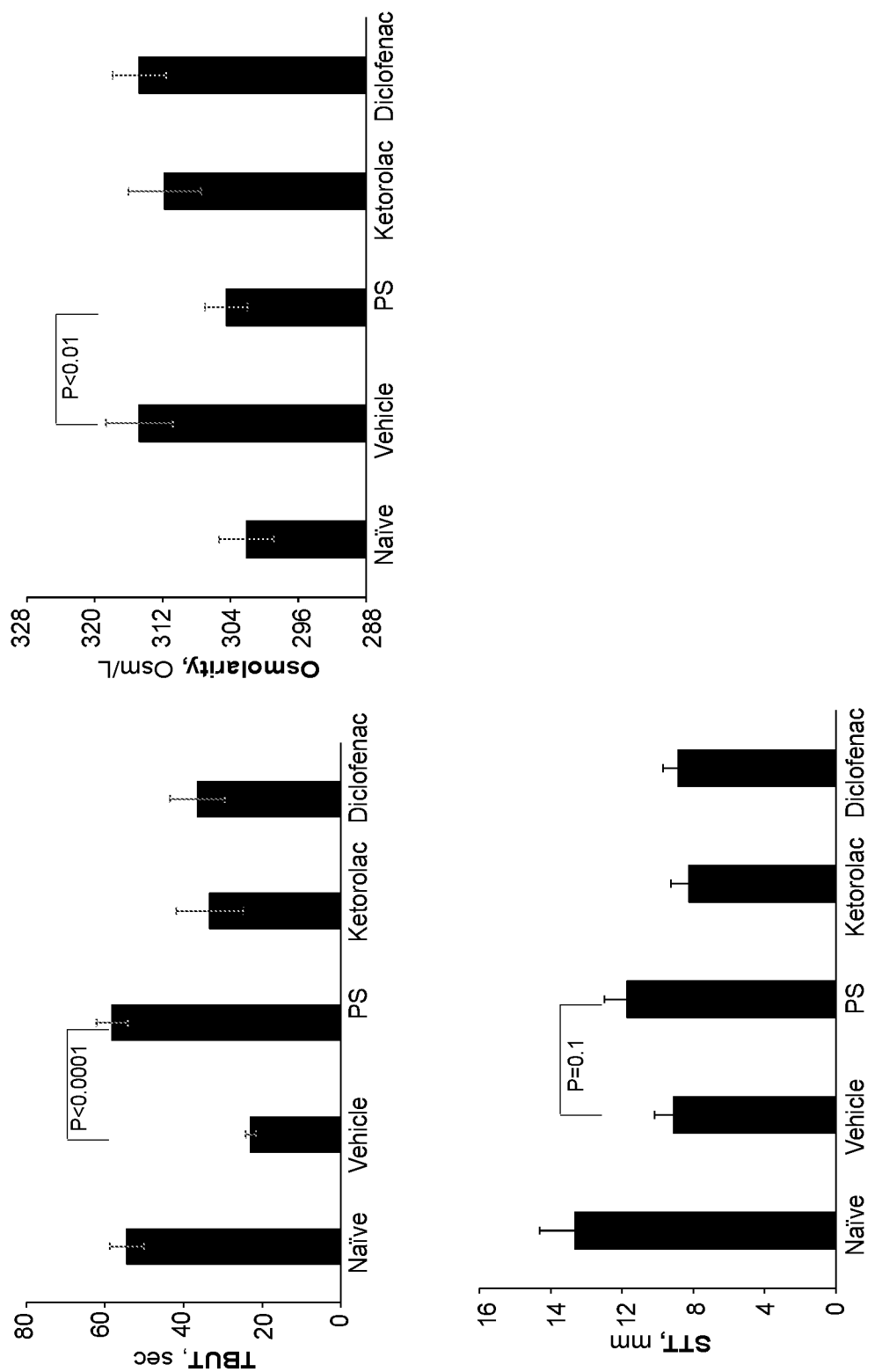
FIG. 4 illustrates that PS suppresses dry eye disease in rabbits. DED was induced by three sets of Con A injections as in Methods in two groups of rabbits that were treated with either vehicle or PS for three weeks and compared to a control naïve group (n=8-10 eyes/group). PS normalized TBUT, osmolarity and tear lactoferrin levels in contrast to vehicle. STT was improved by PS but the difference from vehicle did not reach statistical significance. Values=mean=SEM.

PS Suppresses Con A—Induced Dry Eye in Rabbits. The effect of PS on dry eye was determined in New Zealand White (NZW) rabbits, 2-3 kg (Charles River Labs, Waltham, Mass.). These rabbits were housed singly in rooms with strict temperature (70±5° F.) and humidity (45±5%) control and acclimated for at least 2 weeks prior to induction of dry eye by injection of Con A as above. NZW rabbits with Con A-induced dry eye (three sets of injections) were treated with PS formulated as nanoparticles and administered topically as eye drops 3x/day for 21 days, starting on the day of Con A injection. As shown in FIG. 4, PS restored to normal TBUT, tear osmolarity and tear lactoferrin levels. The STT value also improved but the difference from the vehicle group was significant only for trend. Similar results were obtained on days 5 and 14 (data not shown).

PS is Superior in Efficacy to Cyclosporine and Lifitegrast in DED. Using this model, we compared the effect of PS to that of cyclosporine and lifitegrast. Rabbits were treated for 6 days with PS as above or cyclosporine 0.05% or lifitegrast 5% eye drops 3x/day. In addition to determining TUBT, osmolarity and STT, we measured the levels of IL-8 and IL-1β in the ILGs of the rabbits harvested at euthanasia. Both of these cytokines are significant mediators of inflammation in DED. As shown in the table below, PS had statistically significant effects on TBUT, tear osmolarity, IL-8 and IL-1β levels. Cyclosporine improved significantly STT but had no significant effect on the remaining parameters. Lifitegrast improved significantly tear osmolarity but none of the other parameters. Of note, lifitegrast suppressed STT below the levels of the vehicle group and this suppression was statistically significant, but in the opposite direction for a useful therapeutic effect.

TABLE

Comparison of PS to Cyclosporine and Lifitegrast in DED in Rabbits

| | Vehicle | PS | Cyclosporine | Lifitegrast |
|---|---|---|---|---|
| | | mean ± SEM | | |
| TBUT, sec | 12.2 ± 2.8 | 43.6 ± 4.0 | 17 ± 5.4 | 9.1 ± 3.0 |
| | | $p < 0.001$ | $p = 0.11$ | $p = 0.23$ |
| Osmolarity, Osm/L | 311 ± 2.0 | 294 ± 4.6 | 306 ± 4.1 | 290 ± 4.2 |
| | | $p < 0.002$ | $p = 0.22$ | $p < 0.003$ |
| STT, mm | 11.7 ± 1.8 | 12.3 ± 0.6 | 18.3 ± 1.4 | 6.9 ± 0.7 |
| | | | $p < 0.01$ | $p < 0.01$* |
| IL-8, pg/mg protein | 13.5 ± 5.0 | 4.9 ± 1.7 | 7.4 ± 2.6 | 9.0 ± 2.4 |
| | | $p < 0.05$ | $p = 0.12$ | $p = 0.19$ |
| IL-1β pg/mg protein | 21.2 ± 6.6 | 8.4 ± 1.2 | 13.5 ± 3.1 | 11.5 ± 1.9 |
| | | $p < 0.03$ | $p = 0.13$ | $p = 0.06$ |

*This change is in the opposite direction for a useful therapeutic effect.

Figure 5:
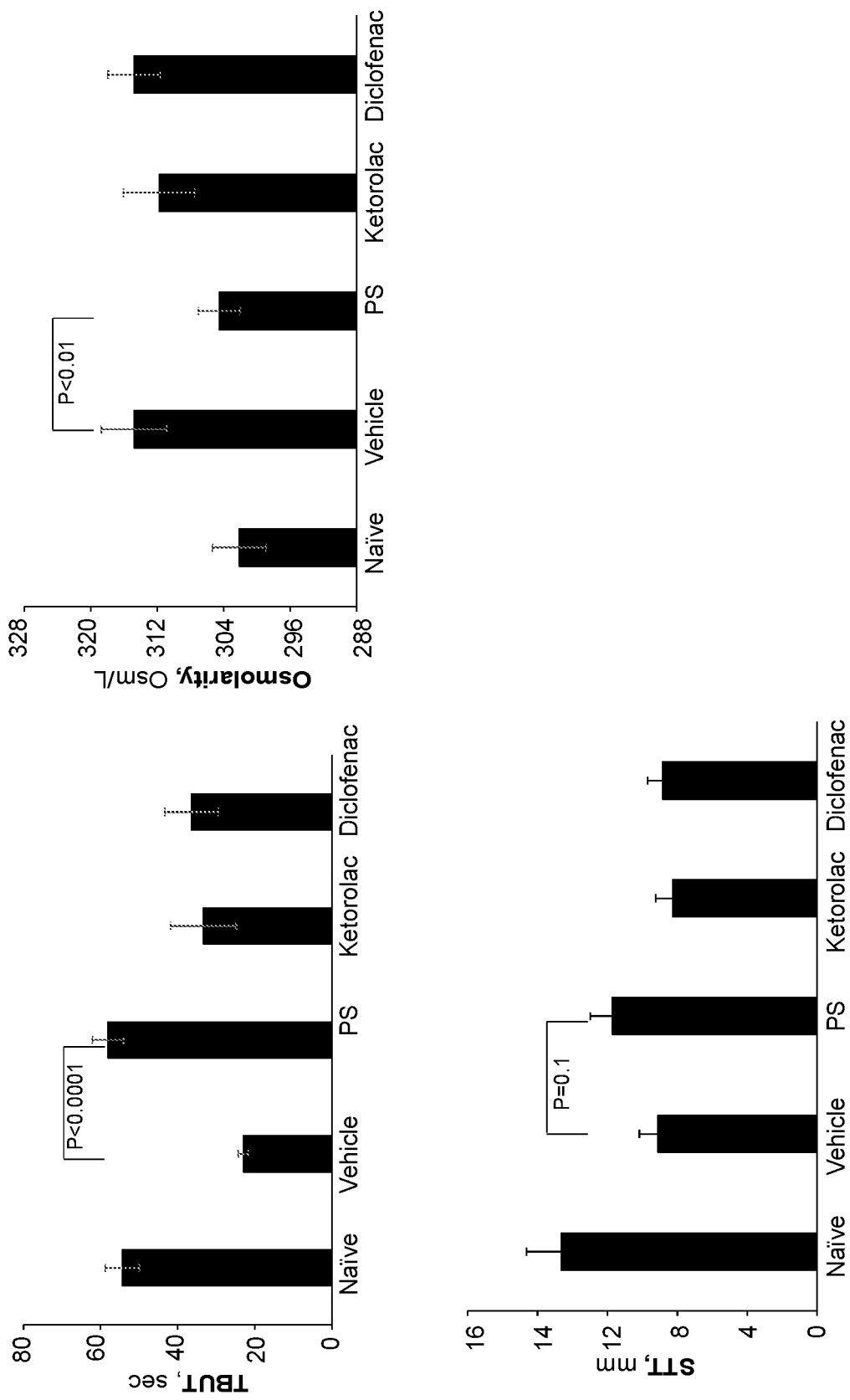
FIG. 5 illustrates a comparison of the effect on DED in rabbits of PS to two ophthalmic NSAIDs. Four groups of rabbits with DED induced by Con A were treated with vehicle or PS or ketorolac or diclofenac daily for one week as in Methods. A naïve group was used as a control. The values of TBUT, osmolarity and STT were comparable at baseline. The histograms depict the results for these three parameters on day 5. The results from the three test drugs were compared to those from the vehicle group; the three statistically significant differences are shown; all others were not significant. The vehicle group values were significantly different from the naïve group (not shown). Values=mean±SEM.

The efficacy of PS on DED was compared to that of ketorolac and diclofenac, two NSAIDs with strong ocular anti-inflammatory and analgesic properties (FIG. 5). After 1 week of treatment, PS as expected normalized TBUT and osmolarity while it had no significant effect on STT. Both ketorolac and diclofenac failed to improve any of these parameters.

The Safety of Topically Applied PS. The ocular application of PS was very well tolerated by the rabbits without evidence of discomfort. Slit lamp examination performed weekly during a 1-month application of PS showed no evidence of follicular/papillary response or injection of the conjunctiva nor were there signs of corneal abnormalities (staining defects, corneal vascularization, opacification, epithelial defects, stromal thinning or evidence of melts). Intraocular pressure measured with Tonopen (Reichert Technologies, Depew, N.Y.) remained normal throughout. No animal developed signs of uveitis, and at necropsy the posterior segment appeared normal in all animals.

The Mechanism of Action of PS in Dry Eye. Tissue culture, animal and human studies have established inflammation as the core mechanism of DED[8]. To determine the mechanism of action of PS in DED the response to PS of several factors known to play an important role in the inflammation associated with DED was explored. They include NF-κB; the cytokines TGF-β, IL-1 β, IL-6 and IL-8; the collagenases MMP-1 and MMP-9; and $PGE_2$. In these studies we used human conjunctival epithelial cells, the Wong-Kilbourne derivative of Chang conjunctival cells (clone 1 to 5c-41 American Type Culture Collection (Manassas, Va.) certified cell line, 20.2).

PS Suppresses NF-κB Activation. NF-κB is a transcription factor that modulates a large array of inflammatory mediators and cell signaling cascades, likely playing an important role in the pathogenesis of the ocular inflammation of DED. The effect of PS on NF-κB was evaluated in both cultured human conjunctival cells and in the ILG of rabbits with DED treated with PS or vehicle.

Figures 6A, 6B:
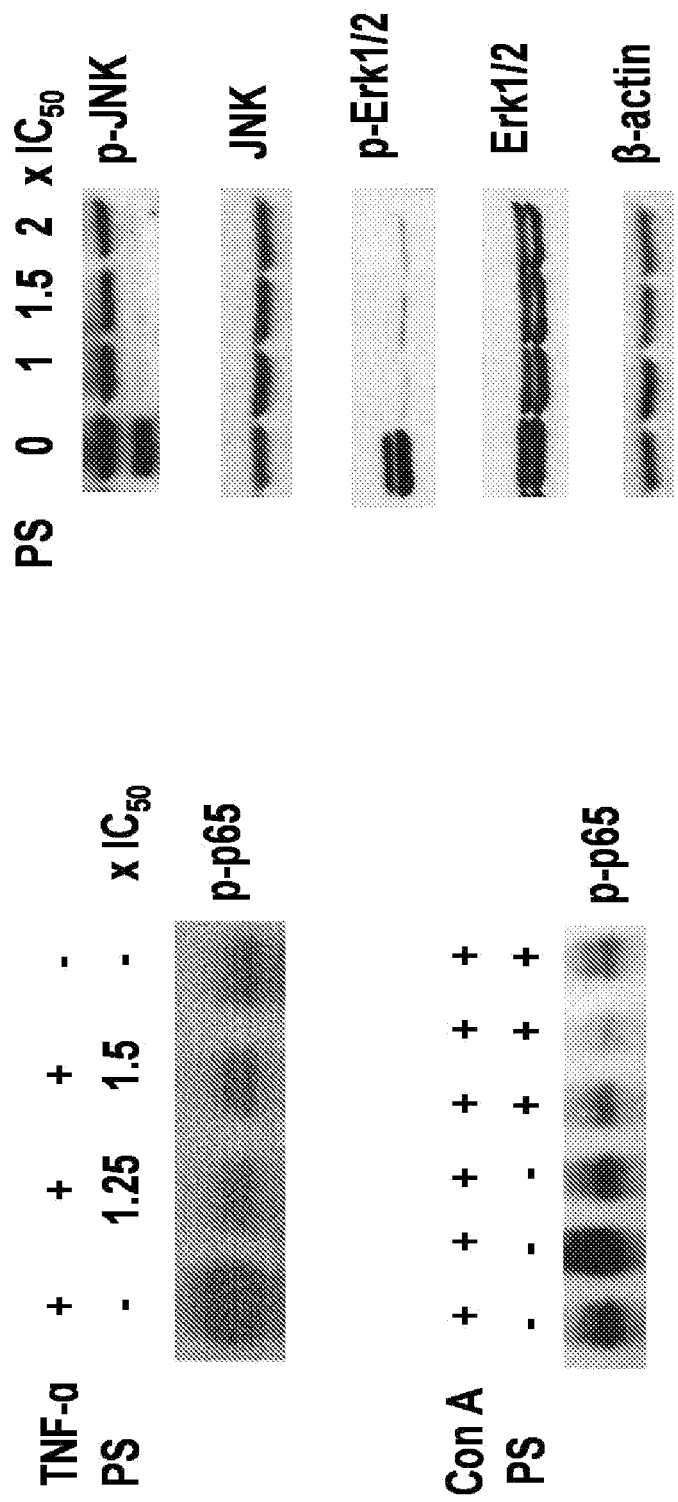
FIGS. 6A and 6B illustrate that PS suppresses the activation of NF-κB and MAPKs.

Human conjunctival cells were treated with various concentrations of PS. Five hours later, TNF-α was added to the culture medium to a final concentration of 10 ng/ml and the status of NF-κB activation was determined by EMSA 1 h later. As shown in FIG. 6A, PS significantly suppressed the activation of NF-κB. Similarly, after 1 week of treatment, PS suppressed NF-κB activation in the ILG of rabbits with DED compared to those treated with vehicle.

PS Suppresses MAPK Activation. MAPKs mediate the response of cells to tear hyperosmolarity and inflammatory cytokines in DED. These kinases can activate the transcription of stress-related genes, including MMP-9. MAPKs stimulate the production of cytokines including IL-β and TNF-α, thereby causing ocular surface damage.

Our conjunctiva cells express only the JNK and Erk1/2 pathways. PS profoundly suppressed the activation by phosphorylation of both (FIG. 6B).

PS Suppresses Matrix Metalloproteinases (MMPs). MMPs play a key role in the pathophysiology of DED. MMP-9 (mainly) and MMP-1 and have been implicated in DES. Tear MMP-9 activity parallels the severity of DED. MMPs, e.g., MMP-9, lyse components of the corneal epithelial basement membrane and tight junction proteins. Thus, it was determined that the effect of PS on MMP-1 in cultured conjunctival cells, and on MMP-9 in the ILG, cornea and aqueous humor of rabbits treated with PS.

Figure 7A:
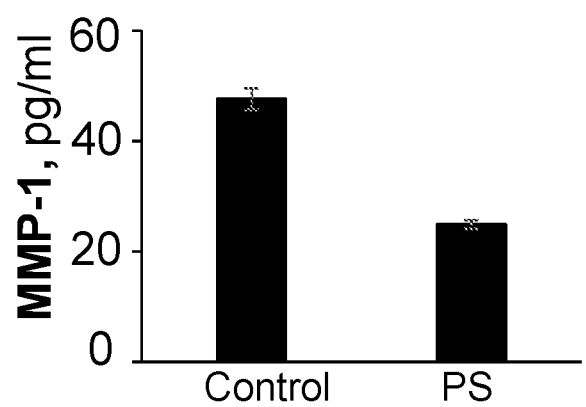
FIGS. 7A and 7B illustrate that PS suppresses cytokine levels in cultured conjunctival cells and the ILG of rabbits with DED.
Figure 7B:
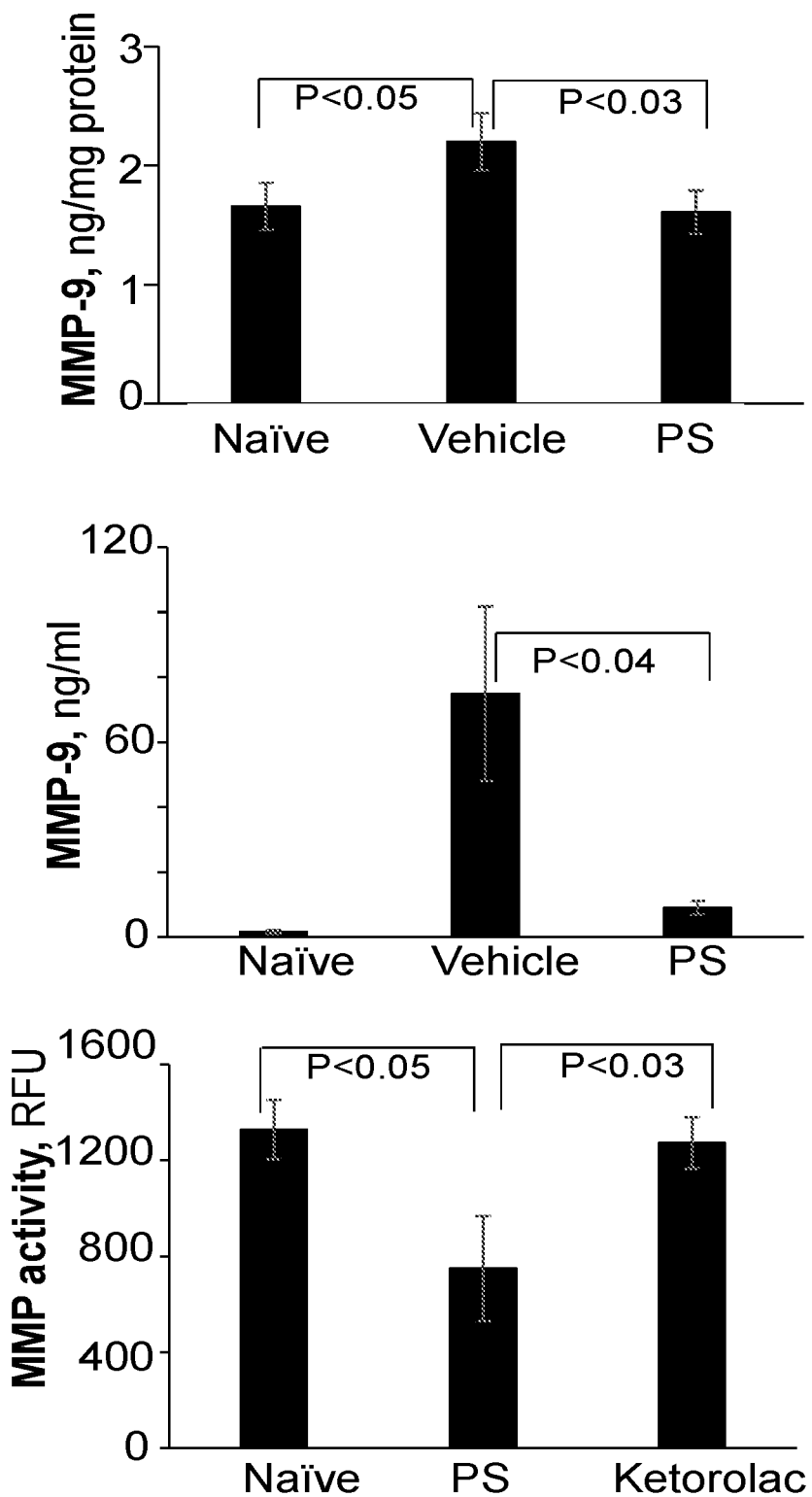

Treatment of cultured human conjunctival cells with PS $1 \times IC_{50}$ or $1.5 \times IC_{50}$ for 2 h, reduced the levels of MMP-1 secreted into the culture medium by 48% and 55%, respectively, compared to controls (47.7±2.0 vs. 24.9±0.8 and 21.6±0.8; mean±SEM; $p<0.01$ for both; FIG. 7A). These cells did not produce MMP-9. In rabbits treated with Con A the levels of MMP-9 in the ILG and the aqueous humor were significantly increased on day 7 compared to naïrabbits (no Con A treatment), as shown in FIG. 7B. Treatment of the rabbits having DED with PS for 1 week brought the MMP-9 levels back to normal.

In an acute experiment, naïve rabbits were treated with either PS or ketorolac (both administered topically) for 1 h and determined the activity of MMP in the cornea. This assay determines the activity of MMPs collectively in a given tissue. As shown in FIG. 7B, PS suppressed the activity of MMPs by 43% ($p<0.05$). In contrast, the NSAID ketorolac failed to affect MMP activity in the cornea.

PS Suppresses Cytokines. Cytokines play a significant role in DED, with the levels of some of them correlating with individual clinical parameters of DED in humans. It was determined that the response to PS of TGF-β, IL-6, IL-8 and IL-1β in the conjunctival cell line and the ILG of DED rabbits treated with PS.

Cells were treated with PS $1 \times IC_{50}$ and 2 h later TNF-α was added to the medium to a final concentration of 10 ng/ml. Culture media were harvested 24 h later and the levels of TGF-β, IL-6 and IL-8 were determined by ELISA. Of note, the levels of IL-1β were below the limit of detection.

Figure 8A:
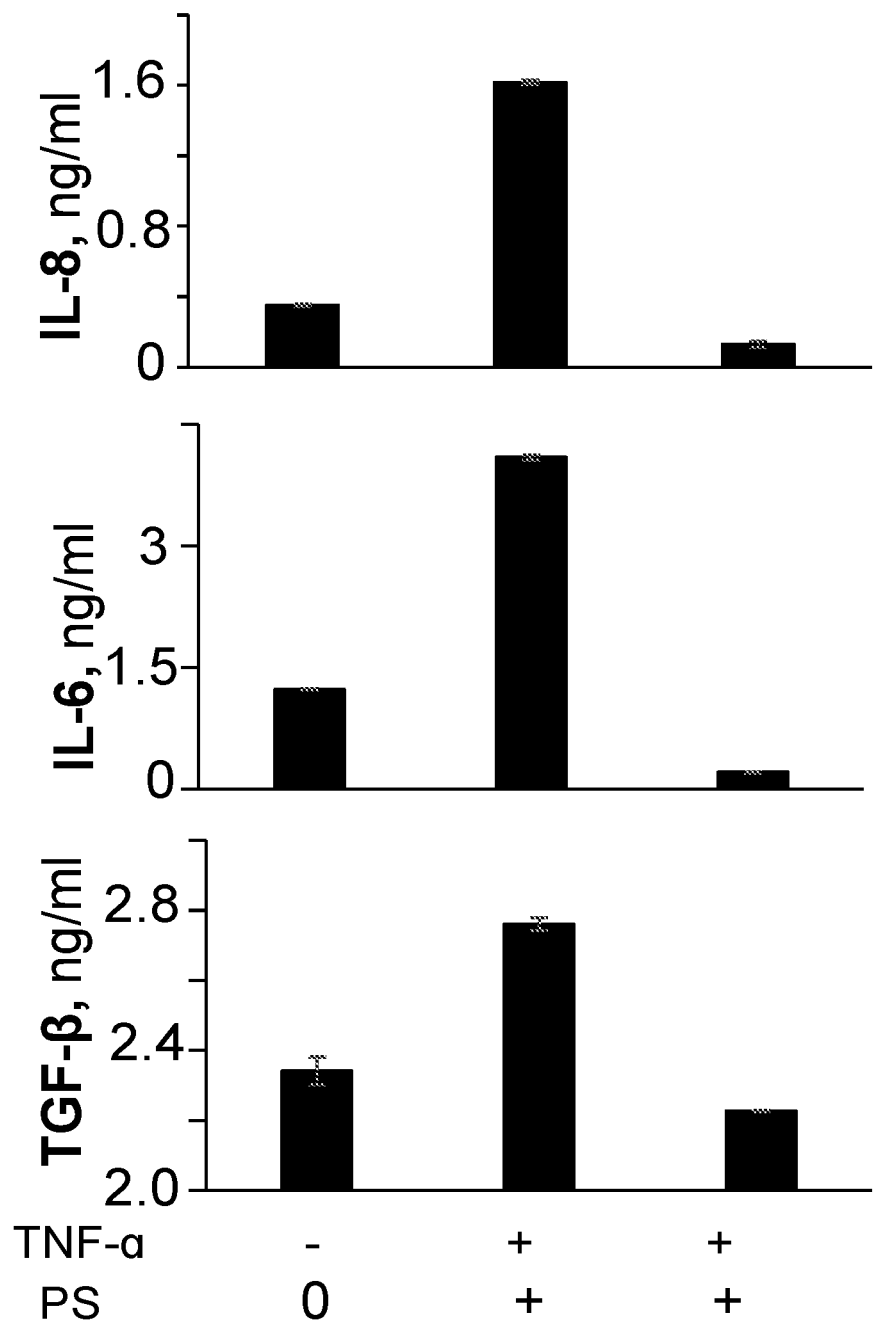
FIGS. 8A and 8B illustrate that PS suppresses the levels and activity of MMPs.
Figure 8B:
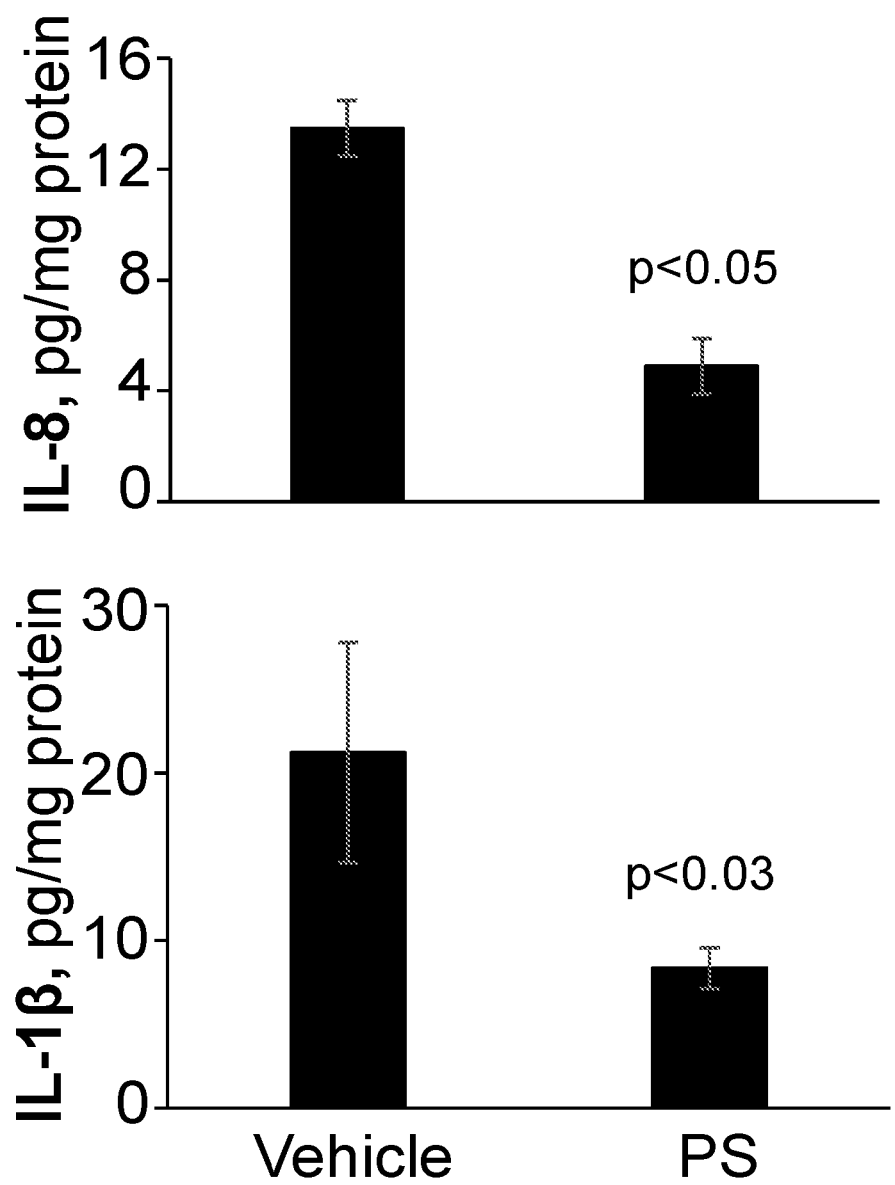

PS markedly suppressed the TNF-α-stimulated levels of IL-8 (92% reduction), IL-6 (95% reduction) and TGF-β, 19% reduction) (FIG. 8A). Moreover, for all three cytokines PS suppressed their unstimulated levels as well (62%, 84% and 4.7% reduction, respectively). In addition, PS suppressed the levels of IL-8 by 64% and IL-1β (not expressed by the cultured cells) by 61% in the ILG of rabbits treated with PS for 1 week compared to controls treated with vehicle (FIG. 8B). TGF-β was not detectable by the method in ILG homogenates. All these changes were statistically significant ($p<0.001$-$0.04$, except for the unstimulated TGF-β).

PS Preserves the Levels of $PGE_2$ in Cornea and Tears. Prostaglandins (PGs) are important inflammatory mediators acting at or near the site of their production. $PGE_2$ has been implicated in DED, with increased levels of $PGE_2$ in the tears of patients with DED. Increased COX-2 and PGE synthase expression levels were found in tear-producing tissues of DED mice (no tear levels were reported).

Figure 9A:
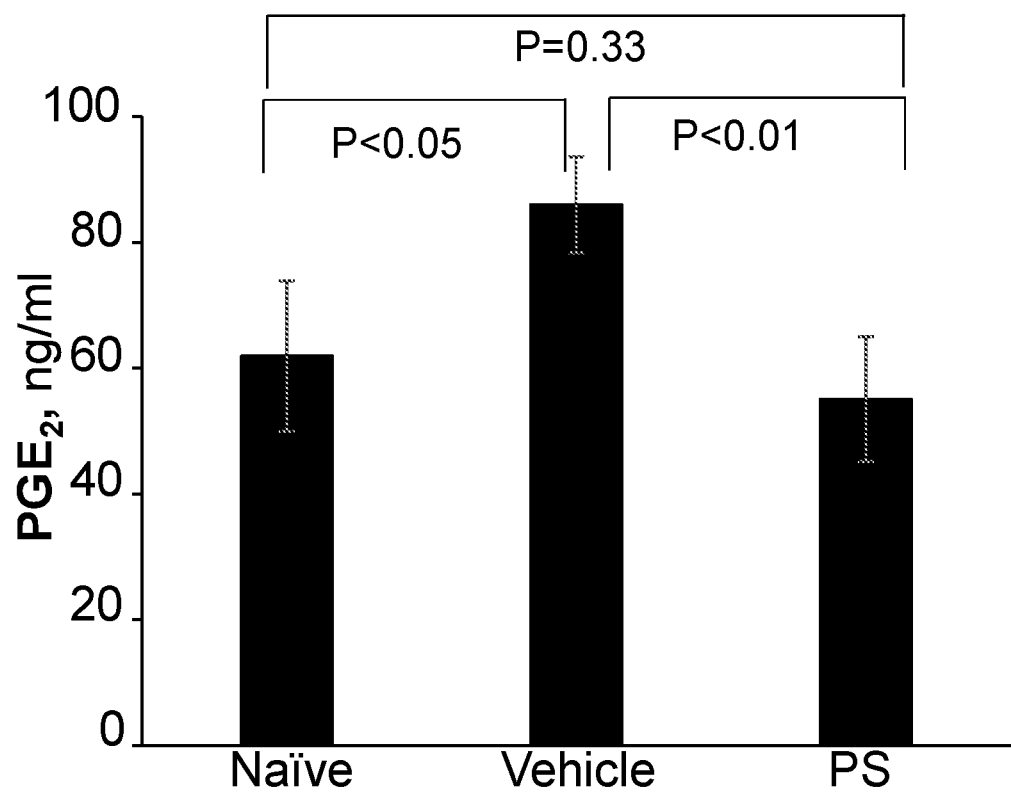
FIGS. 9A and 9B illustrate that PS preserves the levels of PGE$_2$ in tears and the cornea.
Figure 9B:
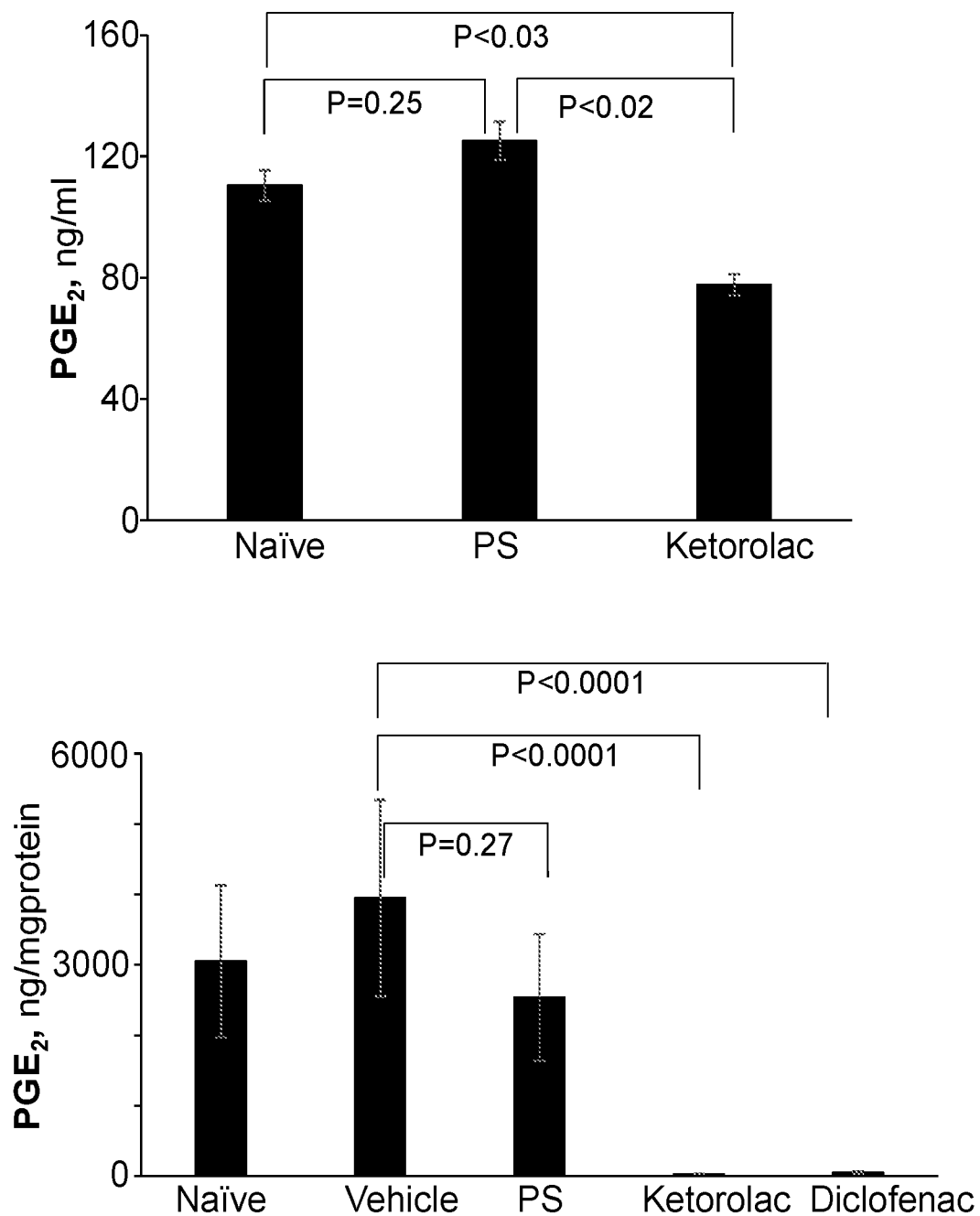

It was determined that the levels of $PGE_2$ in rabbit tears in three groups of rabbits, naïve and those with Con A-induced DED that were treated for 1 week either with PS or vehicle. As shown in FIGS. 9A and 9B, the tears of vehicle-treated rabbits had significantly higher levels of $PGE_2$ than naïve rabbits (no Con A, no drug treatment) whereas in PS-treated rabbits these levels were slightly lower than (but not significantly different from) those of naïve rabbits.

In an acute experiment, administered once topically to the eyes of four groups of rabbits with Con A-induced DED was one of the following: vehicle, PS, ketorolac or diclofenac; the latter two are NSAIDs used for the treatment of ocular inflammation and pain. It was determined that the levels of $PGE_2$ in the cornea of these rabbits obtained 1 h later as well as in the corneas of naïve rabbits. As shown in FIG. 9B, PS that $PGE_2$ levels in the PS-treated group were no different than those of vehicle-treated and naïve rabbits. This was in sharp contrast to ketorolac and diclofenac, which suppressed nearly completely the levels of $PGE_2$.

Discussion

This improved Con A-based model was successfully employed to determine the therapeutic efficacy and safety of a new drug, which demonstrates its applicability to drug development studies and strengthens its validity.

Taken together, our results demonstrate the robust therapeutic effect of PS. PS restored to normal (represented by the naive group) the values of 3 out of the 4 clinical parameters of DED. The only exception was STT, which improved in the PS group, but the change was statistically significant only for trend. Given the serious limitations of this test, however, the STT result does not detract from the conclusion that PS is efficacious.

This conclusion is strengthened by the comparison of the efficacy of PS to that of the two clinically used drugs for DED, cyclosporine and lifitegrast. From a panel of 5 parameters, including two cytokines important in the inflammatory response, IL-1 and IL-8 (the latter correlates with pain in humans), PS induced clinically meaningful responses in 4, as opposed to 1 for each of the other two.

A very important finding has been the absence of any evidence of corneal melt, a feared side effect of NSAID molecules. A defining property of NSAIDs is their ability to inhibit PG synthesis. PS is reported to either inhibit or not affect $PGE_2$ synthesis. In the cornea and tears, PS preserved the levels of $PGE_2$. In contrast, ketorolac and diclofenac, two ophthalmic NSAIDs known to induce corneal melt, markedly suppressed $PGE_2$ levels. It is conceivable that the safety differences between PS and these two NSAIDs could in part be attributed to their different effects on $PGE_2$. In fact, the cornea of DED is particularly sensitive to NSAIDs, so that they are either contraindicated or should be avoided. A contributor to the development of corneal melt is the activation of MMPs that degrade the collagen stroma of the cornea REF. PS suppressed the levels of MMP9 and the overall activity of MMPs in the cornea. This is in contrast to the lack of such an effect by ketorolac. Without being limited to any one theory of the invention, it appears that the combined effect of PS on $PGE_2$ and MMP could account for part of the ocular safety of PS. These findings point out a crucial difference between PS and conventional NSAIDs and allow the prediction that corneal melt, not seen during the period of observation, will be an exceedingly unlikely outcome even after long-term administration of PS.

The efficacy of PS in DED appears to result from a constellation of effects on signaling pathways and effector molecules that participate in the pathogenesis of DED. Interestingly, PS displayed significant mechanistic effects on both the surface of the eye and the lacrimal gland, where it reached significant levels. This multi-pathway effect of PS likely explains its strong effect on DED. Inflammation results from the activation of multiple pathways. Thus, suppressing a single pathway even completely may not affect the manifestation of inflammation since the redundancy of the system compensates for the inactivation of one pathway. PS, acting in a multi-targeted manner, avoids such mechanistic resistance, hence its impressive efficacy.

Example 9

The Ocular and Analgesic Effect of PS

The analgesic effect of PS was further examined on the surface of the eye by determining the corneal touch threshold (CTT) using the Luneau Cochet-Bonnet Aesthesiometer (Western Ophthalmics, Lynwood, Wash.) an adjustable nylon monofilament with a defined diameter, which is applied in different lengths to the center of the cornea.

Figure 10:
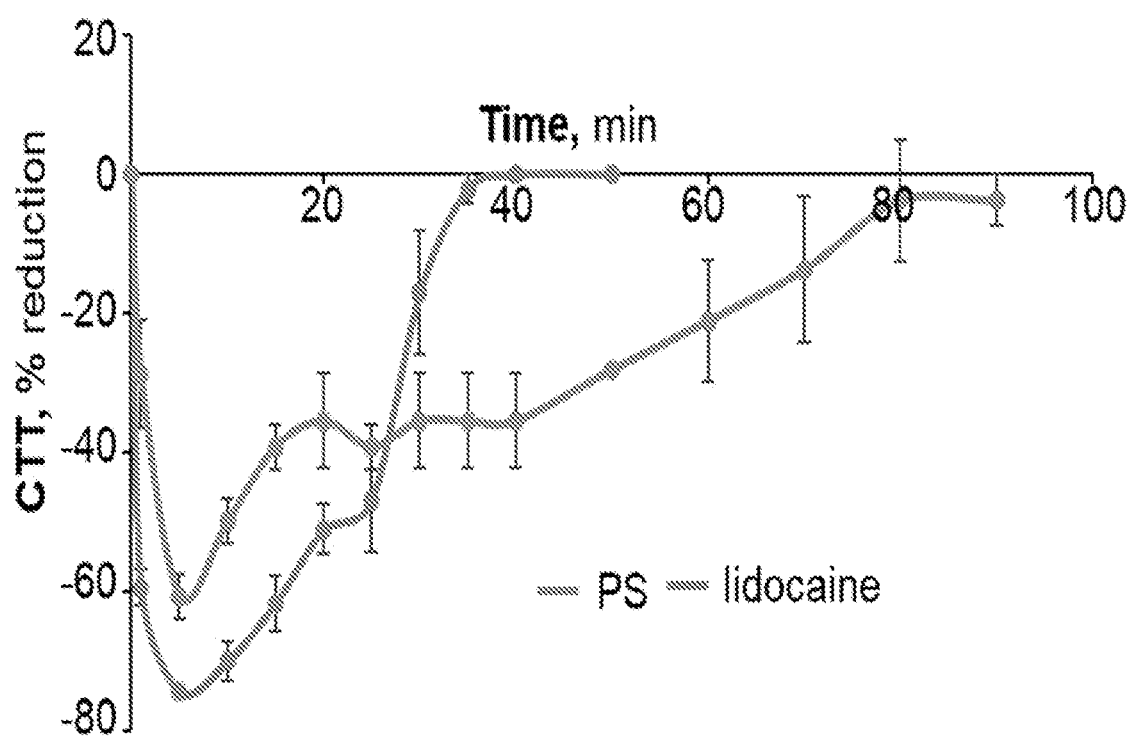
FIG. 10 illustrates the ocular analgesic effect of PS. One drop of PS, or vehicle or lidocaine was applied to one eye of rabbits (n=4/group) and the corneal touch threshold (CTT) was determined using an Eshesiometer. Vehicle had no effect on CTT (not shown; overlaps with the 0 value horizontal line). Values=mean±SEM.

As shown in FIG. 10, PS applied topically to naïrabbits as a single eye drop produced essentially instantaneous and significant analgesia. Vehicle, used as control, had no effect at all. Lidocaine 1% was the positive control.

Example 10

PS Inhibits the Production of VEGF and Neovascularization

Diabetic retinopathy is a disease driven mainly by the formation of new vessels. Inhibiting this process by targeting VEGF, the factor controlling new vessel formation is an established therapeutic strategy. Three sets of experiments demonstrated the ability of PS to inhibit VEGF and new vessel formation.

First, the effect of PS on VEGF production was evaluated by cultured human cancer ovarian cells, known to secrete VEGF to recruit vascular endothelial cells for angiogenesis. Therefore, VEGF is one of the most significant and direct targets in an anti-angiogenesis strategy. The experiments discovered that VEGF levels are reduced in ovarian cancer cells by PS. Secreted VEGF was assayed in the culture medium by ELISA. The results indicated that treatment with PS ($1.0 \times IC_{50}$, 24 h) reduced VEGF-A expression levels in both ovarian cancer parental (SKOV3, OVCAR3 and A2780) and resistant variants (A2780cis and A2780ADR). The degree of inhibition ranged between 65% and 100% compared to control as shown in the table below.

| Cell line | VEGF-A, % inhibition |
| --- | --- |
| SKOV-3 | 96 |
| OVCAR-3 | 100 |
| A2780 | 64 |
| A2780cis | 65 |
| A2780ADR | 77 |

Second, the effect of PS on new vessel formation (neovascularization) was evaluated using the chorioallantoic membrane (CAM) assay. In this assay, fertilized white chicken eggs (SPF Premium, Charles River Laboratory, North Franklin, Conn.) were incubated at 37° C. in 70% humidity for 3 days. The embryos were then incubated ex vivo in a sterile Petri dish for 7 days. Gelatin sponges adsorbed with or without VEGF plus PS or water (vehicle control) were implanted on the CAM surface and the neovasculature was counted on day 4 post implantation under a dissecting microscope.

Figure 11:
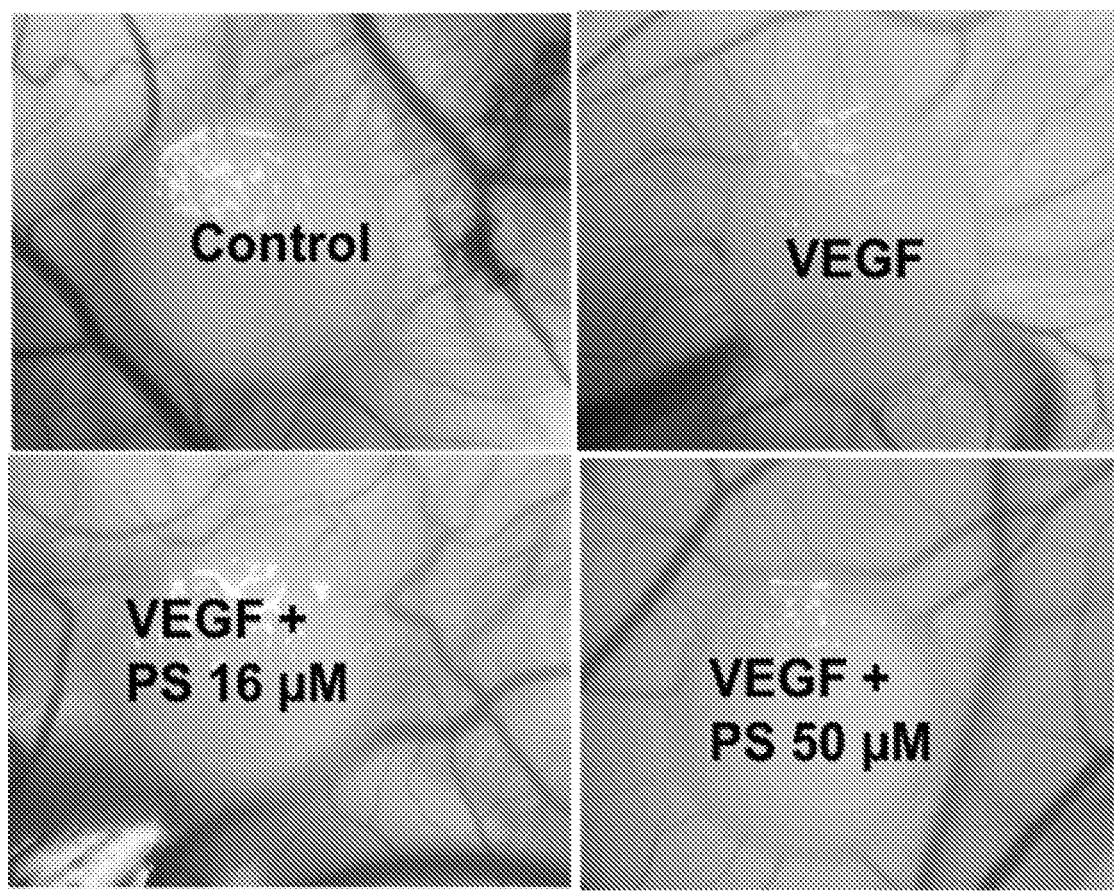
FIG. 11 illustrates images of chorioallantoic membrane (CAM) under various conditions where PS markedly decreased new vessel formation in CAM.

FIG. 11 shows representative images demonstrating the antiangiogenic effect of PS. The table below summarizes the associated findings. Within 4 days, PS inhibited neovascularization in CAMs by between 26% and 34% compared to control. The effect was present even when VEGF was not added to the system, as is standard practice

| | # of new vessels Mean ± SEM | % inhibition |
| --- | --- | --- |
| Control | 58 ± 4.9 | |
| VEGF | 62.3 ± 1.8 | |
| VEGF + PS 16 µM | 46.4 ± 1.5 | 26 ($P < 0.0001$) |
| VEGF + PS 50 µM | 41.4 ± 1.0 | 34 ($P < 0.0001$) |
| PS 50 µM | 41 ± 3.2 | 29 ($P < 0.016$) |

Figure 12:
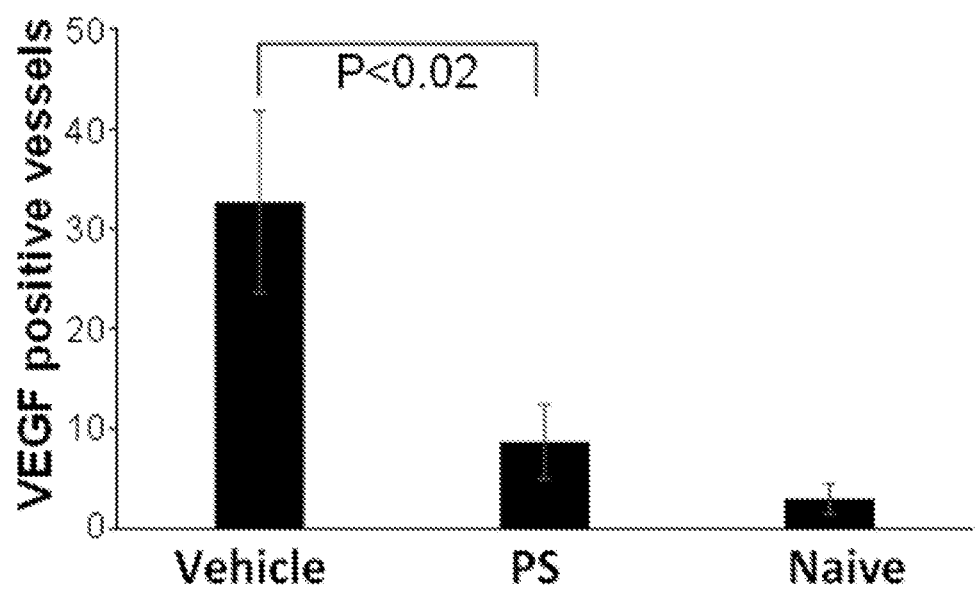
FIG. 12 illustrates the inhibition of angiogenesis in the lacrimal gland of rabbits with DED.

Finally, it was demonstrated that PS applied topically to the eye of New Zealand white rabbits inhibited angiogenesis in their lacrimal gland (FIG. 12). Rabbits with ConA-induced dry eye disease (n=8 eyes/group) were treated with PS 3.5% eye drops three times per day or vehicle for 1 week. Rabbit inferior lacrimal glands were removed and fixed in formalin. Immunohistochemistry for VEGF was performed on tissue sections and VEGF positive vessels were counted. PS reduced the number of VEGF positive cells by 73% bringing it to nearly normal values (the level in naïve rabbits)

Example 11

Exemplary PS Formulations that Deliver PS to the Retina

Composition: 3.5% PS; 16% Vitamin E TPGS (d-α-tocopheryl polyethylene glycol 1000 succinate); 3.18% mannitol; 1.2% boric acid; 0.005% polyquaternium-1 (Polyquad). Alternatively, vitamin E TPGS may be replaced by other solubilizing agents. Polyquad is added as a preservative.

Preparation Method: Polyquad and Vitamin E TPGS were dissolved in purified water followed by addition of PS and stirring at 70° C. for 30 min. Then the solution was centrifuged to remove non-dissolved drug particles and the supernatant was collected, to which mannitol and boric acid were added. The final volume was adjusted with purified water after adjusting the pH to 6.7±0.2 with NaOH.

Results: The above PS formulation was administered topically as eye drops to the eyes of New Zealand white rabbits. The levels of PS in ocular tissues 1 h and 3 h later were determined by HPLC. The Table below summarizes the findings:

| | PS, µM | |
| --- | --- | --- |
| Tissue | 1 h | 3 h |
| Cornea | 6.9 | 0.8 |
| Conjunctiva | 9.3 | 0.5 |
| Aqueous humor | 2.3 | 0.1 |
| Iris | 0.7 | 0.9 |
| Lens | 1.8 | 0.1 |
| Vitreous body | 3.6 | 0.0 |
| Retina | 2.7 | 0.2 |
| Choroid | 3.2 | 0.2 |
| Sclera | 2.3 | 0.2 |
| Lacrimal gland | 0.1 | 0.5 |

Example 12

Exemplary PS Formulations that Deliver PS to the Anterior Segment of the Eye

An exemplary formulation that allows for delivery of PS to the anterior segment of the eye includes the following in-situ gel formulations.

Gellan Gum-Based In-Situ Gel Formulation

Composition: 2.4~3% PS; 0.5% Gellan gum; 5% Vitamin E TPGS; 10% (2-hydroxypropyl)-β-cyclodextrin.

Preparation Method: A Gellan gum solution was prepared by adding a certain amount of gellan gum to deionized water and heating the mixture to 90° C. with fast stirring (500 rpm). Once completely dissolved, the solution was filtered through a 0.22 µm filter. Then, PS and additional excipients were added to the system to achieve the above concentrations and stirred at 50° C. at 500 rpm for 30 minutes to allow complete dissolution.

Results: The above PS formulation was administered topically as eye drops to the eyes of New Zealand white rabbits. The levels of PS in ocular tissues at 2 h later were determined by HPLC. The table below summarizes the findings.

| Tissue | PS, µM at 2 h |
|---|---|
| Cornea | 72.0 |
| Conjunctiva | 24.1 |
| Aqueous humor | 1.2 |
| Lens | 0.0 |
| Sclera | 0.0 |
| Iris | 0.0 |
| Choroid | 0.0 |
| Ciliary body | 0.0 |
| Vitreous | 0.0 |
| Retina | 0.0 |
| Lacrimal Gland | 0.0 |

Alternative Gellan Gum-Based In-Situ Gel Formulation
Composition: 2.4-3% PS; 0.4% Gellan gum; 10% Vitamin E TPGS; 5% (2-hydroxypropyl)-β-cyclodextrin.
Preparation: As above.
Results: PS in this formulation was administered topically to the eyes of New Zealand white rabbits and its biodistribution was determined as above. The Table below summarizes the findings.

| | PS, µM | | |
|---|---|---|---|
| Time, h | Cornea | Conjunctiva | Aqueous humor |
| 0.5 | 24.3 | 37.7 | 0.6 |
| 1 | 50.8 | 20.8 | 0.4 |
| 3 | 1.5 | 0.7 | 0.0 |
| 5 | 1.1 | 1.1 | 0.0 |
| 8 | 1.6 | 0.7 | 0.0 |

Sodium Alginate-Based In-Situ Gel Formulation
Composition: 3% PS, 1.5% sodium alginate, 5% Vitamin E TPGS, 10% (2-hydroxypropyl)-β-cyclodextrin.
Preparation Method: A sodium alginate solution was prepared by adding a certain amount of sodium alginate to deionized water and heating the mixture to 90° C. with fast stirring (500 rpm). Once completely dissolved, the solution was filtered through a 0.22 µm filter. Then, PS and additional excipients were added to the system to achieve the above concentrations and stirred at 50° C. at 500 rpm for 30 minutes to allow complete dissolution.

Alternative Sodium Alginate-Based In-Situ Gel Formulation
Composition: 3% PS, 1.5% sodium alginate, 15% Tween 80, 10% (2-hydroxypropyl)-β-cyclodextrin, 10% polyethylene glycol 400 (PEG400), 5% polyoxyl stearate.
Preparation Method: A sodium alginate solution was prepared by adding an appropriate amount of sodium alginate to deionized water and heating the mixture to 90° C. with fast stirring (500 rpm). Once sodium alginate was completely dissolved, the solution was filtered through a 0.22 µm filter. Then, PS and additional excipients were added to achieve the above concentrations and stirred at 50° C. at 500 rpm until complete dissolution.
Results: PS in this formulation was administered topically to the eyes of New Zealand white rabbits and its biodistribution was determined as above. The Table below summarizes the findings.

| | PS, µM | | | |
|---|---|---|---|---|
| Tissue | 1 h | 3 h | 5 h | 8 h |
| Cornea | 17.8 | 5.0 | 1.0 | 0.0 |
| Conjunctiva | 4.9 | 2.1 | 2.3 | 1.3 |
| Aqueous humor | 0.4 | 0.3 | 0.0 | 0.0 |
| Retina | 0.0 | 0.0 | 0.0 | 0.0 |

Poloxamer 407-Based In-Situ Gel Formulation:
Composition: 5.4% PS; 20% Poloxamer 407; 12% Vitamin E TPGS.
Preparation Method: Poloxamer 407 solution (thermosensitive gel solution) was prepared using a "cold method." The required amount of Poloxamer 407 and other excipients were dissolved in cold double-distilled water at 4° C. The mixture was stirred continuously until a clear solution was obtained. Then the appropriate amount of PS was dissolved in cold PM solution with continuous stirring at room temperature until a clear solution formed.
Results: PS in this formulation was administered topically as eye drops to the eyes of New Zealand white rabbits. The biodistribution of PS in ocular tissues at 3 h and 6 h was determined by HPLC. The Table below summarizes the findings.

| | PS, µM | |
|---|---|---|
| Tissue | 3 h | 6 h |
| Cornea | 45.1 | 13.6 |
| Conjunctiva | 5.6 | 10.7 |
| Aqueous humor | 0.3 | 0.3 |
| Iris | 0.0 | 0.0 |
| Lens | 0.0 | 0.0 |
| Vitreous | 0.0 | 0.0 |
| Retina | 0.0 | 0.0. |
| Choroid | 0.9 | 0.0 |
| Ciliary body | 0.0 | 0.0 |
| Sclera | 0.0 | 0.0 |

An Exemplary Formulation that Allows for Delivery of PS to the Anterior Segment of the Eye Includes the Following Nanoparticle Formulation
Composition: ~3.0-3.5% PS, 96.5~97% methoxy poly (ethylene glycol)-poly(lactide) (mPEG-PLA).
Preparation Method: Oil phase: 150 mg of PS and 1 g of PEG-PLA (Akina, Inc) were dissolved in 20 mL dichloromethane (DCM). Water phase: 365 mg of sodium cholate were dissolved in 60 ml of purified water. 5 mL of the oil phase was gently added into 15 mL of the water phase in a 50 mL Eppendorf conical tube. To create an emulsion, we used robe sonication for 2 min at 75% output (Branson 150, Fisher Scientific™, USA); the watt output was 12-13. The emulsion was transferred into a 100 mL beaker and stirred overnight at 600 rpm in a chemical hood until the DCM was fully evaporated. This was followed by centrifugation at 14,000 rpm for 1 h (Dupont, RC-5C). Then, the supernatant was transferred to another tube into which 3 mL of PBS were added to resuspend the nanoparticles. The nanoparticle solution was centrifuged for 6-7 seconds to remove aggregates. This supernatant was the final preparation.
Results:
Characterization of PS nanoparticles: Effective diameter=109.4 nm; particle size distribution: polydispersity index=0.163; Drug Encapsulation Efficiency (EE)=46.4% (it was calculated as % EE=drug encapsulated/drug added*100).

Biodistribution of PS after topical administration: PS formulated in nanoparticles as above was administered topically as eye drops to New Zealand white rabbits. The biodistribution of PS in ocular tissues at the indicated time points post administration was determined by HPLC. The Table below summarizes the findings.

|  | PS, μM | | |
|---|---|---|---|
| Tissue | 0.5 h | 1 h | 2 h |
| Cornea | 89.8 | 63.9 | 43.5 |
| Conjunctiva | 121.2 | 80.4 | 16.9 |
| Sclera | 32.1 | 17.1 | 4.7 |
| Iris | 2.8 | 6.4 | 1.3 |
| Lacrimal gland | 7.5 | 3.5 | 0.6 |

Biodistribution of PS after intravitreal injection: PS formulated in nanoparticles as above was injected directly into the vitreous of New Zealand white rabbits. The biodistribution of PS in ocular tissues at the indicated time points post administration was determined by HPLC. The Table below summarizes the findings.

|  | PS, μM | | | |
|---|---|---|---|---|
|  | 2% PS Nanoparticle Soln. | | 0.2% PS Nanoparticle Soln. | |
| Tissue | 0.5 h | 1 h | 0.5 h | 1 h |
| Cornea | 187.4 | 147.4 | 23.5 | 22.4 |
| Sclera | 223.7 | 180.2 | 39.8 | N.A. |
| Retina | 376.3 | 219.7 | 187.3 | 109.4 |
| Vitreous body | 125.4 | 34.0 | 198.5 | 56.2 |
| Aqueous humor | 0.0 | 1.3 | 0.0 | 0.1 |

Biodistribution of PS in human eyes (ex vivo): The anterior surface of the human eye (corresponding to an area slightly larger than the palpebral fissure) was brought into direct contact with a PS nanoparticle solution (PS concentrations were 0.2%, 1% and 2%) and treated as above for the solution formulations of PS. The Table below summarizes the results.

|  | PS, μM | | |
|---|---|---|---|
| Tissue | 0.2% PS-NPs | 1% PS-NPs | 2% PS-NPs |
| Cornea | 22.8 | 58.8 | 92.7 |
| Iris | 8.0 | 35.5 | 17.4 |
| Lens | 0.4 | 1.6 | 0.6 |
| Retina | 2.2 | 4.8 | 1.2 |
| Sclera | 30.7 | 152.0 | 113.0 |

Biodistribution of PS in porcine eyes (ex vivo): Explanted pig eyes were exposed to PS nanoparticle solution (PS concentration was 2%) and treated as were the human eyes. The results, summarized in the Table below, demonstrate that the uptake of PS by the ocular tissues is rapid, most of it occurring in 1 min or less and that the transition time to the sclera is time dependent, reaching the observed maximum within 60 min.

|  | Exposure to PS and subsequent incubation, min/min | | | |
|---|---|---|---|---|
|  | 1/15 | 1/60 | 10/15 | 10/60 |
| Tissue | PS, μM | | | |
| Cornea | 51.5 | 99.8 | 97.1 | 170.6 |
| Lens | 9.5 | 4.8 | 1.9 | 2.1 |
| Sclera | 86.6 | 123.9 | 89.9 | 47.9 |

Example 13

PS Topically Applied has a Strong Ocular Anti-Inflammatory Effect

The anti-inflammatory effect of PS in New Zealand white rabbits was evaluated following cataract surgery and administration of the proinflammatory bacterial lipopolysaccharide (LPS). Briefly, the lens was removed by phacoemulsification and aspiration and replaced with the hydrophobic acrylic intraocular lens (AR40e, AMO). Upon completion of the operation, 1 μg of LPS dissolved in 10 μl PBS was injected into the vitreous to induce uveitis.

Rabbits were treated with PS 3.5% formulated in nanoparticles or vehicle (nanoparticles without PS) applied topically as eye drops three times per day. The first application was made within 1 h after completion of surgery. The rabbits were examined daily and the aqueous humor (AH) was sampled by needle aspiration on days 1, 3, and 5 following the injection of LPS. The number of infiltrating cells in the AH was determined following standard methods. On day 5, the rabbits were euthanized and the implanted lens was removed and fixed in 2.5% glutaraldehyde and the number of inflammatory cells attached to the lens was examined under a dissecting microscope.

Figure 13:
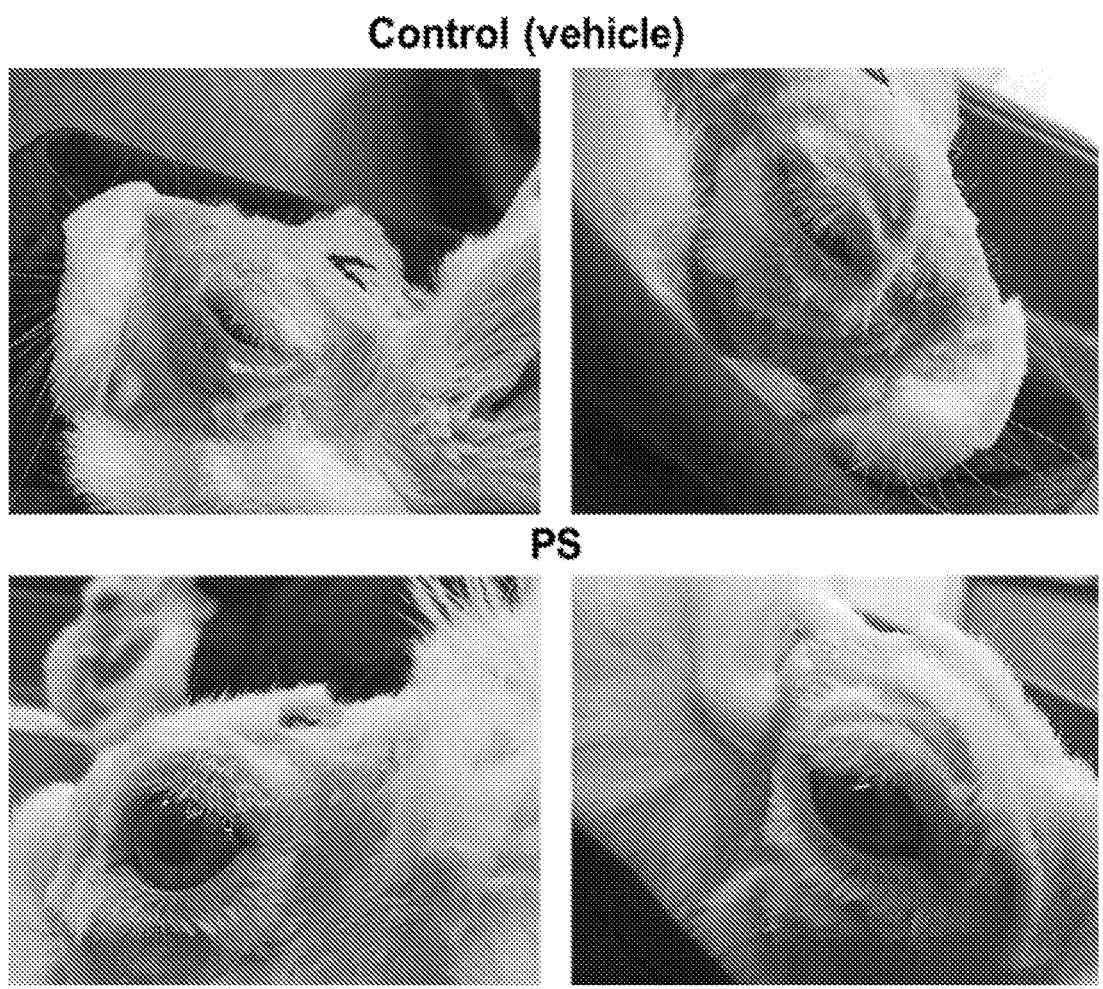
FIG. 13 illustrates that PS suppresses ocular inflammation in rabbits. Photographs were obtained 24 h after initiation of treatment. Upper panel: Rabbits treated with vehicle show a marked inflammatory reaction, making opening of their eyes difficult due to periorbital edema. Lower panel: PS-treated rabbits have minimal or no inflammatory reaction, permitting them to fully open their eyes.

The combination of cataract surgery and LPS injection created a marked inflammatory reaction in the eye and periorbital tissues such that the rabbits were unable to fully open their eyes due to periorbital edema (FIG. 13). Treatment with vehicle failed to improve the ocular inflammation, whereas PS essentially eliminated it during the first 24 h of treatment. The difference in the clinical appearance of the two groups of rabbits (vehicle vs. PS) is dramatic.

Figure 14:
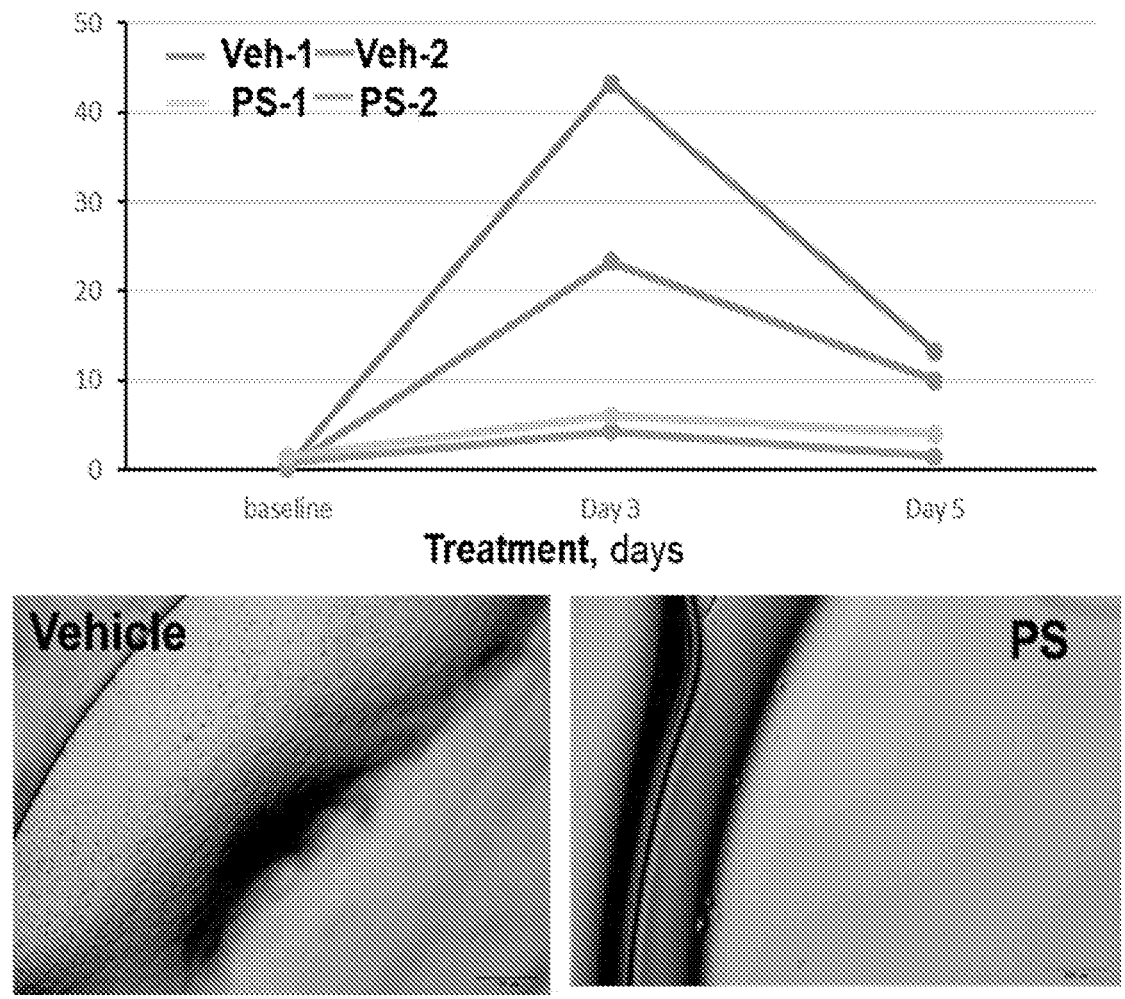
FIG. 14 illustrates that PS suppresses the number of inflammatory cells in rabbits. Upper panel: The marked inflammatory reaction induced in rabbits by cataract surgery plus LPS, led to a dramatic increase in the number of inflammatory cells in AH in vehicle-treated rabbits, which was prevented by PS. Data are from the four rabbits of FIG. 13. Individual values are the average of the two eyes of each rabbit. Lower panel: Representative photographs of two implanted lenses removed on day 5. The one from a vehicle-treated rabbit shows an abundance of cells attached to it. Very few cells can be seen in the lens from the PS-treated rabbit.

This clinical effect was paralleled by the effect of PS on the number of inflammatory cells in AH. As shown in FIG. 14, on day 3, vehicle-treated rabbits had increased numbers of cells ($24-35 \times 10^4$/ml) whereas those treated with PS had $<7 \times 10^4$/ml, an effect that paralleled the clinical manifestations of the inflammatory reaction. Similarly, we found that on day 5, when the implanted lenses were removed and examined; those from vehicle-treated rabbits had abundant inflammatory cells attached to them. In contrast, those from PS-treated rabbits had very few or no cells on them (FIG. 14, lower panel)

Example 14

Exemplary Cyclodextrin-Based Formulation of PS

Composition: 3-4% PS, 80% (2-hydroxypropyl)-β-cyclodextrin (HP-β-CD) with 0.1% Cremophor EL (F1) or 1% Tween 80 (F2).

Preparation Method: 6 g of HP-β-CD (CAS No 128446-35-5) was dissolved in 5 mL of purified water at 55° C. water bath. 380 mg of PS was added into above solution, and keep in 55° C. water bath overnight or till PS fully dissolved.

Kolliphor EL or Tween 80 was respectively added into the PS HP-β-CD solution. The obtained solution was centrifuged at 3000 rpm for 10 min to remove undissolved particles. The supernatant was collected.

Results:

Biodistribution of PS after topical administration: PS in the formulations was administered topically as eye drops to the eyes of New Zealand white rabbits. The levels of PS in ocular tissues at 0.5 h, 1 h and 3 h were determined by HPLC. The Table below summarizes the findings.

| | PS, μM | | | | | |
|---|---|---|---|---|---|---|
| | 0.5 h | | 1 h | | 3 h | |
| Tissue | F1 | F2 | F1 | F2 | F1 | F2 |
| Cornea | 46.8 | 27 | 42.4 | 61.5 | 14.1 | 9.8 |
| Conjunctiva | 20.9 | 10.1 | 22.6 | 18 | 19.8 | 11.9 |
| Iris | 2.8 | 1.7 | 2.3 | 4.7 | 0.6 | 8.8 |
| Sclera | 5.2 | 3.5 | 2.4 | 1.6 | 0.6 | 1 |
| Lacrimal gland | 0.3 | 0.3 | 0.9 | 2.5 | 0.1 | 2 |

Biodistribution of PS in human eyes (ex vivo): Human cadaveric eyes were obtained through the Lions Eye Bank for Long Island, Valley Stream, NY. They were preserved on ice and used within 2 h from removal from the donors.

The anterior surface of the human eye (corresponding to an area slightly larger than the palpebral fissure) was brought into direct contact with a PS HP-β-CD solution (PS concentration at 0.5%, 2.0% and 3.3%) and incubated for 10 min at 37° C. The eye was then rinsed with 10% dimethylsulfoxide (DMSO) to remove residual PS from the surface of the eye and incubated in PBS for 60 min. (Control experiments showed this DMSO concentration to completely remove PS without damaging the ocular tissues). At the specified times, ocular tissues were dissected and PS levels determined by HPLC. The Table below summarizes the findings.

| | PS, μM | | |
|---|---|---|---|
| Tissue | 3.3% PS | 2.0% PS | 0.5% PS |
| Cornea | 266.4 | 397.7 | 187.2 |
| Aqueous | 19.5 | ND | 2.4 |
| Iris | 169.3 | 34.2 | 25.6 |
| Lens | 1.9 | 1.4 | 0.6 |
| Vitreous | 4.3 | ND | 0.3 |
| Retina | 48.5 | 38.7 | 2.9 |
| Choroid | 261.4 | ND* | 28.5 |
| Sclera | 2,596.6 | 870.9 | 381.3 |

*ND: Not Determined

The anti-inflammatory effect of PS in New Zealand white rabbits was evaluated following cataract surgery and administration of the proinflammatory bacterial lipopolysaccharide (LPS). Briefly, the lens was removed by phacoemulsification and aspiration and replaced with the hydrophobic acrylic intraocular lens (AR40e, AMO). Upon completion of the operation, 1 μg of LPS dissolved in 10 μPBS was injected into the vitreous to induce uveitis.

Example 15

PS Combined with Antibiotics Does Not Inhibit Antimicrobial Efficacy

It was assessed whether the combination of PS with antibiotics for their topical application to the eye affects the antimicrobial activity of the antibiotics. To this end, the disk diffusion method was used.

Figure 15:
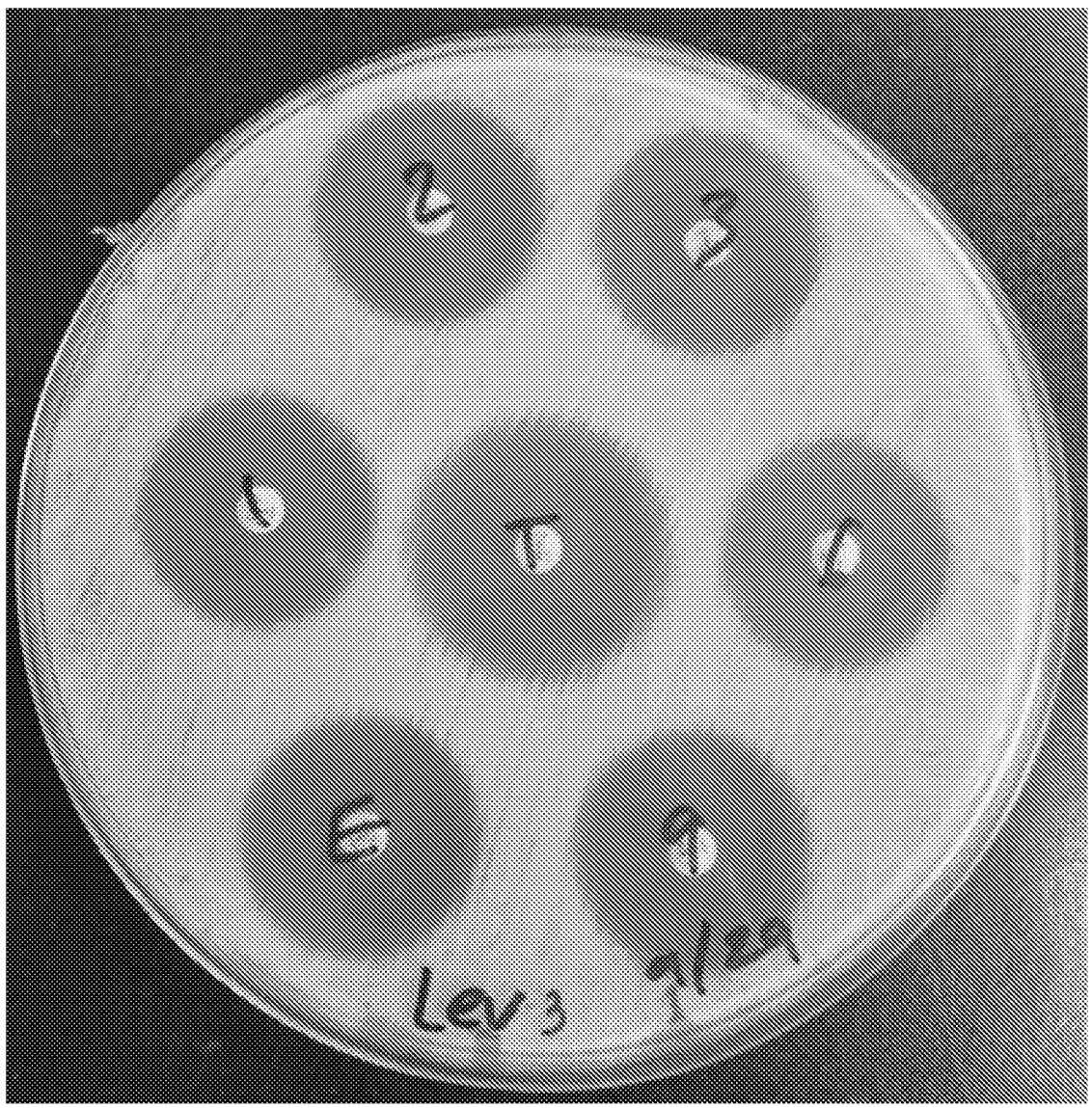
FIG. 15 illustrates an agar plate with susceptibility discs applied to a *S. aureus* growth. The growth inhibition zones are evident. Levofloxacin was the antibiotic tested.

Briefly, *Staphylococcus aureus* grown in culture was seeded evenly on Muller-Hinton II Agar plates (BD Diagnostic Systems) at the standard concentration of $2 \times 10^8$ colony-forming units per mL. Antibiotic antimicrobial susceptibility disks (Thermo Scientific Oxoid™) were impregnated with one of six concentrations of PS (0%, 1%, 2%, 3%, 6%, 9%); 10 μL of each was evenly dispensed on each disk. An additional control was disks with no PS and no vehicle. The various disks were lightly pressed onto the agar surface as shown in FIG. 15. The growth of bacteria around each disk was monitored and the area of "no growth" around each disk was measured 24 h later.

Results: As summarized in the Table below, PS did not appreciably change the inhibition zone of each antibiotic compared to control (0% PS, i.e., only vehicle). Disks with no PS and no vehicle gave virtually identical results to vehicle controls (not shown). Thus the antimicrobial activity of these two quinolone antibiotics was maintained in the presence of PS even at concentrations significantly exceeding those applied to the eye as eye drops (typically 3%). Similar results were obtained with additional antibiotics.

| | Ciprofloxacin | Levofloxacin |
|---|---|---|
| | Inhibition Zone, mm | |
| PS, % | mean ± SD | |
| 0% | 30.0 ± 0.0 | 32.3 ± 0.6 |
| 1% | 30.3 ± 0.6 | 32.7 ± 0.6 |
| 2% | 29.7 ± 0.6 | 32.0 ± 0.0 |
| 3% | 29.3 ± 0.6 | 31.7 ± 0.6 |
| 6% | 27.7 ± 0.4 | 32.3 ± 1.5 |
| 9% | 29.7 ± 0.6 | 31.0 ± 1.0 |

Example 16

PS Distributes to Various Tissues of the Eye

To assess the contribution of the foregoing formulations to the PK/biodistribution of PS in the ocular tissues, a solution of PS in pure propylene glycol (PG) was studied. PG is well tolerated by the eye. A 3.5% PS solution (in PG) as eye drops was administered topically to the eyes of New Zealand white rabbits and its 1-hour biodistribution was determined by HPLC. The Table summarizes the findings.

| Tissue | PS, μM, 1 h |
|---|---|
| Cornea | 38.8 |
| Conjunctiva | 3.3 |
| Aqueous humor | 0.7 |
| Vitreous body | 0.0 |
| Retina | 0.0 |
| Choroid | 0.0 |
| Sclera | 0.0 |
| Lacrimal gland | 0.1 |

These findings indicate, without being limited to any one theory of the invention, that each of the various formulations exemplified herein targets PS to ocular tissues in a specific manner.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

REFERENCES

1. The definition and classification of dry eye disease: report of the Definition and Classification Subcommittee of the International Dry Eye WorkShop (2007). Ocul Surf 2007; 5(2):75-92.
2. Phadatare S P, Momin M, Nighojkar P, Askarkar S, Singh K K. A Comprehensive Review on Dry Eye Disease: Diagnosis, Medical Management, Recent Developments, and Future Challenges. Advances in Pharmaceutics 2015; 2015:1-12.
3. Paulsen A J, Cruickshanks K J, Fischer M E, Huang G H, Klein B E, Klein R, et al. Dry eye in the beaver dam offspring study: prevalence, risk factors, and health-related quality of life. Am J Ophthalmol 2014; 157(4):799-806.
4. The epidemiology of dry eye disease: report of the Epidemiology Subcommittee of the International Dry Eye WorkShop (2007). Ocul Surf 2007; 5(2):93-107.
5. Lin H, Yiu S C. Dry eye disease: A review of diagnostic approaches and treatments. Saudi J Ophthalmol 2014; 28(3):173-81.
6. de Paiva C S, Pflugfelder S C. Rationale for anti-inflammatory therapy in dry eye syndrome. Arq Bras Oftalmol 2008; 71(6 Suppl):89-95.
7. Hessen M, Akpek E K. Dry eye: an inflammatory ocular disease. J Ophthalmic Vis Res 2014; 9(2):240-50.
8. Lan W, Petznick A, Heryati S, Rifada M, Tong L. Nuclear Factor-kappaB: central regulator in ocular surface inflammation and diseases. Ocul Surf 2012; 10(3):137-48.
9. Peng W J, Yan J W, Wan Y N, Wang B X, Tao J H, Yang G J, et al. Matrixmetalloproteinases: a review of their structure and role in systemic sclerosis. J Clin Immunol 2012; 32(6):1409-14.
10. Yoon K C, De Paiva C S, Qi H, Chen Z, Farley W J, Li D Q, et al. Expression of Th-1 chemokines and chemokine receptors on the ocular surface of C57BL/6 mice: effects of desiccating stress. Invest Ophthalmol Vis Sci 2007; 48(6):2561-9.
11. The management of dry eye. BMJ 2016; 354:i4463.
12. Moshirfar M, Pierson K, Hanamaikai K, Santiago-Caban L, Muthappan V, Passi S F. Artificial tears potpourri: a literature review. Clin Ophthalmol 2014; 8:1419-33.
13. Wan K H, Chen L J, Young A L. Efficacy and Safety of Topical 0.05% Cyclosporine Eye Drops in the Treatment of Dry Eye Syndrome: A Systematic Review and Meta-analysis. Ocul Surf 2015; 13(3):213-25.
14. Zhou X Q, Wei R L. Topical cyclosporine A in the treatment of dry eye: a systematic review and meta-analysis. Cornea 2014; 33(7):760-7.
15. Perez V L, Pflugfelder S C, Zhang S, Shoj aei A, Haque R. Lifitegrast, a Novel Integrin Antagonist for Treatment of Dry Eye Disease. Ocul Surf 2016; 14(2):207-15.
16. Semba C P, Gadek T R. Development of lifitegrast: a novel T-cell inhibitor for the treatment of dry eye disease. Clin Ophthalmol 2016; 10:1083-94.
17. Gaynes B I, Onyekwuluje A. Topical ophthalmic NSAIDs: a discussion with focus on nepafenac ophthalmic suspension. Clin Ophthalmol 2008; 2(2):355-68.
18. Mackenzie G G, Sun Y, Huang L, Xie G, Ouyang N, Gupta R C, et al. Phospho-sulindac (OXT-328), a novel sulindac derivative, is safe and effective in colon cancer prevention in mice. Gastroenterology 2010; 139(4):1320-32.
19. Cheng K W, Wong C C, Alston N, Mackenzie G G, Huang L, Ouyang N, et al. Aerosol administration of phospho-sulindac inhibits lung tumorigenesis. Mol Cancer Ther 2013; 12(8):1417-28.
20. Huang L, Mackenzie G, Ouyang N, Sun Y, Xie G, Johnson F, et al. The novel phospho-non-steroidal anti-inflammatory drugs, OXT-328, MDC-22 and MDC-917, inhibit adjuvant-induced arthritis in rats. Br J Pharmacol 2011; 162(7):1521-33.
21. Wong C C, Cheng K W, Papayannis I, Mattheolabakis G, Huang L, Xie G, et al. Phospho-NSAIDs have enhanced efficacy in mice lacking plasma carboxylesterase: implications for their clinical pharmacology. Pharmaceutical research 2015; 32(5):1663-75.
22. Wong C C, Cheng K W, Xie G, Zhou D, Zhu C H, Constantinides P P, et al. Carboxylesterases 1 and 2 hydrolyze phospho-nonsteroidal anti-inflammatory drugs: relevance to their pharmacological activity. J Pharmacol Exp Ther 2012; 340(2):422-32.
23. Schrader S, Mircheff A K, Geerling G. Animal models of dry eye. Dev Ophthalmol 2008; 41:298-312.
24. Xiong C, Chen D, Liu J, Liu B, Li N, Zhou Y, et al. A rabbit dry eye model induced by topical medication of a preservative benzalkonium chloride. Invest Ophthalmol Vis Sci 2008; 49(5):1850-6.
25. Barabino S. Animal models of dry eye. Arch Soc Esp Oftalmol 2005; 80(12):693-4; 95-6.
26. Barabino S, Chen W, Dana M R. Tear film and ocular surface tests in animal models of dry eye: uses and limitations. Exp Eye Res 2004; 79(5):613-21.
27. Barabino S, Dana M R. Animal models of dry eye: a critical assessment of opportunities and limitations. Invest Ophthalmol Vis Sci 2004; 45(6):1641-6.
28. Singh S, Moksha L, Sharma N, Titiyal J S, Biswas N R, Velpandian T. Development and evaluation of animal models for sex steroid deficient dry eye. J Pharmacol Toxicol Methods 2014; 70(1):29-34.
29. Burgalassi S, Panichi L, Chetoni P, Saettone M F, Boldrini E. Development of a simple dry eye model in the albino rabbit and evaluation of some tear substitutes. Ophthalmic research 1999; 31(3):229-35.
30. Nagelhout T J, Gamache D A, Roberts L, Brady M T, Yanni J M. Preservation of tear film integrity and inhibition of corneal injury by dexamethasone in a rabbit model of lacrimal gland inflammation-induced dry eye. J Ocul Pharmacol Ther 2005; 21(2):139-48.
31. Seo M J, Kim J M, Lee M J, Sohn Y S, Kang K K, Yoo M. The therapeutic effect of DA-6034 on ocular inflammation via suppression of MMP-9 and inflammatory cytokines and activation of the MAPK signaling pathway in an experimental dry eye model. Curr Eye Res 2010; 35(2):165-75.
32. Zheng W, Ma M, Du E, Zhang Z, Jiang K, Gu Q, et al. Therapeutic efficacy of fibroblast growth factor 10 in a rabbit model of dry eye. Mol Med Rep 2015; 12(5):7344-50.
33. Williams J L, Ji P, Ouyang N, Liu X, Rigas B. NO-donating aspirin inhibits the activation of NF-kappaB in human cancer cell lines and Min mice. Carcinogenesis 2008; 29(2):390-7.
34. Davis F A. The Anatomy and Histology of the Eye and Orbit of the Rabbit. Trans Am Ophthalmol Soc 1929; 27:400 2-41.
35. Senchyna M, Wax M B. Quantitative assessment of tear production: A review of methods and utility in dry eye drug discovery. J Ocul Biol Dis Infor 2008; 1(1):1-6.
36. Demetriades A M, Leyngold I M, D'Anna S, Eghrari A O, Emmert D G, Grant M P, et al. Intraglandular injection of botulinum toxin a reduces tear production in rabbits. Ophthal Plast Reconstr Surg 2013; 29(1):21-4.
37. Enriquez-de-Salamanca A, Castellanos E, Stern M E, Fernandez I, Carreno E, Garcia-Vazquez C, et al. Tear cytokine and chemokine analysis and clinical correlations in evaporative-type dry eye disease. Mol Vis 2010; 16:862-73.
38. Cargnello M, Roux P P. Activation and function of the MAPKs and their substrates, the MAPK-activated protein kinases. Microbiol Mol Biol Rev 2011; 75(1):50-83.
39. Pflugfelder S C, Wilhelmus K R, Osato M S, Matoba A Y, Font R L. The autoimmune nature of aqueous tear deficiency. Ophthalmology 1986; 93(12):1513-7.
40. Luo L, Li D Q, Doshi A, Farley W, Corrales R M, Pflugfelder S C. Experimental dry eye stimulates production of inflammatory cytokines and MMP-9 and activates MAPK signaling pathways on the ocular surface. Invest Ophthalmol Vis Sci 2004; 45(12):4293-301.
41. Leonardi A, Brun P, Abatangelo G, Plebani M, Secchi A G. Tear levels and activity of matrix metalloproteinase (MMP)-1 and MMP-9 in vernal keratoconjunctivitis. Invest Ophthalmol Vis Sci 2003; 44(7):3052-8.
42. Sobrin L, Liu Z, Monroy D C, Solomon A, Selzer M G, Lokeshwar B L, et al. Regulation of MMP-9 activity in human tear fluid and corneal epithelial culture supernatant. Invest Ophthalmol Vis Sci 2000; 41(7):1703-9.
43. Pflugfelder S C, Farley W, Luo L, Chen L Z, de Paiva C S, Olmos L C, et al. Matrix metalloproteinase-9 knockout confers resistance to corneal epithelial barrier disruption in experimental dry eye. Am J Pathol 2005; 166(1):61-71.
44. Kim H S, Luo L, Pflugfelder S C, Li D Q. Doxycycline inhibits TGF-beta1-induced MMP-9 via Smad and MAPK pathways in human corneal epithelial cells. Invest Ophthalmol Vis Sci 2005; 46(3):840-8.
45. Solomon A, Dursun D, Liu Z, Xie Y, Macri A, Pflugfelder S C. Pro- and anti-inflammatory forms of interleukin-1 in the tear fluid and conjunctiva of patients with dry-eye disease. Invest Ophthalmol Vis Sci 2001; 42(10):2283-92.
46. Li D Q, Luo L, Chen Z, Kim H S, Song X J, Pflugfelder S C. JNK and ERK MAP kinases mediate induction of IL-1beta, TNF-alpha and IL-8 following hyperosmolar stress in human limbal epithelial cells. Exp Eye Res 2006; 82(4):588-96.
47. Pflugfelder S C, Jones D, Ji Z, Afonso A, Monroy D. Altered cytokine balance in the tear fluid and conjunctiva of patients with Sjogren's syndrome keratoconjunctivitis sicca. Curr Eye Res 1999; 19(3):201-11.
48. Abelson M B L, Lauren. Melting Away the Myths of NSAIDs. Review of Ophthalmology 2007; 14(11): 124-28.
49. Shim J, Park C, Lee H S, Park M S, Lim H T, Chauhan S, et al. Change in prostaglandin expression levels and synthesizing activities in dry eye disease. Ophthalmology 2012; 119(11):2211-9.
50. McGinnigle S, Naroo S A, Eperjesi F. Evaluation of dry eye. Sury Ophthalmol 2012; 57(4):293-316.
51. Mackenzie G G, Ouyang N, Xie G, Vrankova K, Huang L, Sun Y, et al. Phospho-sulindac (OXT-328) combined with difluoromethylornithine prevents colon cancer in mice. Cancer Prev Res (Phila) 2011; 4(7):1052-60.
52. Guidera A C, Luchs J I, Udell U. Keratitis, ulceration, and perforation associated with topical nonsteroidal anti-inflammatory drugs. Ophthalmology 2001; 108(5):936-44.

The invention claimed is:

1. A method of treating an ophthalmic condition in a mammal, in need thereof comprising administering to the mammal a formulation comprising a compound of Formula I: wherein the compound of Formula I is selected from:

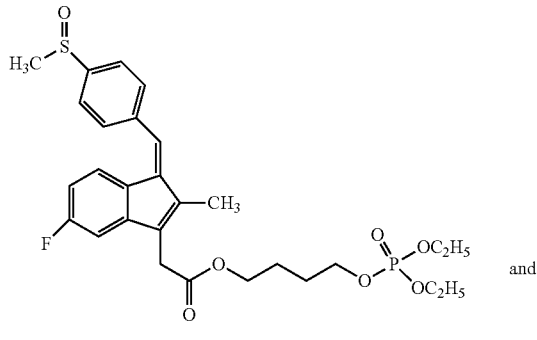

(PS)

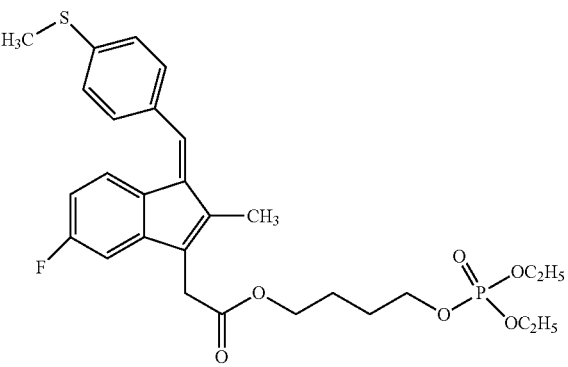

or a salt thereof,
wherein the ophthalmic condition is dry-eye disease and wherein the compound is administered topically to an eye of the mammal.

2. The method of claim 1, wherein the compound of Formula I is

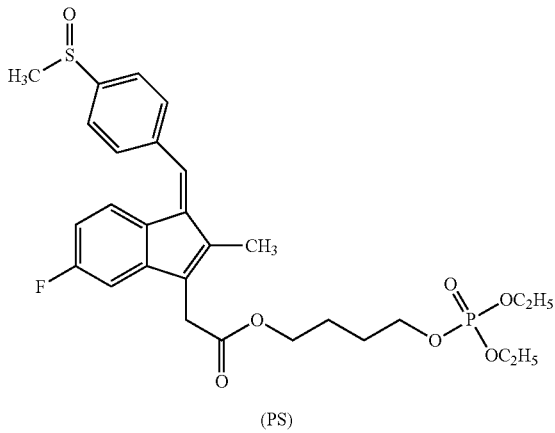

(PS)

or a salt thereof.

3. The method of claim 1, wherein the compound is administered at least once daily for at least two days.

4. The method of claim 1, wherein the compound is administered at least once daily for at least seven days.

5. A method of treating an ophthalmic condition in a patient in need thereof, wherein the ophthalmic condition is dry eye disease, the method comprising administering to the patient a therapeutically effective amount of a formulation comprising a compound of formula III or formula IV:

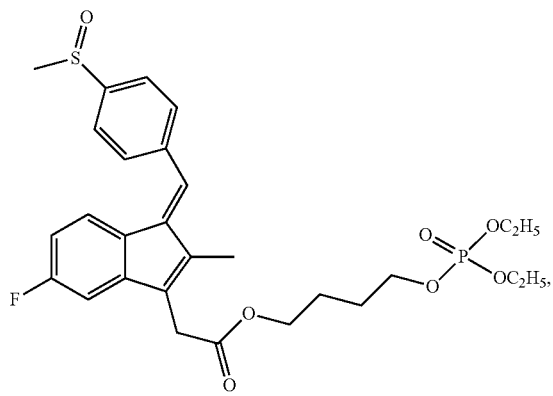

(III)

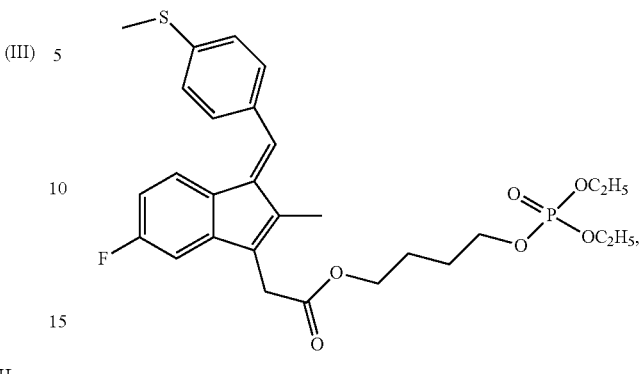

(IV)

or a pharmaceutically acceptable salt thereof, wherein the compound is administered topically to tissues surrounding an eye, to an eyelid, and/or to an eye of the patient.

6. The method of claim 5, wherein the method comprises administering a therapeutically effective amount of a compound of formula III, or a pharmaceutically acceptable salt thereof.

7. The method of claim 5, comprising the step of administering a therapeutically effective amount of an additional active agent.

8. The method of claim 7, wherein the additional active agent is selected from the group consisting of an antibiotic, cyclosporine, lifitegrast, and a combination thereof.

9. The method of claim 5, wherein the compound is administered topically to the patient in an eye drop dosage form.

10. The method of claim 1, wherein the compound is administered at least once daily, and wherein the administration continues for more than about 28 days, two months, six months, or one year.

11. The method of claim 1, wherein the compound is administered in an amount of 0.01 to 1000 mg per day.

12. The method of claim 5, wherein the compound is administered at least once daily, and wherein the administration continues for more than about 28 days, two months, six months, or one year.

13. The method of claim 5, wherein the compound is administered in an amount of 0.01 to 1000 mg per day.

* * * * *